United States Patent
Bevilacqua et al.

(10) Patent No.: US 12,268,722 B2
(45) Date of Patent: *Apr. 8, 2025

(54) COMPOSITIONS AND USES OF LOCALLY-APPLIED ANTIMICROBIAL SYNTHETIC CATIONIC POLYPEPTIDE(S) WITH ENHANCED PERFORMANCE AND SAFETY

(71) Applicant: AMICROBE, INC., Carlsbad, CA (US)

(72) Inventors: Michael P. Bevilacqua, Carlsbad, CA (US); Daniel J. Huang, Carlsbad, CA (US); Doug Looker, Carlsbad, CA (US)

(73) Assignee: AMICROBE, INC., Carlsbad, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 17/654,021

(22) Filed: Mar. 8, 2022

(65) Prior Publication Data

US 2023/0017994 A1 Jan. 19, 2023

Related U.S. Application Data

(63) Continuation of application No. 16/500,288, filed as application No. PCT/US2018/026322 on Apr. 5, 2018, now Pat. No. 11,285,189.

(60) Provisional application No. 62/482,630, filed on Apr. 6, 2017.

(51) Int. Cl.

| A61K 38/02 | (2006.01) |
|---|---|
| A61K 9/06 | (2006.01) |
| A61K 9/08 | (2006.01) |
| A61K 45/06 | (2006.01) |
| A61L 26/00 | (2006.01) |
| A61P 31/04 | (2006.01) |

(52) U.S. Cl.
CPC ............... *A61K 38/02* (2013.01); *A61K 9/06* (2013.01); *A61K 9/08* (2013.01); *A61K 45/06* (2013.01); *A61L 26/0047* (2013.01); *A61P 31/04* (2018.01); *A61L 2300/252* (2013.01); *A61L 2300/404* (2013.01)

(58) Field of Classification Search
None
See application file for complete search history.

(56) References Cited

U.S. PATENT DOCUMENTS

| 6,632,922 | B1 | 10/2003 | Deming et al. |
|---|---|---|---|
| 6,680,365 | B1 | 1/2004 | Deming |
| 6,686,446 | B2 | 2/2004 | Deming et al. |
| 6,818,732 | B2 | 11/2004 | Deming et al. |
| 7,279,458 | B2 | 10/2007 | Fatheree et al. |
| 7,329,727 | B2 | 2/2008 | Deming |
| 7,847,059 | B2 | 12/2010 | O'Neil |
| 8,088,888 | B2 | 1/2012 | O'Neil |
| 8,138,144 | B2 | 3/2012 | Krieger et al. |
| 8,350,003 | B2 | 1/2013 | O'Neil |
| 8,470,769 | B2 | 6/2013 | O'Neil |
| 9,017,730 | B2 | 4/2015 | Bevilacqua et al. |
| 9,446,090 | B2 | 9/2016 | Bevilacqua et al. |
| 11,285,189 | B2 * | 3/2022 | Bevilacqua ............ A61K 38/02 |
| 2007/0190110 | A1 | 8/2007 | Pamerijer et al. |
| 2008/0125581 | A1 | 5/2008 | Deming et al. |
| 2010/0003336 | A1 | 1/2010 | Deming et al. |
| 2013/0267458 | A1 | 10/2013 | Bevilacqua et al. |
| 2015/0080290 | A1 | 3/2015 | Bevilacqua et al. |
| 2015/0225458 | A1 | 8/2015 | Rapsch et al. |
| 2016/0120936 | A1 | 5/2016 | Troxel |
| 2017/0042965 | A1 | 2/2017 | Bevilacqua et al. |

FOREIGN PATENT DOCUMENTS

| CN | 104582688 A | 4/2015 |
|---|---|---|
| CN | 110740744 A | 1/2020 |
| EP | 1 002 547 A1 | 5/2000 |
| EP | 1 473 584 A1 | 11/2004 |
| EP | 2 359 859 A1 | 3/2011 |
| EP | 2 292 270 A1 | 8/2011 |
| EP | 2 827 841 | 1/2015 |
| EP | 2666484 | 11/2016 |
| EP | 3 606 543 A1 | 2/2020 |
| JP | 2003-171463 | 6/2003 |
| JP | 2005-504769 | 2/2005 |
| JP | 2007-517027 | 6/2007 |
| JP | 2010-527335 | 8/2010 |
| JP | 2010-531189 | 9/2010 |

(Continued)

OTHER PUBLICATIONS

Isaksson et al. (In vivo toxicity and bio distribution of intraperitoneal and intravenous poly-L-lysine and poly-L-lysine/poly-L-glutamate in rats; Journal of Materials Science: Materials in Medicine (2014) vol. 25,p. 1293-1299). (Year: 2014).*
Anonymous, Save-ory TM GL610 General Information, Internet Citation, Feb. 9, 2006, XP002366870, Retrieved from the internet: URL:http://www.save-ory.com/documents/gigl610.pdf.
Bevilacqua, M., et al: "Amino Acid Block Copolymers with Broad Antimicrobial Activity and Barrier Properties", Macromolecular Bioscience, vol. 17, No. 10, Mar. 1, 2017 (Mar. 1, 2017), p. 1600492.
Bjarnsholt, T., "The Role of Bacterial Biofilms in Chronic Infections," Acta Pathologica, Microbiologica et. Immunologica Scandinavica (2013) 121 (Suppl. 136): 1-51.

(Continued)

*Primary Examiner* — Melissa S Mercier
(74) *Attorney, Agent, or Firm* — Knobbe, Martens, Olson & Bear, LLP

(57) ABSTRACT

Antimicrobial pharmaceutical compositions are formulated to allow local application in vivo of doses that provide antimicrobial effectiveness with low risk of local tissue toxicities and/or low risk of systemic/distant organ toxicities. In various embodiments the antimicrobial pharmaceutical compositions comprise antimicrobial synthetic cationic polypeptide(s) that are dispersed in an aqueous carrier and formulated to achieve a desired degree of polymer self-assembly and/or composition viscosity.

17 Claims, 57 Drawing Sheets

(56) References Cited

FOREIGN PATENT DOCUMENTS

| | | | | |
|---|---|---|---|---|
| JP | 2010-537997 | 12/2010 | | |
| JP | 2016-113373 | 6/2016 | | |
| JP | 6224069 B2 | 11/2017 | | |
| KR | 1020100049039 | 5/2010 | | |
| KR | 1020110095867 | 8/2011 | | |
| KR | 1020120003893 | 1/2012 | | |
| KR | 1020150013133 | 2/2015 | | |
| RU | 2180855 C2 | 3/2002 | | |
| RU | 2415150 C2 | 3/2011 | | |
| WO | WO 1994/020041 | 9/1994 | | |
| WO | WO 2000/050006 | 8/2000 | | |
| WO | WO 2002/026209 | 4/2002 | | |
| WO | WO 2003/015809 | 2/2003 | | |
| WO | WO 2005/018701 | 3/2005 | | |
| WO | WO 2005/094891 | 10/2005 | | |
| WO | WO 2009/001087 | 12/2008 | | |
| WO | WO 2009/032605 | 3/2009 | | |
| WO | WO 2010/083589 | 7/2010 | | |
| WO | WO 2011/134998 | 11/2011 | | |
| WO | WO-2012027411 | A2 * | 3/2012 | ............. A01N 37/18 |
| WO | WO 2012/098653 | 7/2012 | | |
| WO | WO 2012/135685 | 10/2012 | | |
| WO | WO 2013/142374 | 9/2013 | | |
| WO | WO 2016/044683 A1 | 3/2016 | | |
| WO | WO 2018/187617 A1 | 10/2018 | | |
| WO | WO 2019/169324 A1 | 9/2019 | | |

OTHER PUBLICATIONS

Davies, D. "Understanding Biofilm Resistance to Antibacterial Agents." Nature Reviews—Drug Discovery, vol. 2, Feb. 2003, pp. 114-122.
Dobry A. et al., "Phase Separation in Polymer Solution," Journal of Polymer Science, vol. 2, No. 1, pp. 90-100, 1947.
Isaksson, K. et al., "In vivo toxicity and biodistribution of intraperitoneal and intravenous poly-L-lysine and poly-L-lysine/poly-L-glutamate in rats", J Mater Sci: Mater Med (2014) 25:1293-1299.
Katchalski, E. et al. "The Action of Some Water-soluble Poly-α-amino Acids on Bacteria" Biochemical Journal (1953) vol. 55, pp. 671 to 680.
Sperling, L.H., Introduction to Physical Polymer Science, 1986, pp. 111-116, John Wiley & Sons, U.S.
Vidaza (azacitidine for injection) Product Label, Approved 2004; Revised: Aug. 2011, Reference ID: 3002164.
Search Report issued in corresponding EP Application No. 18780547.8 dated Nov. 16, 2020.
International Search Report and Written Opinion of the International Searching Authority mailed May 9, 2013, in corresponding International Application No. PCT/US2013/032535.
International Preliminary Report on Patentability, PCT Application No. PCT/US2013/032535, mailed Mar. 23, 2012, in 7 pages.
International Search Report for PCT Application No. PCT/US2018/026322 dated Jun. 29, 2018.
International Preliminary Report on Patentability for PCT Application No. PCT/US2018/026322 dated Feb. 27, 2019.
Office Action for Russian Application No. 2019133628/04(066381) issued on Jul. 14, 2021.
Notice of Reasons for Refusal for Japanese Patent Application No. 2019-554855 dated Jan. 5, 2022.
Examination Report 1 for Australian Patent Application No. 2018249552 by Australian IP Office dated Apr. 13, 2022.
Examination Report 2 for Australian Patent Application No. 2018249552 by Australian IP Office dated, Oct. 20, 2022.
The First Office Action for Chinese Application No. 2018800379989 by National Intellectual Property Administration, PRC dated Oct. 21, 2022.
The Second Office Action for Chinese Application No. 2018800379989 by National Intellectual Property Administration, PRC dated May 18, 2023.
Examiner Requisition for Canadian Application No. 3,058,901 by Canadian IP Office dated May 30, 2023.
Office Action for EP Application No. 18789547.8 dated Mar. 29, 2023.
Office Action for Korean Application No. 10-2019-7032623 dated Mar. 29, 2023.

* cited by examiner

| Group | Cationic Segment Length | Cationic:Hydrophobic Block Length Ratio | Approximate MW (Da) |
|---|---|---|---|
| I. Long Cationic Segment | 200-400 | 1.5 to 15 | >32,000 |
| II. Medium Cationic Segment | 100-199 | 1.5 to 15 | 16,000 to 32,000 |
| III. Short Cationic Segment | 10-99 | 1.5 to 15 | <16,000 |

| Group | Cationic Segment (Plurality of cationic amino acid units) | | Hydrophobic Segment (Plurality of hydrophobic amino acid units) | |
|---|---|---|---|---|
| | Cationic Amino Acid Selection | Lengths | Hydrophobic Amino Acid Selection | Cationic:hydrophobic Segment Length Ratio |
| I. Long Cationic Segment ≥200 amino acid units with a plurality of cationic amino acid units | Lysine (K) | 200-400 | Alanine (A) Phenylalanine (F) Glycine (G) Isoleucine (I) Leucine (L) Methionine (M) Proline (P) | 1.5 to 15 |
| | Arginine (R) | 200-400 | | |
| | Histidine (H) | 200-400 | | |
| | Ornithine (O) | 200-400 | | |
| II. Medium Cationic Segment 100 to 199 amino acid units with a plurality of cationic amino acid units | Lysine (K) | 100-199 | Alanine (A) Phenylalanine (F) Glycine (G) Isoleucine (I) Leucine (L) Methionine (M) Proline (P) | 1.5 to 15 |
| | Arginine (R) | 100-199 | | |
| | Histidine (H) | 100-199 | | |
| | Ornithine (O) | 100-199 | | |
| III. Short Cationic Segment 10 to 99 amino acid units with a plurality of cationic amino acid units | Lysine (K) | 10-99 | Alanine (A) Phenylalanine (F) Glycine (G) Isoleucine (I) Leucine (L) Methionine (M) Proline (P) | 1.5 to 15 |
| | Arginine (R) | 10-99 | | |
| | Histidine (H) | 10-99 | | |
| | Ornithine (O) | 10-99 | | |

FIG. 3

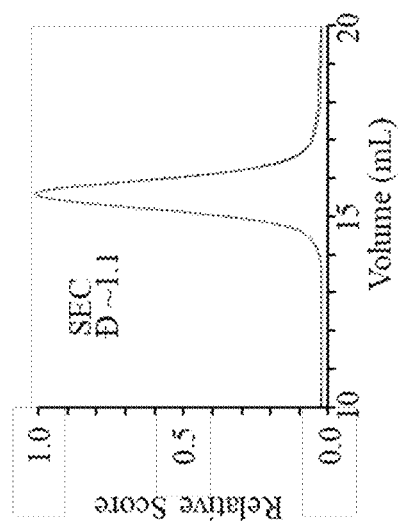
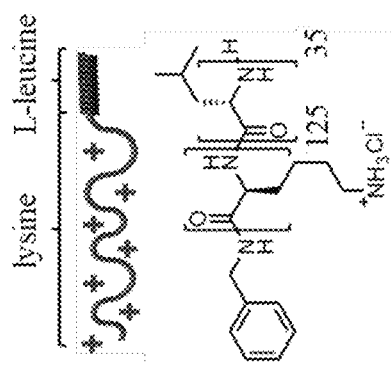
FIG. 4

| | Microbe | % CFU Reduction |
|---|---|---|
| Gram positive | *S. aureus* | 99.99% |
| | MRSA* | 99.98% |
| | **Vancomycin-resistant *E. faecium* (VRE)*** | 100% |
| | *S. pyogenes* | 99.74% |
| Gram negative | *A. baumannii** | 100% |
| | **MDR *A. baumannii*** | 100% |
| | **ESBL *E. coli*** | 100% |
| | *K. pneumoniae* | 100% |
| | **ESBL, KPC *K. pneumoniae*** | 100% |
| | *P. aeruginosa* | 100% |
| | **MDR *P. aeruginosa*** | 100% |
| Anaerobe | **MDR *B. fragilis*** | 99.80% |
| Fungi | *C. albicans* | 100% |
| | **Fluconazole-resistant *C. albicans*** | 100% |

FIG. 6

| | Microbe | Microbes (t=0 min) | Microbes (t=60 min) | % CFU Reduction |
|---|---|---|---|---|
| Gram positive | S. aureus | 1,260,000 | 0 | 100% |
| | MRSA* | 1,380,000 | 0 | 100% |
| | Vancomycin-resistant E. faecium (VRE)* | 955,000 | 0 | 100% |
| | S. pyogenes | 2,630,000 | 60 | 99.99% |
| Gram negative | A. baumannii* | 1,450,000 | 0 | 100% |
| | MDR A. baumannii* | 2,000,000 | 0 | 100% |
| | ESBL E. coli* | 1,480,000 | 0 | 100% |
| | K. pneumoniae | 2,190,000 | 0 | 100% |
| | ESBL, KPC K. pneumoniae* | 1,450,000 | 200 | 99.99% |
| | P. aeruginosa | 2,190,000 | 0 | 100% |
| | MDR P. aeruginosa* | 2,190,000 | 0 | 100% |
| Anaerobe | MDR B. fragilis* | 776,000 | 0 | 100% |
| Fungi | C. albicans | 115,000 | 0 | 100% |
| | Fluconazole-resistant C. albicans* | 100,000 | 0 | 100% |

FIG. 9

| Molecular Type | Polypeptide Designation | Lot | CAC (µg/mL) |
|---|---|---|---|
| Polylysine | K-100 | 79 | 1,600 |
| Lysine + L-leucine | KL-130/3.3-RAN | 80 | 2,700 |
| | KL-170/3.3 | 111 | 8 |
| | KL-160/3.2 | BAC003 | 19 |
| | KL-150/2.0 | 74 | 2 |
| | KL-140/2.5 | 99 | 8 |
| | KL-140/2.5 | 73 | 1 |
| | KL-130/3.3 | 72 | 6 |
| | KL-120/5.0 | 71 | 21 |
| | KL-120/2.5 | BAC004 | 10 |
| Lysine + D,L-leucine | KrL-170/3.3 | 104 | 4 |
| | KrL-160/3.2 | BAC001 | 34 |
| | KrL-140/2.5 | 78 | 6 |
| | KrL-130/3.3 | 77 | 4 |
| | KrL-120/5.0 | 93 | 130 |
| | KrL-120/5.0 | 94 | 51 |
| | KrL-120/5.0 | 76 | 14 |
| | KrL-100/5.7 | BAC002 | 160 |

| Molecular Type | Polypeptide Designation | Lot | Viscosity (cSt) | Ubbelohde Size |
|---|---|---|---|---|
| Lysine + L-leucine | KL-160/3.3 | BAC003 | 17 | 1B |
|  | KL-120/2.5 | BAC004 | 9 | 1 |

FIG. 14

| Molecular Type | Polypeptide Designation | Lot | Viscosity (cSt) 1wt% | Viscosity (cSt) 2wt% | Ubbelohde Size |
|---|---|---|---|---|---|
| Lysine + L-leucine | KL-160/3.2 | D-303-18A | 24.8 | - | 1B |
|  | KL-100/5.7 | D-301-67-03 | 5.53 | 15.17 | 1, 1B |
| Lysine + D,L-leucine | KrL-160/3.3 | BAC001 | 5.0 | 20.7 | 1, 1B |
|  | KrL-110/4.0 | D-301-37-05 | 2.78 | 6.45 | 0B, 1C |

| Polypeptide Designation | Lot | Viscosity (cSt) @ 1wt% | | |
|---|---|---|---|---|
| | | Water | Saline (0.9%) | Xylitol (4.4%) |
| KL-100/5.7 | D-301-67-03 | 5.53 | 1.50 | 5.94 |
| KtL-110/4.0 | D-301-37-05 | 2.78 | 1.69 | 3.14 |

FIG. 20

| Synthetic Cationic Polypeptide(s) | Lot | Surface Tension (dynes/cm) |
|---|---|---|
| Water | - | 72.2 |
| KL-120/5.0 | 71 | 68.8 |
| KL-130/3.3 | 72 | 71.5 |
| KL-140/2.5 | 73 | 72.4 |
| KL-150/2.0 | 74 | 72.3 |
| KrL-120/5.0 | 76 | 54.2 |
| KrL-130/3.3 | 77 | 59.1 |
| KrL-140/2.5 | 78 | 60.1 |
| KrL-150/6.5 | 92 | 65.7 |
| KrL-170/3.3 | 104 | 57.8 |

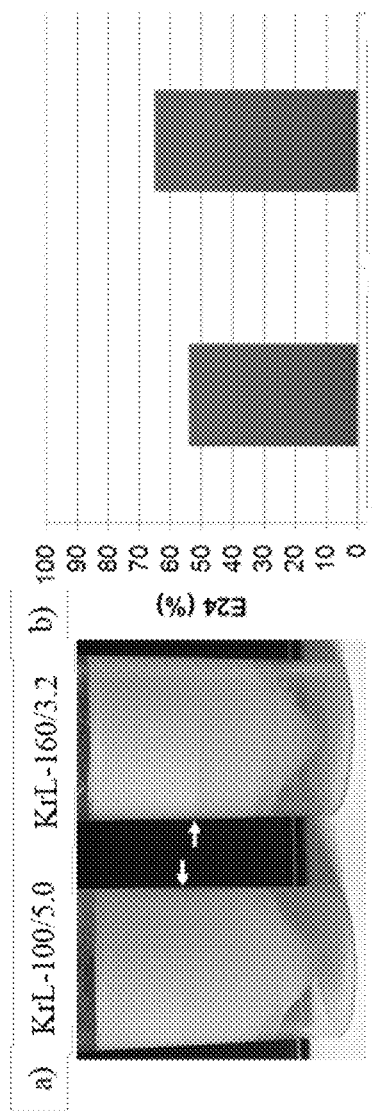
FIGS. 27A-B
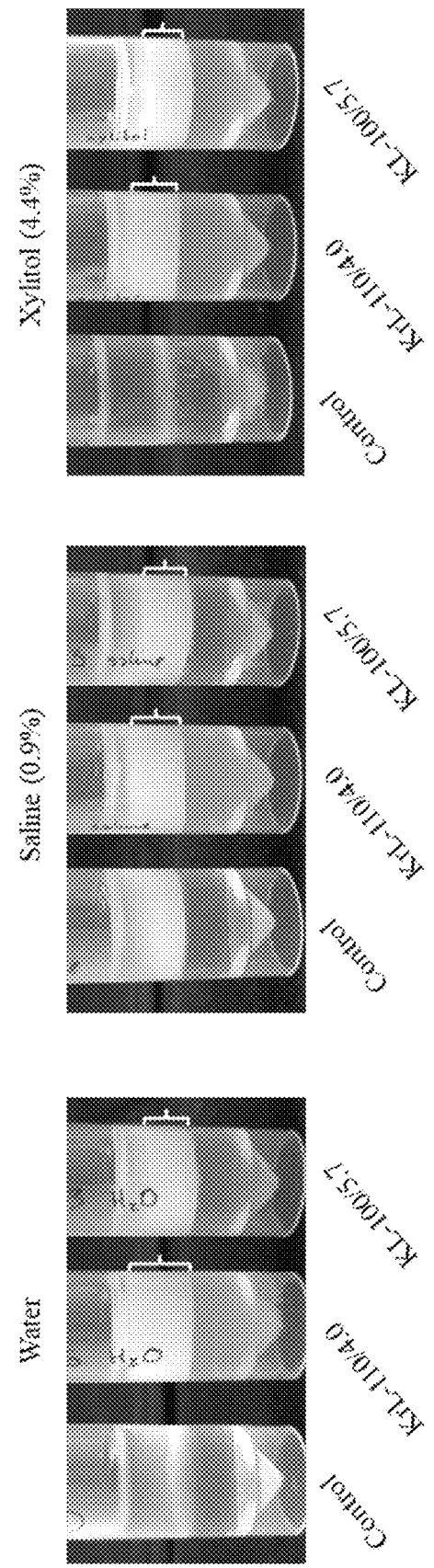
FIG. 28

| Synthetic Cationic Polypeptide(s) | Concentration (mg/mL) | Formulation (+ water) | Score | | Response Category |
|---|---|---|---|---|---|
| | | | Intact Skin | Abraded Skin | |
| KL-140/2.5 (Lot 73) | 10 | - | 0 | 0 | Negligible |
| | 20 | - | 0 | 0 | Negligible |
| | 5 | 10 mg/mL HEC | 0 | 0 | Negligible |
| | 10 | 5 mg/mL HEC | 0.06 | 0 | Negligible |
| KrL-120/5.0 (Lot 76) | 10 | - | 0 | 0 | Negligible |
| | | 2 mg/mL P407 | 0 | 0 | Negligible |
| | | 5 mg/mL HEC | 0 | 0 | Negligible |
| | | 30 mg/mL PEG400 | 0 | 0 | Negligible |

FIG. 29

| KL-140/2.5 (Lot 73), 1wt% | | | | KrL-120/5.0 (Lot 93) 1wt% | | |
|---|---|---|---|---|---|---|
| Animal # | Challenge Scores | | | Animal # | Challenge Scores | |
| | 24h | 48h | | | 24h | 48h |
| 12497 | 0 | 0 | | 12450 | 0 | 0 |
| 12501 | 0 | 0 | | 12451 | 0 | 0 |
| 12503 | 0 | 0 | | 12452 | 0 | 0 |
| 12508 | 0 | 0 | | 12453 | 0 | 0 |
| 12514 | 0 | 0 | | 12454 | 0 | 0 |
| 12519 | 0 | 0 | | 12455 | 0 | 0 |
| 12520 | 0 | 0 | | 12456 | 0 | 0 |
| 12522 | 0 | 0 | | 12458 | 0 | 0 |
| 12525 | 0 | 0 | | 12459 | 0 | 0 |
| 12529 | 0 | 0 | | 12460 | 0 | 0 |
| 12532 | 0 | 0 | | 12461 | 0 | 0 |

| Scale | Patch test reaction |
|---|---|
| 0 | No visible change |
| 1 | Discreet or patchy erythema |
| 2 | Moderate and confluent erythema |
| 3 | Intense erythema and swelling |

FIG. 30

| Synthetic Cationic Polypeptide(s) | Concentration (mg/mL) | Dosage (mg/kg) | Response |
|---|---|---|---|
| KL-140/2.5 (Lot 76) | 20 | 160 | No abnormalities noted |
| | 5 | 40 | No abnormalities noted |
| | 1.25 | 10 | No abnormalities noted |
| | 0.31 | 2.5 | No abnormalities noted |
| | 0.078 | 0.625 | No abnormalities noted |
| KrL-120/5.0 (Lot 76) | 20 | 160 | No abnormalities noted |
| | 5 | 40 | No abnormalities noted |
| | 1.25 | 10 | No abnormalities noted |
| | 0.31 | 2.5 | No abnormalities noted |
| | 0.078 | 0.625 | No abnormalities noted |

FIG. 31

| Synthetic Cationic Polypeptide(s) | Concentration (mg/mL) | Dosage (mg/kg) | Formulation | Survival |
|---|---|---|---|---|
| KiL-130/3.3 (Lot 77) | 20 | 800 | Water | 5/5 |
| | 5 | 200 | | 5/5 |
| | 1.25 | 50 | | 5/5 |
| | 0.31 | 12.5 | | 5/5 |
| Saline | - | - | - | 5/5 |

| Synthetic Cationic Polypeptide(s) | Concentration (mg/mL) | Dosage (mg/kg) | Formulation | Survival |
|---|---|---|---|---|
| KrL-120/5.0 (Lot 93) | 20 | 800 | Water | 0/0 |
| | 5 | 200 | | 0/0 |
| | 1.25 | 50 | | 5/5 |
| KrL-120/5.0 (Lot 94) | 20 | 800 | Water | 5/5 |
| | 5 | 200 | | 5/5 |
| | 1.25 | 50 | | 5/5 |

FIG. 34

| Synthetic Cationic Polypeptide(s) | Concentration (mg/mL) | Dosage (mg/kg) | Formulation | Survival |
|---|---|---|---|---|
| KL-170/3.3 (Lot 86) | 10 | 400 | Water | 5/5 |
| | 2.5 | 100 | | 5/5 |
| | 0.63 | 25 | | 5/5 |
| | 0.16 | 6.25 | | 5/5 |
| KL-140/2.5 (Lot 73) | 10 | 400 | Water | 5/5 |
| | 2.5 | 100 | | 5/5 |
| | 0.63 | 25 | | 5/5 |
| | 0.16 | 6.25 | | 5/5 |
| Water | - | - | - | 5/5 |

FIG. 35

| Synthetic Cationic Polypeptide(s) | Concentration (mg/mL) | Dosage (mg/kg) | Formulation | Survival |
|---|---|---|---|---|
| KL-140/2.5 (Lot 73) | 10 | 400 | Water | 5/5 |
| | 2.5 | 100 | | 5/5 |
| | 0.63 | 25 | | 5/5 |
| | 0.16 | 6.25 | | 5/5 |
| | 5 | 200 | 10 mg/mL HEC | 3/5 |
| | 1.25 | 50 | 2.5 mg/mL HEC | 5/5 |
| | 0.31 | 12.5 | 0.625 mg/mL HEC | 5/5 |
| | 0.08 | 3.125 | 0.156 mg/mL HEC | 5/5 |
| | 2 | 80 | 15 mg/mL HEC | 2/5 |
| | 0.5 | 20 | 3.75 mg/mL HEC | 4/5 |
| | 0.125 | 5 | 0.937 mg/mL HEC | 5/5 |
| | 0.031 | 1.25 | 0.234 mg/mL HEC | 5/5 |
| Water | - | - | - | 5/5 |

FIG. 36

| Synthetic Cationic Polypeptide(s) | Concentration (mg/mL) | Dosage (mg/kg) | Formulation | Survival |
|---|---|---|---|---|
| KrL-120/5.0 (Lot 94) | 20 | 800 | Water | 5/5 |
| | 5 | 200 | | 5/5 |
| | 1.25 | 50 | | 5/5 |
| | 20 | 800 | Normal Saline | 5/5 |
| | 5 | 200 | 4x dilution above | 5/5 |
| | 1.25 | 50 | 4x dilution above | 5/5 |
| | 20 | 800 | ½ Normal Saline | 4/5 |
| | 5 | 200 | 4x dilution above | 4/5 |
| | 1.25 | 50 | 4x dilution above | 5/5 |
| | 20 | 800 | 5 mg/mL T20 + 1 glu/chain | 3/5 |
| | 5 | 200 | 4x dilution above | 5/5 |
| | 1.25 | 50 | 4x dilution above | 5/5 |
| | 20 | 800 | 5 mg/mL T20 + 5 glu/chain | 4/5 |
| | 5 | 200 | 4x dilution above | 5/5 |
| | 1.25 | 50 | 4x dilution above | 5/5 |

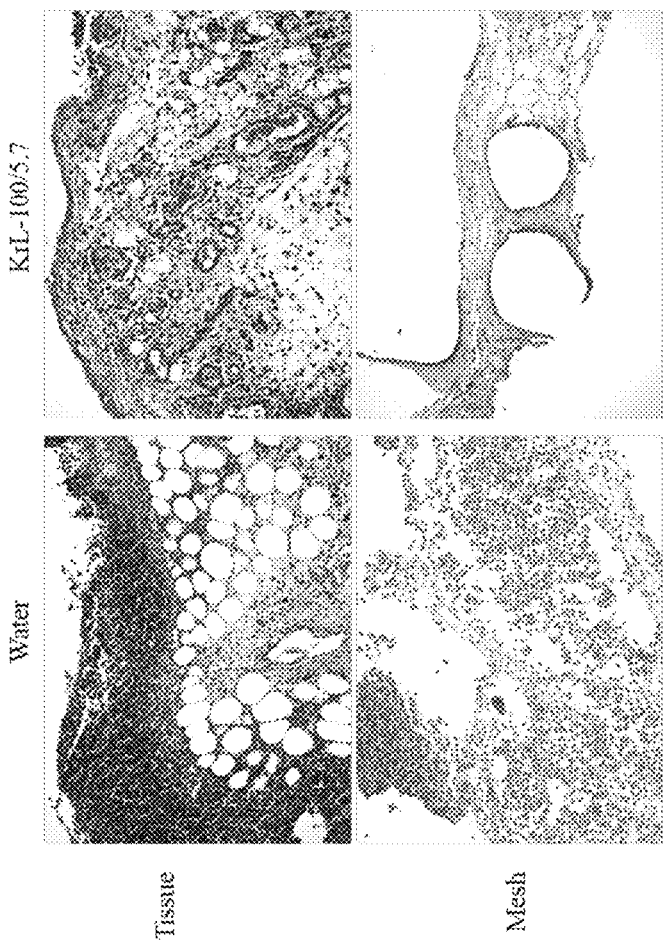
FIGS. 63A-B

COMPOSITIONS AND USES OF LOCALLY-APPLIED ANTIMICROBIAL SYNTHETIC CATIONIC POLYPEPTIDE(S) WITH ENHANCED PERFORMANCE AND SAFETY

RELATED APPLICATION INFORMATION

This application is a continuation of U.S. application Ser. No. 16/500,288, filed Oct. 2, 2019, as a 371 of PCT/US2018/026322, filed Apr. 5, 2018, which claims priority to U.S. provisional application Ser. No. 62/482,630, filed Apr. 6, 2017. All of the foregoing are hereby incorporated by reference in their entireties.

BACKGROUND

Field

This disclosure relates to antimicrobial pharmaceutical compositions that contain cationic antimicrobials and methods of using them to prevent and/or treat infections.

Description of the Related Art

Locally applied antimicrobials, including antiseptics and antibiotics, often fail to achieve effectiveness in the prevention and treatment of infections, resulting in substantial patient morbidity and mortality. Specific uses (including application to certain tissues) and doses (concentration, volume, number of applications) may be limited by the risk of one or more toxicities. Concerns regarding such toxicities may result in clinical application of inadequate doses or avoidance of use altogether in certain pathophysiological settings.

A wide variety of cationic antimicrobials are known for their ability to bind to and disrupt bacterial membranes, including certain antibiotics, bisbiguanides, polymer biguanides, quaternary ammonium compounds, natural antimicrobial peptides, and synthetic cationic polypeptides. However, mammalian toxicity has remained a consistent problem.

U.S. Pat. No. 9,017,730 describes synthetic cationic copolypeptides containing varying ratios of cationic amino acid recurring units (such as lysine (K)) and hydrophobic amino acid units (such as leucine (L), isoleucine (1), valine (V), phenylalanine (F) or alanine (A)). U.S. Pat. No. 9,017,730 indicates that a segmented or block architecture involving stretches of cationic amino acids and stretches of hydrophobic amino acids can improve compatibility with mammalian cells, as measured by in vitro cytotoxicity assays. In addition, U.S. Pat. No. 9,017,730 indicates that incorporation of selected cationic block copolypeptides into an emulsion can improve compatibility with mammalian cells in vitro, as measured by cytotoxicity assays. While U.S. Pat. No. 9,017,730 describes local application of a number of synthetic cationic copolypeptide preparations, it does not provide evidence of toxicities that may result from the use of these preparations in vivo.

U.S. Pat. No. 9,446,090 describes synthetic cationic polypeptide(s) along with mutually water-miscible mixtures that contain such a polypeptide and a second pharmaceutically acceptable polymer. Specific examples describe antimicrobial activity against certain bacteria using particular mixtures of synthetic cationic polypeptide(s) with second polymers such as polyethylene glycol (PEG), hydroxyethylcellulose (HEC), and Poloxamer 407. Even though the second polymers alone were not known to have significant antimicrobial activity, the data indicated that in the mixtures, addition of the second polymer maintained the antimicrobial activity of the synthetic cationic polypeptide(s) in vitro and in some cases, enhanced overall antimicrobial performance in vivo. However, U.S. Pat. No. 9,446,090 does not provide evidence of toxicities that may result from the use of these mixtures of synthetic cationic polypeptide(s) with other pharmaceutically-acceptable polymers in vivo. Further, it leaves open the possibility that the second polymer may increase the toxicity of the mixtures, as compared to the synthetic cationic polypeptide(s) alone.

While U.S. Pat. Nos. 9,017,730 and 9,446,090 describe significant advances in the art, a number of challenges remain, particularly with respect to developing pharmaceutically acceptable preparations of locally applied cationic antimicrobials that have both high efficacy and high safety in vivo.

SUMMARY

We have developed cationic antimicrobial pharmaceutical compositions and methods of use that allow local applications in vivo of doses that provide antimicrobial effectiveness with low risk of local tissue toxicities and/or low risk of systemic/distant organ toxicities.

In developing the present invention, we found that the risk of toxicities after local application of cationic antimicrobials in vivo are particularly relevant when they are applied in abundance to tissue sites, or in pathophysiological settings, other than healthy intact skin. Such sites and pathophysiological settings may include open wounds, body cavities, body orifices, diseased skin, and others. These tissue sites and pathophysiological settings may demonstrate higher local sensitivities and/or higher absorption and systemic distribution of the locally applied antimicrobial agents or excipients, as compared to healthy, intact skin. Greater local tissue toxicities and greater systemic/distant organ toxicities may follow.

Further, we made a series of discoveries that helped guide the development of the invention. First, we discovered that changes in the molecular design of synthetic cationic polypeptide(s) can have different effects on antimicrobial efficacy and toxicities in vivo; second, we discovered that changes in formulation of synthetic cationic polypeptide(s) can have different effects on antimicrobial efficacy and toxicities in vivo; and third, we discovered that sterilization of synthetic cationic polypeptide(s) preparations can adversely affect molecular integrity and biophysical properties, and thereby affect antimicrobial effectiveness, toxicities, or both. Thus, we discovered a combination of problems for which solutions have now been developed.

In various embodiments, pharmaceutical compositions and methods of use are provided that allow local applications of effective doses of antimicrobial synthetic cationic polypeptide(s) to various tissue sites and/or in various pathophysiological settings with low risk of local and/or systemic toxicities. Without limiting the scope of the invention, in various embodiments this is achieved by one or more of (A), (B) and (C), as follows:

(A) Design of the antimicrobial synthetic cationic polypeptide(s), especially hydrophobic content and sequence arrangement, to promote increased viscosity in water. Unexpectedly, this design feature was found to enhance safety in vivo.

(B) Formulating antimicrobial synthetic cationic polypeptide(s) into pharmaceutical compositions in a way that allows them to exhibit viscosity-enhancing properties. Without limiting the scope of the invention, this approach is believed to have the effect of improving tissue coverage and/or enhancing retention time, yielding greater effectiveness for an applied dose. In addition, such improvements in formulation were found unexpectedly to enhance safety. Without limiting the scope of the invention, excipients may include salts such as sodium chloride and potassium chloride, sugars and sugar alcohols such as dextrose, mannitol, glycerol, xylitol, and sorbitol, surfactants, and combinations thereof.

(C) Sterilization of the pharmaceutical compositions in a way that allows the sterilized pharmaceutical composition to exhibit a viscosity comparable to the viscosity of the unsterilized pharmaceutical composition. Without limiting the scope of the invention, this approach is believed to have the effect of protecting the molecular structure and function of the antimicrobial synthetic cationic polypeptide(s), as well as decreasing the risk of product contamination by certain microbial organisms (e.g., fungal dermatophytes) that may exhibit resistance to effects of the antimicrobial synthetic cationic polypeptide(s).

An embodiment provides an antimicrobial pharmaceutical composition, comprising: an aqueous carrier; and an antimicrobial synthetic cationic polypeptide(s) dispersed in the aqueous carrier at a concentration in the range of about 0.01% to about 5%, by weight based on total weight of the antimicrobial pharmaceutical composition. In an embodiment, the antimicrobial synthetic cationic polypeptide(s) comprises a plurality of positively charged amino acid units at neutral pH. In an embodiment, the antimicrobial synthetic cationic polypeptide(s) at a concentration of 2 wt % in deionized water has a viscosity at 37° C. of 2 centistokes (cSt) or greater. In an embodiment, the aqueous carrier, containing the antimicrobial synthetic cationic poly peptide(s) at 2 wt %, has a viscosity at 37° C. that is greater than that of the aqueous carrier containing albumin at 2 wt % in place of the antimicrobial synthetic cationic polypeptide(s). In an embodiment, the aqueous carrier, containing the antimicrobial synthetic cationic polypeptide(s) at 2 wt %, has a viscosity at 37° C. that is at least about 20% greater than that of the aqueous carrier containing albumin at 2 wt % in place of the antimicrobial synthetic cationic polypeptide(s). In an embodiment, the aqueous carrier, containing the antimicrobial synthetic cationic polypeptide(s) at 2 wt %, has a viscosity at 37° C. that is at least about 50% greater than that of the aqueous carrier containing albumin at 2 wt % in place of the antimicrobial synthetic cationic polypeptide(s). In an embodiment, the aqueous carrier, containing the antimicrobial synthetic cationic polypeptide(s) at 2 wt %, has a viscosity at 37° C. that is at least about 100% greater than that of the aqueous carrier containing albumin at 2 wt % in place of the antimicrobial synthetic cationic polypeptide(s). In an embodiment, the antimicrobial pharmaceutical composition has a low toxicity after being infused into the peritoneal cavity of a plurality of healthy, young adult mice at a dose of 10 mL/kg, as measured by a mouse survival rate of 50% or greater at 72 hours.

Another embodiment provides a method of preventing microbial contamination of tissues other than intact, healthy skin, comprising: identifying a mammalian subject having a tissue site other than intact, healthy skin that is at risk of microbial contamination; and administering an antimicrobial pharmaceutical composition as described herein to the site in an amount effective to at least partially protect the tissue site from becoming contaminated with microbes.

Another embodiment provides a method of reducing microbial load in or on tissues other than intact, healthy skin, comprising: identifying a mammalian subject having a tissue site other than intact, healthy skin that has a microbial load; and administering an antimicrobial pharmaceutical composition as described herein to the tissue site in an amount effective to at least partially reduce the microbial load.

These and other embodiments are described in greater detail below.

BRIEF DESCRIPTION OF THE DRAWINGS

FIG. 1. Schematic illustration of synthetic cationic polypeptide(s) with various amino acid sequence arrangements. Certain arrangements may be referred to as blocks or segments.

FIG. 2. Synthetic cationic polypeptide(s) categorized into three groups based on cationic segment lengths (number of amino acid units).

FIG. 3. Examples of synthetic cationic polypeptide(s) categorized into groups (I) Long Cationic Segment (≥200 units) Polypeptide(s), (II) Medium Cationic Segment (100 to 199 units) Polypeptide(s), and (III) Short Cationic Segment (10-99 units) Polypeptide(s). The cationic segment contains a plurality of cationic amino acid units, but need not be composed entirely of cationic amino acid units. The hydrophobic segment contains a plurality of hydrophobic amino acid units, but need not be composed entirely of hydrophobic amino acid units.

FIG. 4. Example synthetic cationic polypeptide(s) with cationic-hydrophobic block sequence arrangement based on lysine and enantiopure L-leucine amino acid units. The average overall chain length of the polypeptide preparation is approximately 160 amino acid units. The lysine to leucine ratio, or K:L ratio, was found to be 3.2. The synthetic cationic polypeptide is designated KL-160/3.2. Analysis with size-exclusion chromatography displays two overlapping curves based on two injections. Dispersity (Đ)=weight-average molar mass (Mw)/number-average molar mass (Mn).

FIG. 6. Summary of multiple antimicrobial time-kill assays with synthetic cationic polypeptide(s) KL-160/3.2 against a variety of microbes. 60 minute time-kill assays performed with synthetic cationic polypeptide concentration of 100 µg/mL (Lot BAC003). The term "100%" CFU reduction indicates that no microbes were detected. MDR=multidrug-resistant; ESBL=extended spectrum β-lactamase; KPC=K. pneumoniae carbapenemase. Bold=Center for Disease Control (CDC) "Biggest Threats"; *Clinical isolates, R.M. Alden Research Laboratory.

FIG. 9. Summary of multiple antimicrobial time-kill assays with synthetic cationic polypeptide(s) KrL-100/5.7 against a variety of microbes. 60 minute time-kill assays performed with synthetic cationic polypeptide concentration of 100 μg/mL (Lot BAC002). The term "100%" CFU reduction indicates that no microbes were detected. MDR=multidrug-resistant; ESBL=extended spectrum β-lactamase; KPC=*K. pneumoniae* carbapenemase. Bold=Center for Disease Control (CDC) "Biggest Threats"; *Clinical isolates, R.M. Alden Research Laboratory.

FIG. 11. Critical Aggregation Concentration (CAC) of various synthetic cationic polypeptide(s) as measured by pyrene fluorescence method.

FIG. 14. Kinematic viscosity of synthetic cationic polypeptide(s) with a lysine-L-leucine block sequence arrangement (KL) in water at 0.5 wt % and measured using glass capillary viscometers (Ubbelohde viscometers) at a temperature of 37° C.

FIG. 15. Kinematic viscosity of various synthetic cationic polypeptides with a lysine-L-leucine (KL) and lysine-D,L-leucine (KrL) block sequence arrangement in water at 1 wt % and 2 wt % and measured using glass capillary viscometers (Ubbelohde viscometers) at a temperature of 40° C.

FIGS. 17A-D. Example synthetic cationic polypeptide(s) KL-120/2.5 forms viscous solutions and hydrogels in water. KL-120/2.5 prepared in DI water at concentrations of 0.5 wt %, 1.0 wt %, 1.5 wt %, 2.0 wt %, and 3.0 wt % and assessed for gel formation by tilt tube assay, firmness by texture analysis, and viscosity. (a) Visual gelation study by tilt tube assay. (b) Concentration-dependent firmness in water as measured by texture analysis. Firmness values were taken at a probe depth of 8 mm. Inset picture depicts 2 wt % KL-120/2.5 in water applied to an artificial skin substrate (VITRO-SKIN; IMS Inc.). (c) Graphical representation showing change in physical properties with increasing concentration of KL-120/2.5 (white=fluid; black=firm gel); based on data from viscometry for 0.5 wt % and 1.0 wt % and data from texture analysis and from tilt tube assay for the higher concentrations. (d) KL-120/2.5 at 1.5 wt % in water resists penetration by two different stainless steel spheres (BBs).

FIG. 20. Kinematic viscosity of two example synthetic cationic polypeptide(s) with a lysine-L-leucine (KL) and lysine-D,L-leucine (KrL) block sequence arrangement prepared in water at 1 wt % in water alone, 0.9% saline, or 4.4% aqueous xylitol. Measured using glass capillary viscometers (Ubbelohde viscometers) at a temperature of 40° C.

FIG. 23. Surface tension of various preparations of synthetic cationic polypeptide(s) in water. Samples were prepared at 0.1 mM and assessed using TA.XT2 Texture Analyzer with a 500 g load cell, 5 cm diameter Du Nouy ring and probe speed of 0.2 mm/s at room temperature.

FIGS. 27A-B. Emulsification properties. Example synthetic cationic polypeptide(s) KrL-100/5.0 and KrL-160/3.2 in water form stable emulsions when mixed with soybean oil. (a) Photo of assay demonstrating emulsion/liquid interfaces (white arrows); b) Emulsion index ($E_{24}$; % emulsion at 24 hours).

FIG. 28. Emulsification properties in water, saline, and xylitol. Example synthetic cationic polypeptide(s) KrL-110/4.0 (Lot D-301-37-05) and KL-100/5.7 (Lot D-301-67-03) prepared in water, saline (0.9%), or xylitol (4.4%) form stable emulsions when mixed with soybean oil.

FIG. 29. Evaluation of rabbit dermal irritation model results. Negligible responses to intact and abraded skin were observed following application of various formulations and concentrations of synthetic cationic polypeptide(s) KL-140/2.5 or KrL-120/5.0. Each rabbit (New Zealand White, N=3 per test article) had a total of 8 sites: 2 intact control, 2 intact test article, 2 sites abraded control, and 2 sites abraded test article. Each site was approximately 2.5×2.5 cm and received 0.5 mL test article for 24 h. Sites were scored at 1 h, 24 h, 48 h, and 72 h for erythema, edema, and eschar formation.

FIG. 30. Evaluation of guinea pig dermal sensitization results. No visible changes were observed following application of KL-140/2.5 (lot 73) or KrL-120/5.0 (lot 93) at 1 wt % in water. Hartley Albino Guinea Pigs (n=11 for test groups, n=6 for positive control, n=6 for negative control) were exposed to 0.3 mL of test article 6 h/day for 3 consecutive days per week for 3 weeks. Challenge exposures were conducted at 14+/−1 day after last induction exposure. Dose sites were scored at 24 and 48 h after removal of challenge patch.

FIG. 31. Evaluation of rat oral toxicity results. No abnormalities noted following administration of KL-140/2.5 in water or KrL-120/5.0 in water to rats at doses ranging from 0.625 mg/kg to 160 mg/kg by oral gavage. 2 mL were administered per male, young Sprague Dawley rat (N=5 per group). Clinical observations were performed for three days.

FIG. 34. Evaluation of mouse systemic toxicity after intraperitoneal administration. CD-1 mice received intraperitoneal injection of 40 mL/kg of water or KrL-120/5.0 Lot 93 or Lot 94 diluted in water at various concentrations. Final doses per animal ranged from 50 mg/kg to 800 mg/kg. N=5 CD-1 mice per group. Clinical observations were performed for three days.

FIG. 35. Evaluation of mouse systemic toxicity after intraperitoneal administration. CD-1 mice received intraperitoneal injection of 40 mL/kg of water or KL-170/3.3 or KL-140/2.5 diluted in water at various concentrations. Final doses per animal ranged from 6.25 mg/kg to 400 mg/kg. N=5 CD-1 mice per group. Clinical observations were performed for three days.

FIG. 36. Evaluation of mouse systemic toxicity after intraperitoneal administration. CD-1 mice received intraperitoneal injection of 40 mL/kg of water or KL-140/2.5 in various formulations and concentrations. Final doses per animal ranged from 1.25 mg/kg to 400 mg/kg. N=5 CD-1 mice per group. Clinical observations were performed for three days.

FIG. 37. Evaluation of mouse systemic toxicity after intraperitoneal administration. CD-1 mice received intraperitoneal injection of 40 mL/kg of water or KrL-120/5.0 in various formulations and at multiple concentrations. Final doses per animal ranged from 50 mg/kg to 800 mg/kg. N=5 CD-1 mice per group. Clinical observations were performed for three days.

FIGS. 63A-B. Results of post-microbial inoculation treatment in rodent closed wound model with surgical mesh. (a) Histopathology of tissue biopsies and mesh with $P.$ $aeruginosa$ inoculation. Samples were processed for histology and were stained with H&E. (b) Inflammation scores were determined by microscopic analysis by an experienced veterinary pathologist.

DETAILED DESCRIPTION

Definitions

Figure 5:
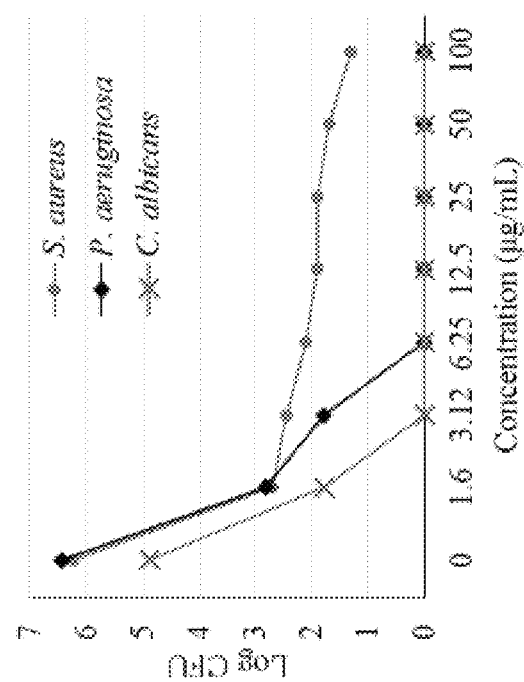
FIG. 5. Antimicrobial assay of example group 2 (Medium Cationic Segment) synthetic cationic polypeptide(s) with a lysine-enantiopure leucine block architecture and overall chain length of approximately 160 with a K:L ratio of 3.2. The synthetic cationic polypeptide is designated KL-160/3.2. Sixty minute in vitro time-kill assays were used to determine microbicidal activity (log CFU reduction) against S. aureus (ATCC 6538), P. aeruginosa (ATCC 27853), and C. albicans (ATCC 24433) at different sample concentrations from 1.6 µg/mL to 100 µg/mL (Lot BAC003).

As used herein in the context of describing antimicrobial synthetic cationic polypeptides, the term "antimicrobial" has its usual meaning as understood by those skilled in the art and thus includes a polypeptide that exhibits microbicidal activity as determined by a 60 minute time-kill assay against at least one bacteria selected from the group consisting of *S. aureus, S. epidermidis, P. aeruginosa*, and *E. coli*.

As used herein in the context of describing antimicrobial synthetic cationic polypeptides, the term "polypeptide" has its usual meaning as understood by those skilled in the art and thus includes a polymer that comprises two or more amino acid recurring units (also referred to as amino acid residues, or more simply units or residues) linked together by peptide bonds. A copolypeptide is a type of polypeptide that comprises two or more different amino acid recurring units. Molecular weights of polymers are weight average as determined by size exclusion chromatography (SEC) with molecular weight standards or using light scattering detection.

The term "block" or "blocky" copolypeptide has its usual meaning as understood by those skilled in the art and thus includes a sequence arrangement of amino acid units that includes a segment ("block") or segments that is at least 10 amino acid units in length in which the copolypeptide is relatively enriched in one or more of the amino acid units as compared to overall composition of the copolypeptide. In general, synthetic block copolypeptides have a sequence arrangement that reflects deliberate control over the copolymerization process. Likewise, the term "random" copolypeptide has its usual meaning as understood by those skilled in the art and thus includes a sequence arrangement of amino acid units that is a statistical distribution reflecting the concentration of the corresponding amino acid monomers in the polymerization mixture.

As used herein in the context of describing antimicrobial synthetic cationic block copolypeptides, the term "hydrophobic" block has its usual meaning as understood by those skilled in the art and thus includes a sequence arrangement in which a block or segment contains a plurality of hydrophobic amino acid units. Examples of hydrophobic amino acid units are known to those skilled in the art and include glycine (G), leucine (L), isoleucine (I), valine (V), proline (P), tryptophan (W), cysteine (C), methionine (M), phenylalanine (F) and alanine (A). Likewise, the term "hydrophilic" block has its usual meaning as understood by those skilled in the art and thus includes a sequence arrangement in which a block or segment contains a plurality of hydrophilic amino acid units. Examples of hydrophilic amino acid units are known to those skilled in the art and include serine (S), threonine (T), aspartic acid (D) and glutamic acid (E), as well as the positively charged amino acids lysine (K), arginine (R), histidine (H) and ornithine (O).

As used herein in the context of describing antimicrobial synthetic cationic polypeptides, the terms "positively charged" and "cationic" have their usual meanings as understood by those skilled in the art and thus includes an amino acid unit or a polypeptide that is positively charged at neutral pH. Examples of amino acid units that are positively charged at neutral pH include lysine, arginine, histidine and ornithine, and thus the presence of one or more of these positively charged units in the polypeptide (in an amount in excess of any anionic units) can render the polypeptide cationic.

As used herein in the context of describing a sterilized antimicrobial pharmaceutical composition, the term "sterilized" has its usual meaning as understood by those skilled in the art and thus includes a composition that has been subjected to a sterilization process or processes that has the effect of ensuring the absence or reduction of known pathogens in the composition to a degree that renders the sterilized composition clinically acceptable for local administration to a body orifice (such as intranasal administration) or to open skin such as administration to an open wound such as a surgical site. Non-limiting examples of such sterilization processes include heat sterilization (e.g., autoclaving), sterile filtration, irradiation, and/or treatment by chemical agents such as ethylene oxide.

As used herein in the context of describing a self-assembling polypeptide, the term "self-assembling" has its usual meaning as understood by those skilled in the art and thus includes configurations of the polypeptides when dispersed in a medium (such as the other ingredients of a pharmaceutical composition) in which intermolecular attractive forces between certain segments or blocks of the polypeptide causes those segments or blocks to loosely bind to one another. For example, as noted in U.S. Pat. No. 9,017,730, self-assembly of block cationic copolypeptides was observed in aqueous solution, resulting in various hierarchical structures that depended on the configuration of the hydrophobic domains and their effect on attractive intermolecular interactions between the polymer chains. In contrast, U.S. Pat. No. 9,017,730 indicates that random copolypeptides did not exhibit self-assembly. Those skilled in the art are aware of various techniques for determining whether a synthetic cationic polypeptide is self-assembling (see, e.g., U.S. Pat. No. 9,017,730). As compared to an otherwise comparable synthetic cationic polypeptide that exhibits random arrangements in dilute solution and does not exhibit self-assembly, a self-assembling synthetic cationic polypeptide generally exhibits a higher viscosity.

As used herein in the context of describing a molecular feature or parameter that promotes self-assembly of polypeptides, terms such as "promotes" and "promoting" have their usual meaning as understood by those skilled in the art and thus include allowing or enhancing such self-assembly. For example, U.S. Pat. Nos. 9,017,730 and 9,446,090 describe various sequence arrangements of hydrophobic amino acid units and hydrophilic amino acid units that are configured to promote self-assembly of a copolypeptide in water. Similarly, a sterilization technique that is configured to produce a sterilization state that promotes self-assembly of a polypeptide is one that allows for self-assembly or enhances self-assembly when applied to such a polypeptide or to a composition of a polypeptide that is dispersed within an aqueous carrier. Likewise, a composition of an aqueous carrier that is selected to promote self-assembly of a polypeptide is one that allows for self-assembly or enhances self-assembly when such a polypeptide is dispersed within the aqueous carrier.

As used herein in the context of describing a self-assembling synthetic cationic block copolypeptide in comparison to an otherwise comparable random synthetic cationic copolypeptide, the term "otherwise comparable random synthetic cationic copolypeptide" has its usual meaning as understood by those skilled in the art and thus includes copolypeptides that have approximately the same molecular weight and relative numbers of the same hydrophobic and hydrophilic amino acid recurring units as the self-assembling synthetic cationic block copolypeptide, except the sequence arrangement of those amino acid recurring units in the comparable copolypeptide is random rather than block. For example, with respect to a self-assembling block copolypeptide having a hydrophilic (positively charged) lysine block with an average length of about 120 units and a hydrophobic leucine block with an average length of about 30 units, an otherwise comparable random synthetic cationic copolypeptide is one containing an average of about 120 lysine units and about 30 leucine units per copolypeptide chain except that the sequence arrangement of those units along the chain of the random copolypeptide is a statistical distribution reflecting the concentration of the lysine and leucine monomers in the polymerization mixture.

As used herein in the context of describing the administration of a sterilized antimicrobial pharmaceutical composition to a site on a mammalian body in an abundant amount effective to at least partially prevent and/or treat an infection, the terms "abundant" and "abundance" have their usual meaning as understood by those skilled in the art and thus include the administration of amounts of the copolypeptide that are at least 10 times greater than the dosage needed to achieve the desired prevention and/or treatment effect. Typically, a total treatment dose of antimicrobial pharmaceutical composition that includes the administration of 1 g of synthetic cationic polypeptide(s) or more for a 70 kg person, which represents 14.3 mg/kg, is considered to be an abundant administration. Those skilled in the art recognize that biologically active compounds are generally administered in a "therapeutic window" that includes a range of doses over which a desired therapeutic response is achieved without causing significant adverse effects in the subjects to which they are administered. This dosage range is generally between the minimum effective concentration (MEC) and the minimum toxic concentration (MTC) and is typically determined in advance for each biologically active compound, and communicated to the subject and/or caregiver in the form of a dosage recommendation. However, in some situations, such as topical application of an antimicrobial composition to bodily orifices and/or open wounds of mammalian subjects, it may be impractical to determine the MEC and thus highly advantageous to have the flexibility to administer the antimicrobial in abundance. For example, when treating an open wound in an emergency setting where time may be of the essence, it is highly advantageous for a caregiver to have the flexibility to apply the antimicrobial to the open wound in abundance (e.g., in an amount at least ten times greater than the MEC) without being concerned about administering an amount that exceeds the MTC. The MEC for a particular sterilized antimicrobial pharmaceutical composition can be determined by methods known to those skilled in the art, such as those described in the examples below (e.g., amount effective to achieve 3-log CFU killing in an in vitro time-kill assay).

As used herein in the context of describing an antimicrobial pharmaceutical compositions that comprise or consist of an aqueous carrier and an antimicrobial synthetic cationic polypeptide(s) that is dispersed in the aqueous carrier, the term "aqueous carrier" has its usual meaning as understood by those skilled in the art and thus includes various water-based carrier systems that can optionally contain a dispersed substance such as an ionic additive (e.g., a salt) or a non-ionic additive (e.g., polymer, alcohol, sugar and/or surfactant). Substances that are dispersed in the aqueous carrier may be dissolved therein and/or dispersed in the form of small particles.

Antimicrobial Pharmaceutical Compositions

Various embodiments provide antimicrobial pharmaceutical compositions that comprise or consist of an aqueous carrier and an antimicrobial synthetic cationic polypeptide(s) dispersed in the aqueous carrier. The amount of cationic polypeptide(s) dispersed in the aqueous carrier can vary over a broad range that depends primarily on the desired viscosity of the antimicrobial pharmaceutical composition. For example, in various embodiments the amount of synthetic cationic polypeptide(s) in the antimicrobial pharmaceutical composition is in the range of about 0.001% to about 10%, by weight based on total weight of the antimicrobial pharmaceutical composition. In some embodiments the amount of synthetic cationic polypeptide(s) dispersed in the aqueous carrier is in the range of about 0.01% to about 5%, by weight based on total weight of the antimicrobial pharmaceutical composition.

In various embodiments the antimicrobial synthetic cationic polypeptide(s) that is dispersed in the aqueous carrier comprises a plurality of positively charged amino acid units (at neutral pH). In an embodiment, the synthetic cationic polypeptide(s) comprises at least 40 amino acid units, of which at least some are positively charged. In an embodiment, the number of positively charged amino acid units in the synthetic cationic polypeptide(s) is at least 10, at least 15, or at least 20. Lysine, arginine, histidine and combinations thereof are examples of suitable amino acid units that are positively charged at neutral pH. In an embodiment, the plurality of positively charged amino acid units in the synthetic cationic polypeptide(s) comprises positively charged lysine units.

In various embodiments, the antimicrobial synthetic cationic polypeptide(s) has a viscosity of 2 centistokes (cSt) or greater, as measured at a concentration of 2 wt % in deionized water and at a temperature of 37° C. Suitable synthetic cationic polypeptide(s) having a range of higher and lower viscosities (e.g., from about 1.5 cSt to about 16,000 cSt, or about 2.0 cSt to about 16,000 cSt) can be made by adjusting the molecular weight of the polypeptide, the level of positively charged amino acid units, and/or the degree to which the polypeptide self-assembles. In an embodiment, the antimicrobial synthetic cationic polypeptide(s) has a viscosity that is greater than that of bovine serum albumin, as measured at a concentration of 2 wt % in deionized water and at a temperature of 37° C.

Antimicrobial synthetic cationic polypeptide(s) can be copolypeptides that comprise other monomer units in addition to the positively charged amino acid units. For example, in various embodiments the antimicrobial synthetic cationic polypeptide(s) may further comprise a plurality of hydrophobic amino acid units. In various embodiments, the number of hydrophobic amino acid units in the cationic copolypeptide is at least 5, at least 10, or at least 15. Examples of suitable hydrophobic amino acid units include leucine (L), isoleucine (1), valine (V), phenylalanine (F), alanine (A), and combinations thereof. In an embodiment, the plurality of hydrophobic amino acid units in the synthetic cationic polypeptide(s) comprises leucine units.

The sequence arrangement of amino acid units in the synthetic cationic polypeptide(s) can be random, blocky or a combination thereof. For example, in an embodiment, the sequence arrangement of hydrophobic amino acid units and positively charged amino acid units in the synthetic cationic polypeptide(s) is blocky. In a number of embodiments, such a block copolypeptide can comprise various hydrophobic and hydrophilic amino acid units. For example, in an embodiment, the synthetic cationic polypeptide(s) is a block copolypeptide that comprises hydrophobic leucine units and positively charged lysine units.

In various embodiments, the antimicrobial synthetic cationic polypeptide(s) self-assembles into multimeric structures in water and other aqueous carriers. Examples of multimeric structures include micelles, sheets, vesicles, and fibrils (see U.S. Pat. No. 9,017,730). In an embodiment, the antimicrobial synthetic cationic polypeptide(s), in deionized water at 37° C. at a concentration of 3 wt %, forms a self-supporting hydrogel. In an embodiment, the antimicrobial synthetic cationic polypeptide(s) displays surfactant activity in deionized water at 37° C., as measured by a decrease in surface tension of at least 10% or at least 20% as compared to deionized water alone. In an embodiment, self-assembly of an antimicrobial synthetic cationic polypeptide(s) is evidenced by a critical aggregation concentration for the polypeptide that is below 1000 μg/mL at 37° C. in deionized water. In an embodiment, self-assembly of an antimicrobial synthetic cationic polypeptide(s) is evidenced by a critical aggregation concentration for the polypeptide that is below 100 μg/mL at 37° C. in deionized water.

Self-assembly of the antimicrobial synthetic cationic polypeptide(s) can be controlled in various ways. For example, in an embodiment, the antimicrobial synthetic cationic polypeptide(s) comprises a sequence arrangement of hydrophobic amino acid units and positively charged amino acid units that is configured to promote self-assembly of the antimicrobial synthetic cationic polypeptide(s) into multimeric structures. For example, self-assembly of the polypeptide is enhanced by a blocky sequence arrangement of hydrophobic amino acid units and positively charged amino acid units. A higher hydrophobic amino acid unit content and/or longer blocks of hydrophobic amino acid units in the polypeptide tend to enhance self-assembly in aqueous carriers.

The antimicrobial synthetic cationic polypeptide(s) described herein can be dispersed in an aqueous carrier to form antimicrobial pharmaceutical compositions. In various embodiments the aqueous carrier is water. In other embodiments the aqueous carrier is an aqueous solution that comprises a pharmaceutically acceptable salt, a non-ionic additive(s), or a combination thereof. Salt tends to inhibit self-assembly of the polypeptide and thus excessive salt is to be avoided. Normal saline, half normal saline, quarter normal saline and phosphate buffered saline are examples of suitable aqueous carriers that contain a pharmaceutically acceptable salt. In an embodiment, the aqueous carrier comprises sodium chloride. In various embodiments, the aqueous carrier is an aqueous solution that comprises a non-ionic additive. Examples of suitable non-ionic additives include dextrose, mannitol, glycerol, xylitol, sorbitol, surfactant(s), and combinations thereof.

The aqueous carrier can comprise various amounts of an additive, such as a pharmaceutically acceptable salt, a non-ionic additive(s), or a combination thereof. In various embodiments, the aqueous carrier comprises an amount of a pharmaceutically acceptable salt that is 9.0 g/L or less; or 8.0 g/L or less; or 7.0 g/L or less; or 6.0 g/L or less; or 5.0 g/L or less; or 4.5 g/L or less; or 4.0 g/L or less; or 3.0 g/L or less. In an embodiment, the amount of additive(s) in the aqueous carrier is selected to control the viscosity of the antimicrobial pharmaceutical composition. In an embodiment, the aqueous carrier comprises an additive in an amount that increases the viscosity of the antimicrobial pharmaceutical composition. In an embodiment, the aqueous carrier comprises an additive in an amount that decreases the viscosity of the antimicrobial pharmaceutical composition. In an embodiment, the non-ionic additive(s) is present in an amount effective to increase the osmotic concentration of the antimicrobial pharmaceutical composition to a value that is at least 10% greater than that of the antimicrobial pharmaceutical composition without said additive(s). In various embodiments the concentration of the additive in the antimicrobial pharmaceutical composition is in the range of about 0.1 wt % to about 10 wt %, based on total weight. In various embodiments the concentration of the non-ionic additive in the antimicrobial pharmaceutical composition is in the range of about 0.01 wt % to about 2 wt %, or in the range of about 0.05 wt % to about 5 wt %, based on total weight.

In various embodiments, an antimicrobial pharmaceutical composition as described herein is sterilized by a sterilization technique(s) configured to achieve a sterilized antimicrobial pharmaceutical composition. In an embodiment, the sterilization technique(s) is configured to have minimal impact on the chemical structure of the synthetic cationic polypeptide and/or the tendency for the synthetic cationic polypeptide to self-assemble. Examples of such sterilization techniques are illustrated in FIGS. 42-52. In an embodiment, an antimicrobial pharmaceutical composition as described herein is sterilized by a sterilization technique(s) configured to achieve a sterilized antimicrobial pharmaceutical composition with the antimicrobial synthetic cationic polypeptide(s) having a weight average molecular weight and/or a dispersity comparable to (e.g., within about 10%) that of the antimicrobial synthetic cationic polypeptide(s) of the antimicrobial pharmaceutical composition without sterilization by said sterilization technique(s). In an embodiment, the antimicrobial pharmaceutical composition is sterilized by a sterilization technique(s) configured to achieve a sterilized antimicrobial pharmaceutical composition having a viscosity level at 37° C. that is comparable to that of the antimicrobial pharmaceutical composition without sterilization by this sterilization technique(s). In an embodiment, the viscosity of the sterilized antimicrobial pharmaceutical composition at 37° C. is in the range of 20% to 200% of the viscosity of an otherwise comparable unsterilized antimicrobial pharmaceutical composition.

In an embodiment, the antimicrobial pharmaceutical composition has a low toxicity after being infused into the peritoneal cavity of a plurality of mice at a dose of 10 mL/kg, as measured by a mouse survival rate of 50% or greater at 72 hours after being infused. In an embodiment, the antimicrobial pharmaceutical composition has a low toxicity after being infused into the peritoneal cavity of a plurality of mice at a dose of 20 mL/kg, as measured by a mouse survival rate of 50% or greater at 72 hours after being infused. In an embodiment, the antimicrobial pharmaceutical composition has a low toxicity after being infused into the peritoneal cavity of a plurality of mice at a dose of 40 mL/kg, as measured by a mouse survival rate of 50% or greater at 72 hours after being infused. In an embodiment, the antimicrobial pharmaceutical composition has a microbiocidal activity that is comparable to that of the otherwise comparable unsterilized antimicrobial pharmaceutical composition, wherein the microbiocidal activity is determined by a 60 minute time-kill assay against at least one bacteria selected from the group consisting of *S. aureus, S. epidermidis, P. aeruginosa*, and *E. coli*.

The inclusion of other active pharmaceutical ingredients to the antimicrobial pharmaceutical compositions described herein may enhance antimicrobial performance and/or decrease the risk of toxicities, both local and systemic. In particular, the inclusion of other antimicrobial agents, including antibiotics, antiseptics, iodine compounds, and/or silver compounds, may act cooperatively with the synthetic cationic polypeptide(s) to help prevent and/or treat infection. Further, the inclusion of one or more anti-inflammatory agents may enhance performance and/or decrease the risk of toxicities, both local and systemic. Local inflammation may contribute to pathogenesis of various disease settings that also involve microbial contamination or infection. Examples include otitis externa, chronic sinusitis, pulmonary conditions, and certain wound conditions. Such conditions could be treated by a combination of synthetic cationic polypeptide(s) and anti-inflammatory agents, such as corticosteroids, anti-histamines, and/or anti-cytokines. As such, including anti-inflammatory agents in an antimicrobial composition containing synthetic cationic polypeptide(s) may provide benefits.

In an embodiment, the antimicrobial pharmaceutical composition comprises an anti-inflammatory compound. For example, in an embodiment, the inflammatory compound is selected from the group consisting of a corticosteroid, a histamine inhibitor and a cytokine inhibitor. Examples of corticosteroids include betamethasone dipropionate, clobetasol propionate, diflorasone diacetate, fluocinonide, and halobetasol propionate. Examples of histamine inhibitors include those that inhibit the histamine H1, H2, H3 and H4 receptors. Examples of cytokine inhibitors include glucocorticoids and pentoxifylline.

The antimicrobial pharmaceutical compositions described herein can be made in various ways. In an embodiment, the antimicrobial synthetic cationic polypeptide is made in the manners taught in U.S. Pat. Nos. 9,017,730 and/or 9,446,090, which are expressly incorporated herein by reference for all purposes including the teaching of such methods for making cationic polypeptides. The antimicrobial pharmaceutical composition can be made combining the antimicrobial synthetic cationic polypeptide with the aqueous carrier to thereby disperse (e.g., dissolve) the polypeptide in the aqueous carrier. For example, such combining can be accomplished by mixing the ingredients (cationic polypeptide(s), aqueous carrier and optional ingredients such as inflammatory compound) with agitation at a temperature in the range of about 20° C. to 90° C., for a length of time that is effective to disperse (e.g., dissolve) the polypeptide. The ingredients can be mixed together in any order, although those skilled in the art may prefer a particular order in individual cases.

Methods of Preventing Microbial Contamination

Various embodiments provide methods of preventing microbial contamination of tissues that are particularly suitable for tissue that is other than intact, healthy skin. For example, in an embodiment such a method comprises identifying a mammalian subject having a tissue site other than intact, healthy skin that is at risk of microbial contamination. Examples of such tissue sites include diseased skin, a surgical site, a traumatic wound, debrided tissues, peritoneal cavity, a pulmonary airway, a sinus, and urinary tract. In an embodiment, the method comprises administering an antimicrobial pharmaceutical composition as described herein to the tissue site in an amount effective to at least partially protect the tissue site from becoming contaminated with microbes. For example, in some embodiments the method at least partially protects the tissue site from becoming infected with at least one bacteria selected from the group consisting of *S. aureus, S. epidermidis, P. aeruginosa,* and *E. coli.* The method may further comprise sampling the tissue site to assess the microbial load, e.g., the load of at least one bacteria selected from the group consisting of *S. aureus, S. epidermidis, P. aeruginosa,* and *E. coli.* In an embodiment, the antimicrobial pharmaceutical composition is administered intraoperatively to a surgical site. Administration of the antimicrobial pharmaceutical composition to the tissue site can be accomplished by direct topical application.

Amounts of the antimicrobial pharmaceutical composition that are effective to at least partially protect the tissue site from becoming contaminated with microbes may be determined by those skilled in the art using routine experimentation informed by the guidance provided herein. In various embodiments the antimicrobial pharmaceutical composition has a broad therapeutic window and thus a relatively wide range of doses is provided over which the desired protection from infection is achieved. In some embodiments, this broad therapeutic window facilitates administration of the antimicrobial pharmaceutical composition to the tissue site in abundance.

Methods of Reducing Microbial Load

Various embodiments provide methods of reducing microbial load in or on tissues that are particularly suitable for tissue that is other than intact, healthy skin. For example, in an embodiment such a method comprises identifying a mammalian subject having a tissue site other than intact, healthy skin that has a microbial load. Examples of such tissue sites include diseased skin, a surgical site, a traumatic wound, debrided tissues, peritoneal cavity, a pulmonary airway, a sinus, and urinary tract. In an embodiment, the tissue site is microbially contaminated, infected or both. In an embodiment, the method comprises administering an antimicrobial pharmaceutical composition as described herein to the tissue site in an amount effective to at least partially reduce the microbial load. For example, in some embodiments the method at least partially reduces the microbial load at the tissue site of least one bacteria selected from the group consisting of *S. aureus, S. epidermidis, P. aeruginosa,* and *E. coli.* The method may further comprise sampling the tissue site to assess the microbial load, e.g., the load of at least one bacteria selected from the group consisting of *S. aureus, S. epidermidis, P. aeruginosa,* and *E. coli.* In an embodiment, the antimicrobial pharmaceutical composition is administered intraoperatively to a tissue site that is microbially contaminated, infected or both.

Amounts of the antimicrobial pharmaceutical composition that are effective to at least partially reduce the microbial load may be determined by those skilled in the art using routine experimentation informed by the guidance provided herein. In various embodiments the antimicrobial pharmaceutical composition has a broad therapeutic window and thus a relatively wide range of doses is provided over which the desired reduction in microbial load is achieved. In some embodiments, this broad therapeutic window facilitates administration of the antimicrobial pharmaceutical composition to the tissue site in abundance. Administration of the antimicrobial pharmaceutical composition to the tissue site can be accomplished by direct topical application.

EXAMPLES

Synthetic cationic polypeptide(s) can be prepared with various amino acid sequence arrangements, some of which are illustrated schematically in FIG. 1. Certain arrangements may be referred to as blocks or segments. Typically, these would be stretches of amino acid units that contain a plurality of one type of amino acid (e.g., cationic, anionic, hydrophobic). The synthetic cationic polypeptide(s) described herein were made in accordance with the synthetic methods described in U.S. Pat. No. 9,017,730 and in 9,446, 090, which are hereby incorporated herein by reference in its entirety and for all purposes, including for the purpose of describing synthetic cationic polypeptide(s) and methods of making them.

Cationic blocks have a plurality of positive charges at neutral pH and can vary substantially in length from about 10 amino acid units to well over 300 amino acid units. Positively charged amino acid units can be selected from lysine (K), arginine (R), histidine (H), and ornithine (O). Cationic blocks need not be composed entirely of cationic amino acids. In addition to the plurality of cationic amino acids, the block segment may also include other amino acids, including polar amino acids, such as serine (S) and threonine (T), which would help maintain hydrophilicity. A small percentage of negatively charged amino acids and/or hydrophobic amino acids may also be included in the cationic block, so long as there are more cationic units than anionic units in the block.

Hydrophobic blocks have a plurality of hydrophobic amino acids and can vary substantially in length, typically from about 5 amino acid units to about 60 amino acid units. Hydrophobic blocks can also display secondary structure (e.g., alpha helical vs. disordered). Hydrophobic amino acids are uncharged at pH 7.0. In addition, they have side chains composed mostly of carbon and hydrogen, have very small dipole moments, and tend to be repelled from water. Hydrophobic amino acid units can be selected from a list that includes glycine (G), alanine (A), valine (V), leucine (L), isoleucine (I), proline (P), phenylalanine (F), and methionine (M). Hydrophobic blocks need not be composed entirely of hydrophobic amino acid units. In addition to the plurality of hydrophobic amino acids, the block segment may also include other amino acids, including polar amino acids, such as serine (S) and threonine (T). A small percentage of charged amino acids may also be included in the hydrophobic block.

Synthetic cationic polypeptide(s) having a cationic-hydrophobic block architecture can be prepared with a wide range of overall chain lengths, typically in the range of about 20 amino acid units or fewer on the low side and about 400 amino acid units or more on the high side. As depicted in FIG. 2, in describing cationic polypeptides with a block architecture, they can be categorized into three groups: (I) Long Cationic Segment (>200 amino acid units); (II) Medium Cationic Segment (100-199 amino acid units); and (II) Short Cationic Segment (10-99 amino acid units). The ratio of cationic block length to hydrophobic block length can be varied over a wide range, typically from about 1.5 on the low side to about 15 or more on the high side. Mean molecular weights of these synthetic cationic polypeptide(s) can be varied over a wide range, typically from about 3,000 Da on the low side to about 70,000 Da or greater on the high side. FIG. 3 shows in greater detail the composition of such synthetic cationic polypeptide(s) with segmented architecture.

As described in greater detail below, we have synthesized and tested numerous different synthetic cationic polypeptide(s) with a block sequence arrangement. For comparison, we have also synthesized cationic polypeptides with a comparable amino acid composition, but lacking a block or segmented sequence arrangement. These synthetic cationic polypeptide(s) have been found to vary in multiple functional properties, including antimicrobial activity, hemostatic properties, barrier properties, and surfactant activities. Further, it has been demonstrated that both molecular design and formulation can affect these functional properties. Regarding molecular design features, we have observed that overall chain length and the ratio of cationic/hydrophilic block length to hydrophobic block length are characteristics that have high impact on functionality. Specific features within each block, including amino acid selection and enantiopurity, also contribute.

In the present application, we use a nomenclature based on two key characteristics of the synthetic cationic polypeptide(s): the overall chain length and the ratio of the cationic block length to the hydrophobic block length. By way of example, KL-140/2.5 has an approximate average chain length of 140 amino acid units and an approximate ratio of cationic segment to hydrophobic segment of 2.5. In this polymer, the cationic amino acid units are lysines (K) and the hydrophobic amino acid units are enantiopure L-leucines (L). As another example, KrL-100/5.7 has an approximate average chain length of 100 amino acid units and an approximate ratio of cationic segment to hydrophobic segment of 5.7. In this polymer, the cationic amino acid units are lysines (K) and the hydrophobic amino acid units are racemic D,L-leucines (rL). As another example RrL-75/2.8 has an approximate average chain length of 75 amino acid units. In this polymer, the cationic amino acids units are arginine (R) and the hydrophobic amino acid units are racemic D,L-leucines (rL).

Synthetic cationic polypeptide(s) that have been described (using a different nomenclature system) in U.S. Pat. Nos. 9,017,730 and 9,446,090 include $K_{55}$, $K_{55}L_5$, $K_{55}L_{10}$, $K_{55}L_{15}$, $K_{55}L_{20}$, $K_{55}L_{20}$-RAN, $K_{55}L_{25}$, $K_{55}L_{30}$, $K_{55}(raC-L)_5$, $K_{55}(raC-L)_5$-RAN, $K_{55}(raC-L)_{10}$, $K_{55}(raC-L)_{10}$-RAN, $K_{55}(raC-L)_{20}$, $R_{55}^H(raC-L)_{20}$, $K_{55}(raC-L)_{20}$-RAN, $K_{55}(rac-L)_{30}$, $K_{55}(raC-I)_{20}$, $K_{55}(rac-L/F)_{20}$, $K_{55}(rac-V)_{20}$, $K_{55}(rac-A)_{20}$, $[K_{65}(rac-L)_{15}$-RAN$](rac-L)_{20}$, $K_{80}$, $K_{80}(raC-L)_{20}$, $K_{90}(rac-L)_{30}$, $K_{90}(rac-L)_{30}$-RAN, $K_{99}L_{36}$, $K_{99}(rac-L)_{36}$, $K_{99}(rac-L)_{36}$-RAN, $K_{100}$, $K_{100}L_{20}$, $K_{100}L_{30}$, $K_{100}L_{40}$, $K_{100}L_{40}$-RAN, $K_{100}L_{50}$, $K_{100}L_{60}$, $K_{100}(rac-L)_{20}$, $K_{100}(rac-L)_{20}$-RAN, $K_{100}(rac-L)_{30}$, $K_{100}(rac-L)_{40}$, $K_{100}(rac-L)_{60}$, $K_{120}(rac-L)_{10}$, $K_{120}(rac-L)_{40}$, $K_{120}(rac-L)_{40}$-RAN, $K_{120}(rac-L)_{50}$, $K_{120}(rac-L)_{50}$-RAN, $K_{130}L_{20}$, $K_{130}L_{30}$, $K_{130}L_{40}$, $K_{130}L_{40}$-RAN, $K_{130}L_{60}$, $K_{130}(rac-L)_{20}$, $K_{130}(rac-L)_{30}$, $K_{130}(rac-L)_{40}$, $K_{130}(rac-L)_{60}$, $K_{150}L_{30}$, $K_{160}(rac-L)_{20}$, $K_{180}$, $K_{180}L_{18}$, $K_{180}L_{20}$, $K_{180}L_{36}$, $K_{180}L_{54}$, $K_{180}(rac-L)_{18}$, $K_{180}(rac-L)_{20}$, $K_{180}(raC-L)_{36}$, $K_{180}(raC-L)_{54}$, $K_{190}L_{10}$, $K_{200}L_{50}$, PEG205$(raC-L)_{20}$, $K_{256}$, $K_{324}L_{36}$, $K_{360}$ $K_{360}L_{36}$, $K_{360}L_{36}$-RAN, $K_{360}L_{54}$, $K_{360}L_{72}$, $K_{360}(rac-L)_{36}$, $K_{360}(rac-L)_{54}$, and $K_{360}(rac-L)_{72}$.

Example 1

Synthetic cationic polypeptide(s) can be designed to enable preparations with robust microbicidal activity and with barrier effects as illustrated in FIGS. 4-6. FIG. 4 describes an example synthetic cationic polypeptide with cationic-hydrophobic block sequence arrangement based on lysine and enantiopure L-leucine amino acid units. The average overall chain length of the polypeptide preparation is approximately 160 amino acid units; the lysine to leucine or K:L ratio was found to be 3.2. This synthetic cationic polypeptide is designated KL-160/3.2 and an SEC chromatogram of the polymer shows a single peak with a relatively low dispersity (Ð) of 1.1.

FIG. 5 depicts concentration-dependent antimicrobial activity of KL-160/3.2 in water. There is a clear concentration-dependent effect with activity against *S. aureus, P. aeruginosa,* and *C. albicans* at concentrations as low as 1.6 µg/mL. A summary of antimicrobial activity of KL-160/3.2 observed over multiple experiments is provided in FIG. 6. As noted below, KL-160/3.2 when prepared in water at higher concentrations (i.e., >2 wt %), forms self-supporting hydrogels. These properties of the synthetic cationic polypeptide(s) result in a desirable combination of antimicrobial activity and barrier function. It is important to recognize that the functional properties of these antimicrobial preparations are dependent on formulation (e.g., presence and concentration of additives), as well as on the presence, absence or extent of certain process and/or handling procedures, including methods of sterilization.

Example 2

Figure 7:
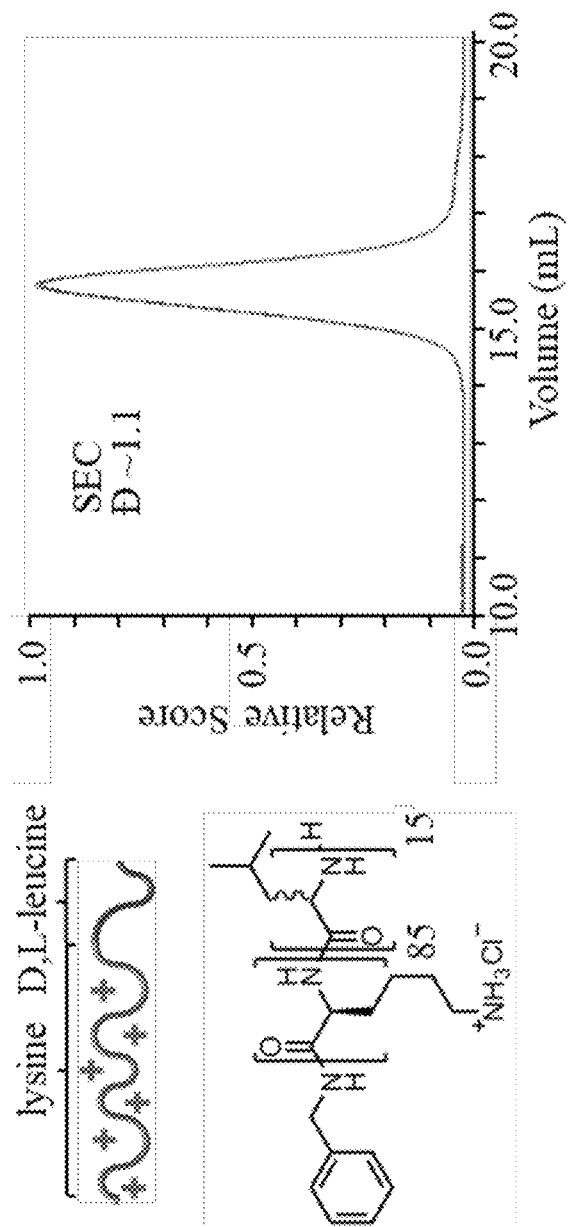
FIG. 7. Example synthetic cationic polypeptide(s) with cationic-hydrophobic block sequence arrangement based on lysine and racemic D,L-leucine amino acid units. The average overall chain length of the polypeptide preparation is approximately 100 amino acid units. The lysine to leucine ratio, or K:L ratio, was found to be 5.7. The synthetic cationic polypeptide is designated KrL-100/5.7. Analysis with size-exclusion chromatography displays two overlapping curves based on two injections. Dispersity (Đ)=weight-average molar mass (Mw)/number-average molar mass (Mn).
Figure 8:
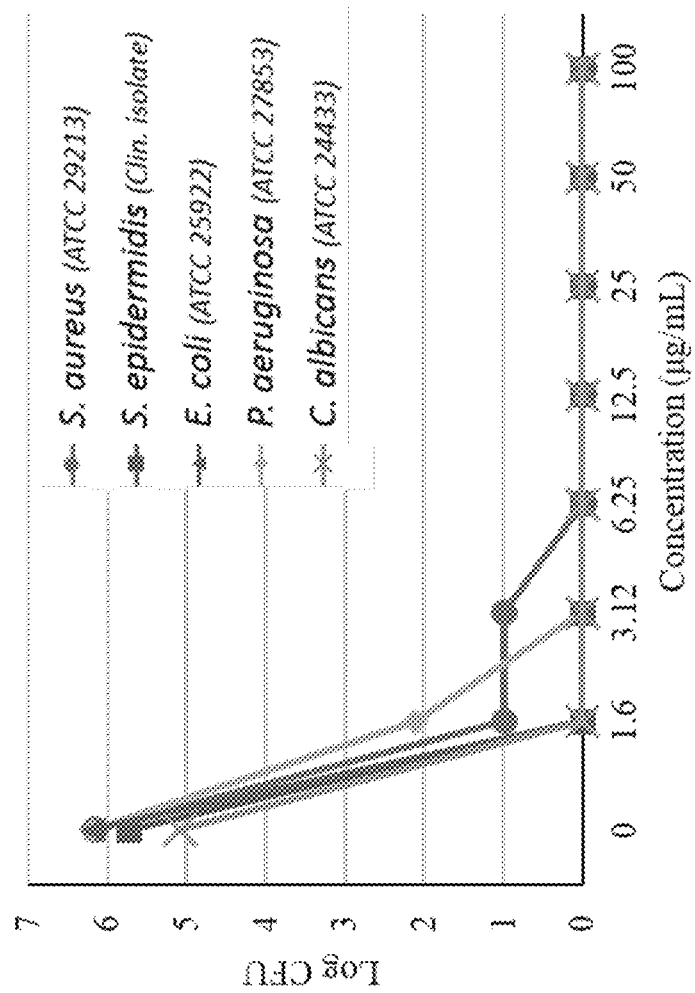
FIG. 8. Antimicrobial assay of example group 3 (Short Cationic Segment) synthetic cationic polypeptide(s) with a lysine-racemic leucine block architecture and overall chain length of approximately 100 with a K:(rac-L) ratio of 5.7. The molecule is designated KrL-100/5.7. Sixty minute in vitro time-kill assays were used to determine microbicidal activity (log CFU reduction) against key pathogens at different sample concentrations from 1.6 μg/mL to 100 μg/mL (Lot BAC002).

Synthetic cationic polypeptide(s) can be designed to enable preparations with robust microbicidal activity and with surfactant activity as illustrated in FIGS. 7-9. FIG. 7 describes an example synthetic cationic polypeptide with cationic-hydrophobic block sequence arrangement based on lysine and racemic D,L-leucine amino acid units. The average overall chain length of the polypeptide preparation is approximately 100 amino acid units; the lysine to racemic leucine or K:rL ratio was found to be 5.7. This synthetic cationic polypeptide is designated KrL-100/5.7 and an SEC chromatogram of the polymer shows a single peak with a relatively low dispersity (Đ) of 1.1.

FIG. 8 depicts concentration-dependent antimicrobial activity of KrL-100/5.7 in water. There is a clear concentration-dependent effect with activity against *S. aureus, S. epidermidis, E. coli, P. aeruginosa*, and *C. albicans* at concentrations as low as 1.6 µg/mL. A summary of antimicrobial activity of KrL-100/5.7 observed over multiple experiments is provided in FIG. 9. As noted below, KrL-100/5.7 when prepared in water demonstrates surfactant activities. These properties of the synthetic cationic polypeptide(s) result in a desirable combination of antimicrobial activity and surfactant function, which can enhance performance against biofilms and/or tissue debridement. It is important to recognize that the functional properties of these antimicrobial preparations are dependent on formulation (e.g., presence and concentration of additives), as well as on the presence, absence or extent of certain process and/or handling procedures, including methods of sterilization.

Example 3

Figure 10:
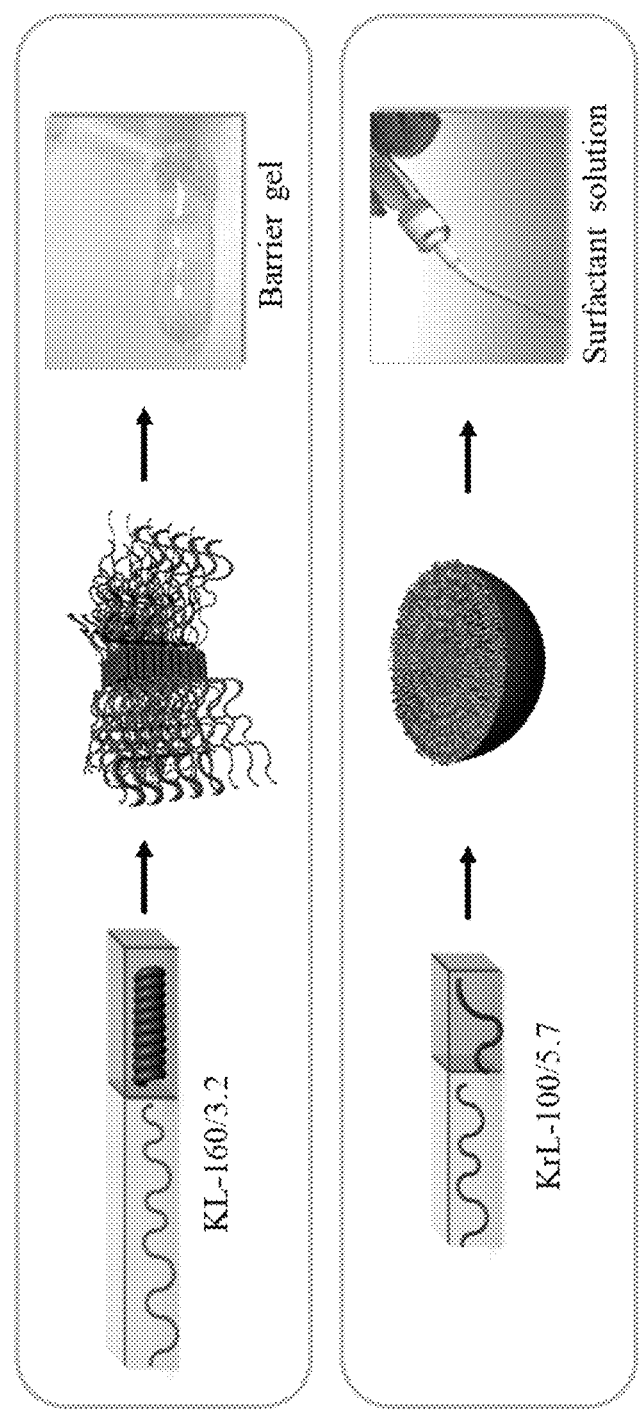
FIG. 10. Synthetic cationic polypeptide(s) with a block sequence arrangement can be designed and formulated to self-assemble into multimeric structures. Two examples are depicted here: KL-160/3.2 was designed to self-assemble into fibrillar structures and form barrier hydrogels and KrL-100/5.7 was designed to self-assemble into micellar structures and have surfactant properties.

Self-assembly of cationic antimicrobial peptides into multimeric complexes can be beneficial. Synthetic cationic polypeptides with a block sequence arrangement can be designed and formulated to self-assemble into multimeric structures. Two examples are depicted in FIG. 10: KL-160/3.2 was designed to self-assemble into fibrillar structures and form barrier hydrogels and KrL-100/5.7 was designed to self-assemble into micellar structures and have surfactant properties. Note, these two synthetic cationic polypeptides are also described in FIGS. 4-6 and FIGS. 7-9, as noted above.

Various embodiments of the invention include antimicrobial compositions that comprise at least one antimicrobial agent that forms multimolecular complexes with itself and/or with one or more other components of the composition. By way of explanation, the development of such multimolecular complexes is enhanced by intermolecular binding. Such binding may be reversible. Such binding may be caused, wholly or in part, by hydrophobic attractive effects. Such binding may be covalent or non-covalent. Such binding may decrease or delay systemic absorption. Such binding may decrease risk of local and/or systemic toxicities.

Figure 12:
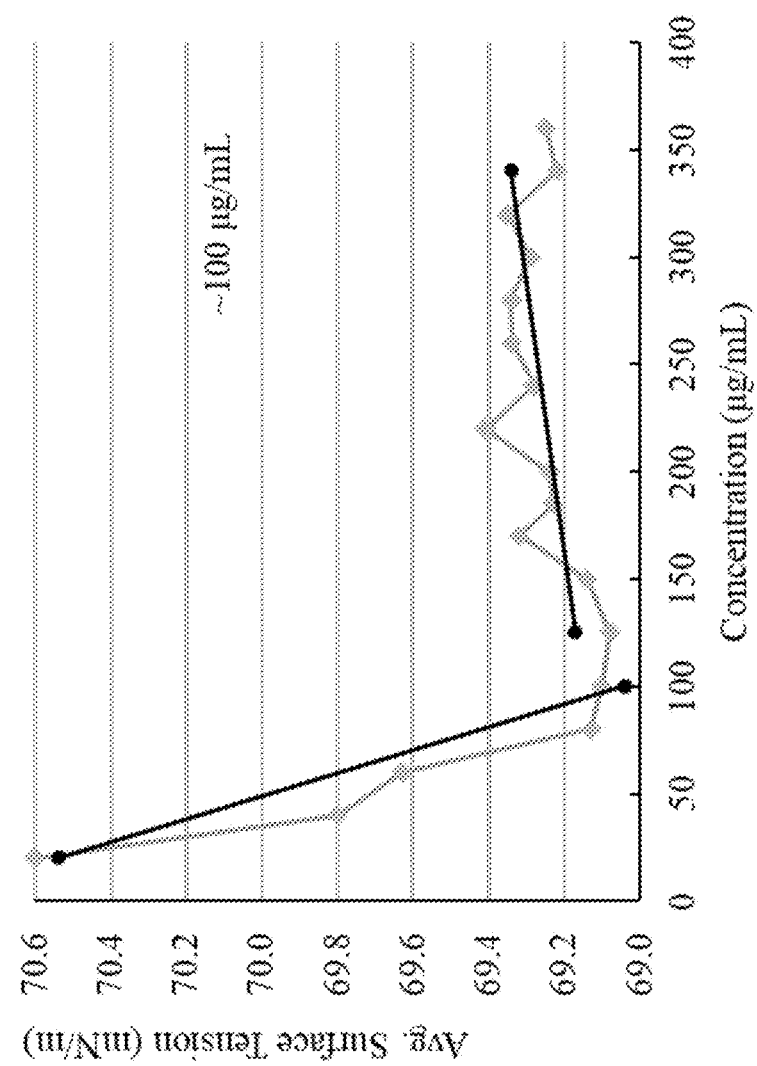
FIG. 12. Critical Aggregation Concentration (CAC) of synthetic cationic polypeptide(s) KrL-100/5.7 (Lot BAC002), as measured by surface tension method. Gray depicts surface tension over concentration; black depicts line of best fit for two sets of values. CAC is determined in this assay by the intersection of the two lines of best fit, shown here at ~100 μg/mL.

Critical Aggregation Concentration (CAC) is one measure of the self-assembly of molecules in aqueous environments. CAC can be measured by several techniques, including a pyrene fluorescence technique and a surface tension technique. FIG. 11 shows the CAC values of various synthetic cationic polypeptide(s) as measured by pyrene fluorescence method. It is noteworthy that both a polylysine chain (K-100) and a lysine-leucine synthetic cationic polypeptide (KL-130) that lacks a block sequence arrangement (KL-130/3.3-RAN) demonstrated very high CACs, 1,600 and 2,700 µg/mL, respectively. By comparison, numerous lysine-leucine synthetic cationic polypeptides possessing a block sequence arrangement demonstrated much lower CACs, ranging from 1 µg/mL to 160 µg/mL by this method as illustrated by the remaining entries in FIG. 11. FIG. 12 depicts the measurement of CAC by the surface tension method using the synthetic cationic polypeptide(s) KrL-100/5.7.

Various embodiments of the invention may include antimicrobial compositions that comprise at least one antimicrobial agent, which when dissolved in water has a critical aggregation concentration (CAC) less than or equal to 500 µg/mL. This CAC can be measured by methods known in the art, such as those using pyrene fluorescence. Other antimicrobial agents can have lower CACs. For example, antimicrobial agents can have CACs less than or equal to 200 µg/mL, 100 µg/mL, 50 µg/mL and/or 20 µg/mL.

Example 4

Viscosity is a relevant measure of molecular properties, as well as pharmaceutical composition properties. Unexpectedly, we discovered that increased viscosity can be a marker of increased intrawound antimicrobial performance, as well as a marker of increased safety. Multiple molecular design features influence the viscosity of synthetic cationic polypeptide(s). These include overall chain length, amino acid composition, cationic unit to hydrophobic unit ratio, and sequence arrangement of amino acid residues (e.g., blocky vs. random). It should also be noted that other constituents that may be in synthetic cationic polypeptide preparations (e.g., counterions, other salts, and residual solvents) can influence the viscosity of aqueous preparations. Further, various additives that may be used in the preparation of pharmaceutical compositions (e.g., salts, nonionic tonicity modifying excipients, surfactants) in amount effective to influence viscosity. As described below, methods of sterilization can also have substantial impacts on viscosity.

Figure 13:
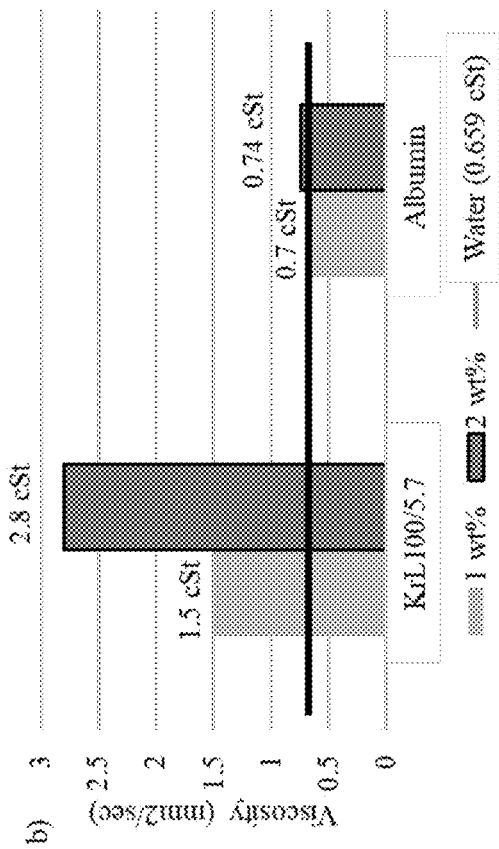
FIGS. 13A-B. (a) Kinematic viscosity of various synthetic cationic polypeptide(s) in water at 1 wt % and measured using glass capillary viscometers (Ubbelohde viscometers) at a temperature of 37° C. (b) Kinematic viscosity of KrL-100/5.7 (lot BAC002) vs. bovine serum albumin; water is provided for reference. The data indicate that at these concentrations albumin has little impact on viscosity of aqueous preparations.

FIG. 13A depicts kinematic viscosity values of various synthetic cationic polypeptide(s) in water at 1 wt % as measured using glass capillary viscometers (Ubbelohde viscometers). As demonstrated by this data, the presence of polylysine chains of approximately 100 amino acid units (K-100) or approximately 200 amino acid units (K-200) has only a modest impact on viscosity at this concentration. Similarly, the presence of a lysine-leucine synthetic cationic polypeptide(s) with random/statistical sequence arrangement (i.e., not block), KL-170/3.3-RAN, also had a modest effect on viscosity (value of 1.1 cSt). By contrast, multiple synthetic cationic-hydrophobic polypeptide(s) with segmented or block sequence arrangement demonstrated enhanced viscosity ranging from a high in this set of data of 290 cSt to 1.4 cSt. Overall chain length was shown to increase viscosity; increased length of the hydrophobic block was shown to increase viscosity; and enantiopurity of the hydrophobic leucine amino acids was shown to increase viscosity. For comparison, FIG. 13B shows that bovine serum albumin has little, if any effect on viscosity of aqueous preparations at concentrations of 1 and 2 wt % under these conditions. Albumin is an abundant blood protein and has a molecular weight of approximately 66.5 kDa and total chain length of approximately 583 amino acids units. These data indicate that molecular size alone is inadequate to explain viscosity effects.

FIG. 14 shows viscosity data for two synthetic cationic-hydrophobic polypeptide(s) at 0.5 wt % in water at 37° C. In this case, both synthetic cationic polypeptide(s), KL-160/3.3 and KL-120/2.5, had a similar length and design of the hydrophobic segment (~35-40 enantiopure L-leucine units). Higher viscosity was found with KL-160/3.3, which had a longer cationic block structure and consequently a longer overall structure. That said, it is also important to note that KL-120/2.5 had a higher viscosity at 0.5 wt % (FIG. 14) than KrL-160/3.3 (FIG. 13) at 1.0 wt %. The latter has a longer overall chain length, a similar sized hydrophobic block, but a different composition of hydrophobic amino acid units (racemic D,L-leucine vs. enantiopure L-leucine). FIG. 15 further demonstrates that both molecular design and concentration impact viscosity. This data was obtained at 40° C. with glass capillary viscometers and included four synthetic cationic polypeptide(s) from different manufacturing lots than those described above.

Figure 16:
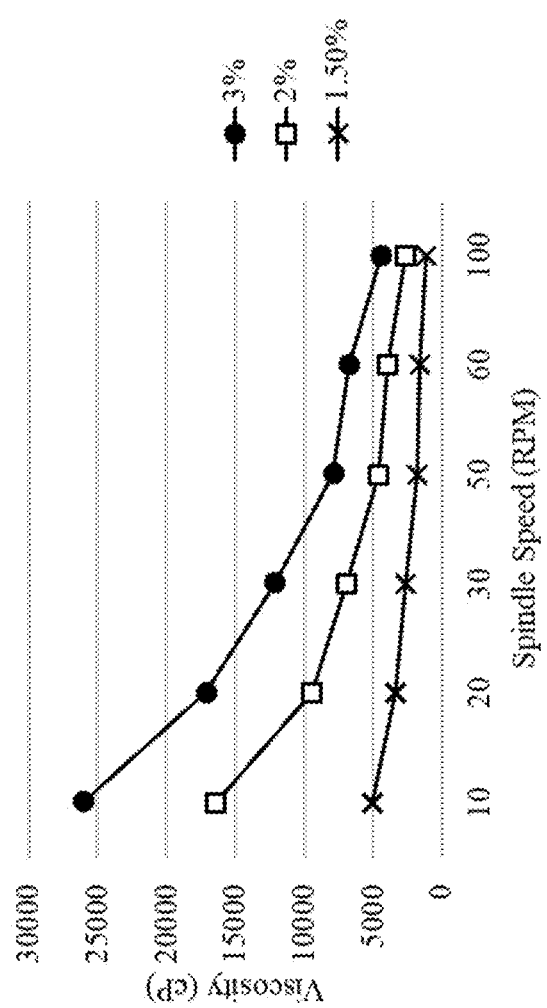
FIG. 16. Dynamic viscosity of synthetic cationic polypeptide(s) KL-120/2.5 at 1.5 wt %, 2.0 wt %, and 3.0 wt % in water assessed against increasing shear force. Measured over 2 min using a Brookfield RVDV (EQ-AL-2014-16) rotational viscometer with size 14 spindle and size 6R chamber at room temperature.

Synthetic cationic polypeptide viscosity can also be measured under the influence of shear force (dynamic viscosity). This approach allows the assessment of shear-thinning or shear-thickening properties. These shear thinning or shear-thickening properties may be important for both ease of application to tissues, as well as overall performance in vivo. Notably, we have found that shear-thinning properties may allow easier spread on tissues by manual manipulation, as could occur in a variety of medical and surgical settings. As depicted in FIG. 16, the dynamic viscosity of synthetic cationic polypeptide(s) KL-120/2.5 at 1.5 wt %, 2.0 wt %, and 3.0 wt % in water was assessed against increasing shear force using a rotational viscometer. Shear-dependent (increasing spindle speed) decreases in viscosity (measured in centipoise (cP)) were observed. This "shear-thinning" effect was seen at the three tested concentrations. Concentration-dependent increases in viscosity were also observed as indicated in FIG. 16.

Various embodiments of the invention include antimicrobial compositions that comprise at least one antimicrobial synthetic cationic polypeptide(s), which when dissolved in water, causes a significant increase in viscosity. For example, in an embodiment in which the synthetic cationic polypeptide(s) is a block copolymer, the observed increase in viscosity is greater than the increase observed for an otherwise comparable random synthetic cationic polypeptide(s). An increase in viscosity can be measured by methods known in the art using one or more types of viscometer(s).

By example, a preparation of at least one antimicrobial synthetic cationic polypeptide(s) at a concentration of 10 mg/mL or 1 wt. % in water may have a kinematic viscosity in the range of 1.25 centistokes to 500 centistokes (cSt; mm$^2$/s) at 37° C., measured using a glass capillary viscometer(s), such as Ubbelohde viscometer(s), in an assay in which the viscosity value of water alone is below 0.9 cSt. In various embodiments, the viscosities of these preparations of at least one antimicrobial agent are greater than 500 cSt.

Synthetic cationic polypeptide(s) can be designed and manufactured such that they form self-supporting hydrogels when dispersed in water. As depicted in FIGS. 17A-D, an example synthetic copolypeptide (KL-120/2.5) forms viscous solutions and hydrogels in water depending on concentration. KL-120/2.5 was prepared in DI water at concentrations of 0.5, 1.0, 1.5, 2.0, and 3.0 wt % and assessed for gel formation by a tilt tube assay, firmness by texture analysis, and viscosity. The concentration-dependent effects on physical properties are evident. For example, when increased to a concentration of 2 wt % in water, this synthetic cationic polypeptide(s) preparation formed a self-supporting hydrogel. At 1.5 wt %, the preparation acted as a barrier and resisted penetration by two different stainless steel spheres, or BBs. Quantitative measures of firmness using texture analysis also clearly displayed concentration-dependent increases. This latter method also demonstrates barrier properties and resistance to penetration.

Example 5

Various additives can modify viscosity of aqueous preparations of synthetic cationic polypeptide(s). We have found that a variety of additives may be used to alter certain properties of the pharmaceutical compositions described herein, including pH and tonicity. During evaluation, we found that certain additives had an unexpectedly high impact on viscosity. These impacts were further discovered to depend on the molecular design of the synthetic cationic polypeptide(s). For example, in multiple studies it was demonstrated that the addition of NaCl (~0.9%) to aqueous preparations of Group II Medium lysine-L-leucine (KL) polypeptide(s) with block amino acid sequence arrangements profoundly decreased viscosity. A similar, but less profound effect, was observed with lysine-D,L-leucine (KrL) polypeptide(s). This data showed that both molecular design and the nature of additives should be considered together in preparation of pharmaceutical compositions with targeted viscosity parameters. These observations also provide a reminder that certain substances, including salts, that may be found in manufactured preparations of synthetic cationic polypeptides can profoundly influence functionality and performance.

Figure 18:
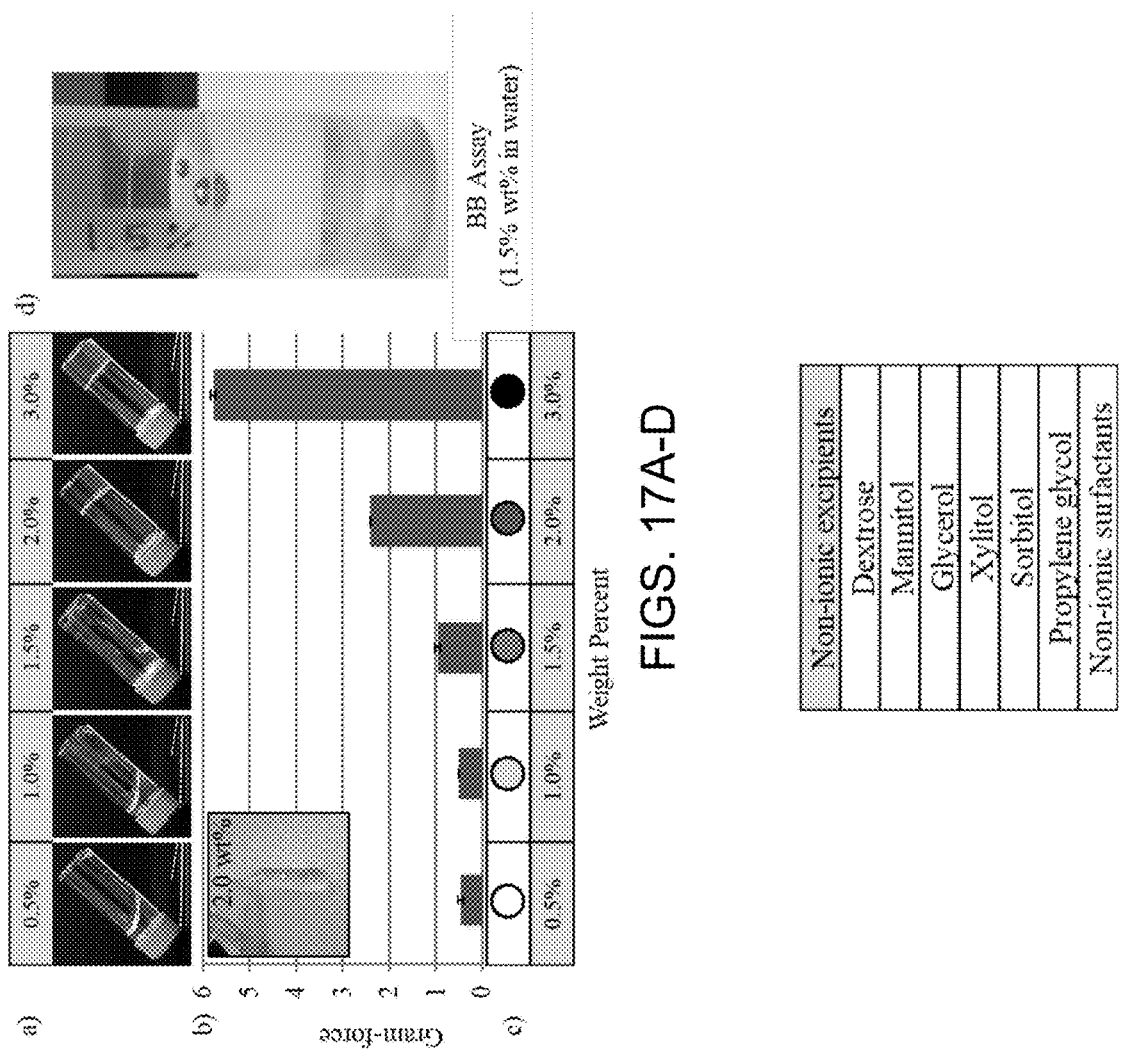
FIG. 18. Partial list of pharmaceutically acceptable nonionic excipients (additives) that may be used in preparations of synthetic cationic polypeptide(s) and antimicrobial pharmaceutical compositions containing them.
Figure 19:
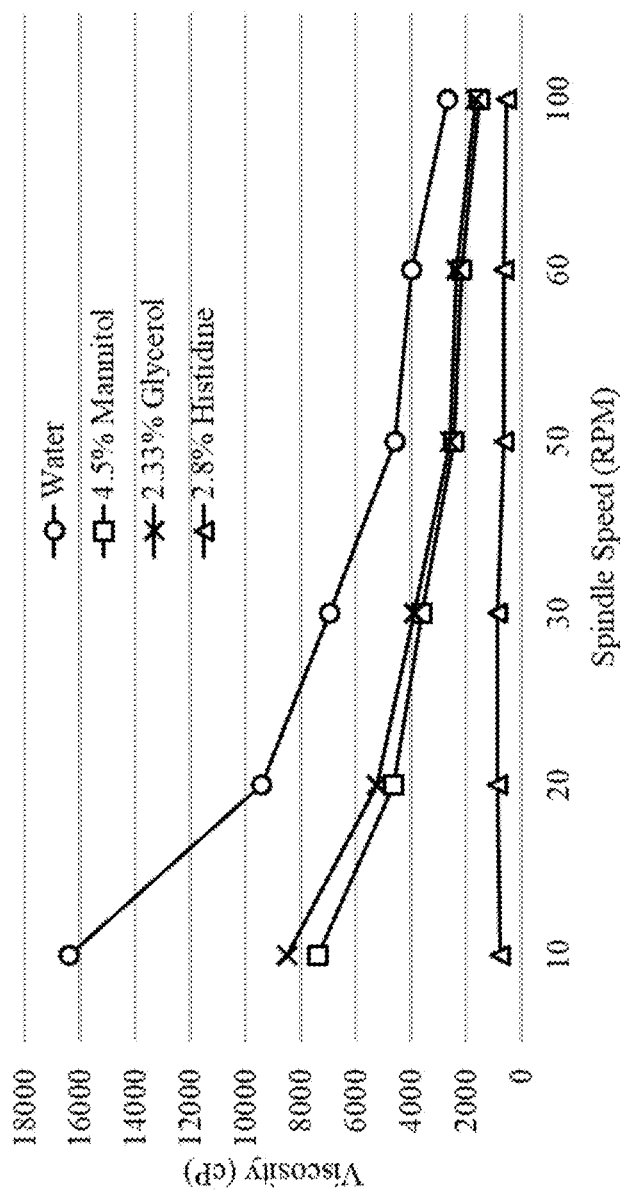
FIG. 19. Dynamic viscosity of synthetic cationic polypeptide(s) KL-120/2.5 (BAC004) at 2.0 wt % in water, 4.5% aqueous mannitol, 2.33% aqueous glycerol, or 2.8% aqueous histidine, assessed against increase shear force. Measured over 2 minutes using a Brookfield RVDV (EQ-AL-2014-16) rotational viscometer with size 14 spindle and size 6R chamber at room temperature.

FIG. 18 shows a partial list of pharmaceutically acceptable non-ionic excipients (additives) that may be used to prepare pharmaceutical compositions that contain synthetic cationic polypeptide(s). FIG. 19 depicts dynamic viscosity of synthetic cationic polypeptide(s) KL-120/2.5 (BAC004) at 2.0 wt % in water, 4.5% aqueous mannitol, 2.33% aqueous glycerol, or 2.8% aqueous histidine, assessed against increased shear force. The histidine preparation showed very low viscosity at all spindle speeds. The preparations in mannitol and glycerol showed relatively high and shear-dependent viscosity profiles, albeit at levels somewhat lower than observed in the water-only preparation.

FIG. 20 depicts kinematic viscosity of two example synthetic cationic polypeptide(s) with a lysine-L-leucine (KL) and lysine-D,L-leucine (KrL) block sequence arrangement dissolved in water at 1 wt % in water alone, 0.9% aqueous saline, or 4.4% aqueous xylitol. Notably, preparation of KL-100/5.7 in 0.9% saline demonstrated an approximate 70% decrease in viscosity by comparison to the preparation in water. By comparison, preparation of KrL-110/4.0 in 0.9% saline demonstrated an approximate 40% decrease in viscosity by comparison to the preparation in water. Further, these studies demonstrated that both synthetic cationic polypeptide(s) in aqueous solutions of xylitol, a non-ionic additive, resulted in unexpectedly enhanced viscosities by comparison to water alone. Thus, xylitol adds a potential benefit as an additive for pharmaceutical compositions where it is desirable to maintain a higher viscosity while increasing tonicity and/or osmolarity. Further, in some embodiments xylitol is an unexpectedly preferred pharmaceutically acceptable additive in antimicrobial compositions because, in combination with its effect on viscosity, it does not support microbial metabolism and growth of most microbes.

Figure 21:
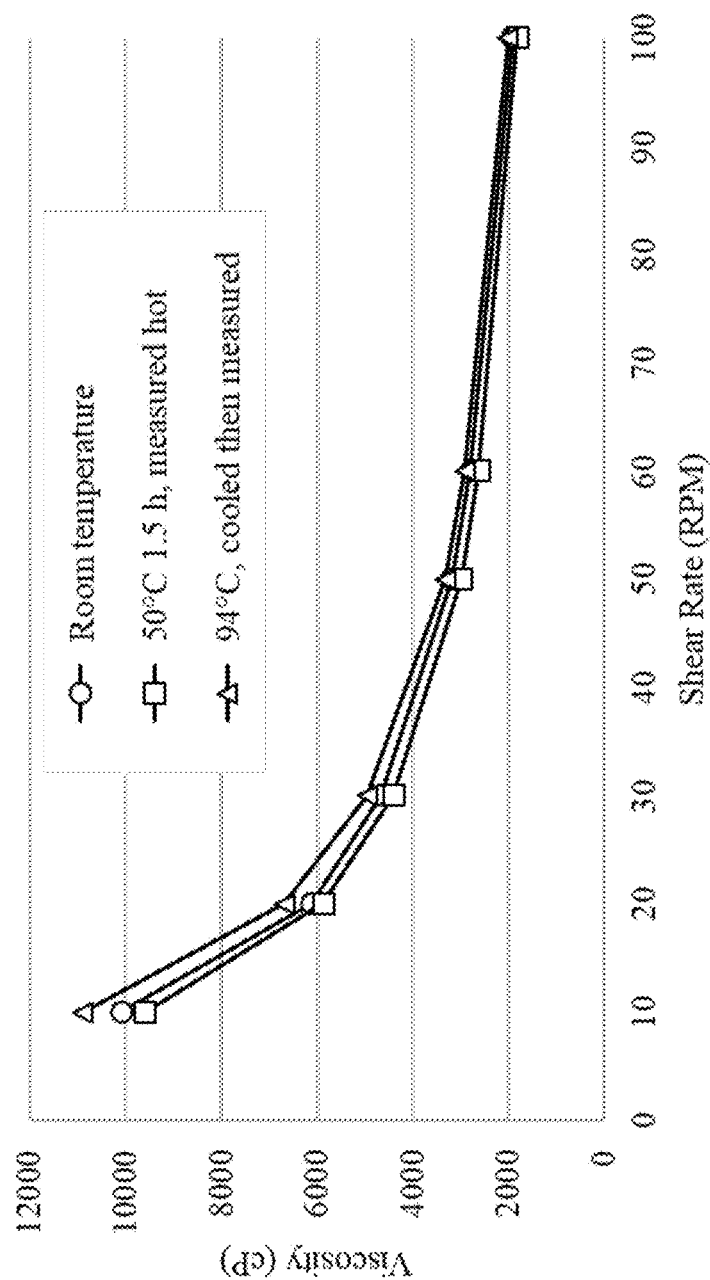
FIG. 21. Dynamic viscosity of preparations of synthetic cationic polypeptide(s) KL-120/2.5 (BAC004) at 2.0 wt % in 4.5% mannitol and water, assessed against increase shear force. Measured over 2 minutes using a Brookfield RVDV (EQ-AL-2014-16) rotational viscometer with size 14 spindle and size 6R chamber at room temperature.

FIG. 21 depicts dynamic viscosity of synthetic cationic polypeptide(s) KL-120/2.5 (BAC004) at 2.0 wt % in 4.5% aqueous mannitol, assessed against increased shear force. It further depicts that these preparations are stable to heat treatment, including 50° C. and 94° C. Stability to heat treatment may be useful for certain manufacturing steps, dissolution and annealing of synthetic cationic polypeptide (s) in aqueous carriers, and for reduction or elimination of any contaminating microbes by sterilization.

Various embodiments of the invention include pharmaceutical compositions that comprise at least one antimicrobial synthetic cationic polypeptide(s) in an aqueous carrier and at least one additive or excipient, in combinations and amounts that are effective to result in a viscosity for the pharmaceutical composition in the range of about 1.25 centistokes to 500 centistokes (cSt; $mm^2/s$) at 37° C., measured using a glass capillary viscometer(s), such as Ubbelohde viscometer(s), in an assay in which the value of water alone is below 0.9 cSt. In various embodiments, the viscosities of these pharmaceutical compositions are greater than 500 cSt.

Various embodiments of the invention include pharmaceutical compositions that comprise at least one antimicrobial synthetic cationic polypeptide(s) in an aqueous carrier and an amount of at least one additive or excipient that is effective to impart a shear-thinning effect to the composition at 37° C., as measured using a rotational viscometer(s).

Various embodiments of the invention include pharmaceutical compositions comprising at least one antimicrobial synthetic cationic polypeptide(s) in an aqueous carrier and an amount of at least one additive or excipient that is effective to impart a viscosity to the composition greater than that of a comparable preparation in the aqueous carrier without the additive or excipient. For example, in an embodiment the addition of effective amounts of xylitol or glycerol to a pharmaceutical composition, including compositions that may also contain various salts like NaCl, enhances the viscosity of the preparation by comparison to the comparable pharmaceutical composition without xylitol or glycerol.

In accordance with the present invention, reaching an effective level of antimicrobial activity may require substantial doses of the pharmaceutical compositions described herein in certain patients (e.g., those with large wounds and/or high microbial levels). We have found that an antimicrobial agent, if designed in accordance with the teachings provided herein, can enhance both the effectiveness and safety of locally applied antimicrobial compositions. An antimicrobial agent that forms multimolecular complexes with itself or with one or more other components of the composition may increase local concentration and tissue coating of the antimicrobial agent to thereby obtain greater effectiveness at lower dose. In addition, this characteristic may diminish or slow down potential systemic absorption and distribution, and may decrease systemic toxicities. It may also decrease local toxicities. Design of the antimicrobial agent itself, as well as formulation of the antimicrobial composition will influence the intermolecular interactions that enable the formation of multimolecular complexes.

We have found that the effectiveness and safety of locally applied antimicrobials are influenced by physical properties, including viscosity. For example, increased viscosity may lead to increased tissue retention time of a locally applied antimicrobial and thereby enhance effectiveness. This effect may also decrease the total amount of antimicrobial composition required, and thereby decrease the risk of dose-limiting toxicities. The intermolecular interactions of the antimicrobial agent with itself or with other components of the composition contribute to the increased viscosity of the antimicrobial composition.

Example 6

Figure 22:
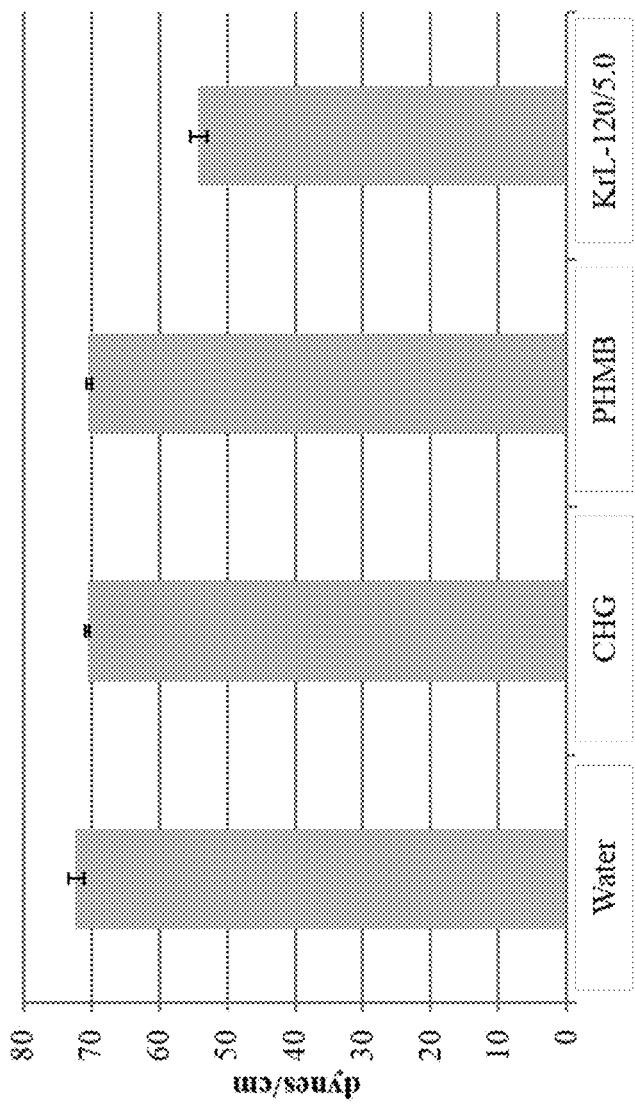
FIG. 22. Example synthetic cationic polypeptide(s) KrL-120/5.0 preparation is shown to decrease surface tension by comparison to two other cationic antimicrobials, chlorhexidine gluconate (CHG) and polyhexamethylene biguanide (PHMB). Samples were prepared at 0.1 mM and assessed using TA.XT2 Texture Analyzer with a 500 g load cell, 5 cm diameter Du Nouy ring and probe speed of 0.2 mm/s at room temperature.

Synthetic cationic polypeptide(s) can be designed to demonstrate surfactant activity. Certain design features impart more surfactant activity; others impart less. Surfactant activity can be demonstrated in multiple assays. For example, surfactants can be shown to decrease surface tension at a fluid-air interface. As depicted in FIG. 22, a synthetic cationic polypeptide KrL-120/5.0 was shown to substantially reduce surface tension of water by comparison to other cationic antimicrobial agents that are not synthetic cationic polypeptides; chlorhexidine and PHMB appeared to have little or no effect.

The ability of various preparations of synthetic cationic polypeptide(s) to decrease surface tension was assessed (FIG. 23). Several observations were made. Unexpectedly, lysine-leucine diblock copolypeptides prepared with enantiopure L-leucine demonstrated little surfactant activity when the hydrophobic block was 30 amino acid units or longer. Surfactant activity was observed with shorter enantiopure L-leucine blocks (e.g. about 20 leucine units or less). In addition, lysine-leucine diblock copolypeptides prepared with racemic D,L-leucine demonstrated relatively high surfactant activity, when compared to those prepared with enantiopure L-leucine at leucine block lengths of about 20 units or more. Overall, the data shows that surfactant activity is profoundly influenced by both the amino acid composition (including enantiopure vs racemic) and the length of the hydrophobic block). Thus, design elements can be used to obtain desirable surfactant properties of synthetic cationic polypeptide(s).

Figure 24:
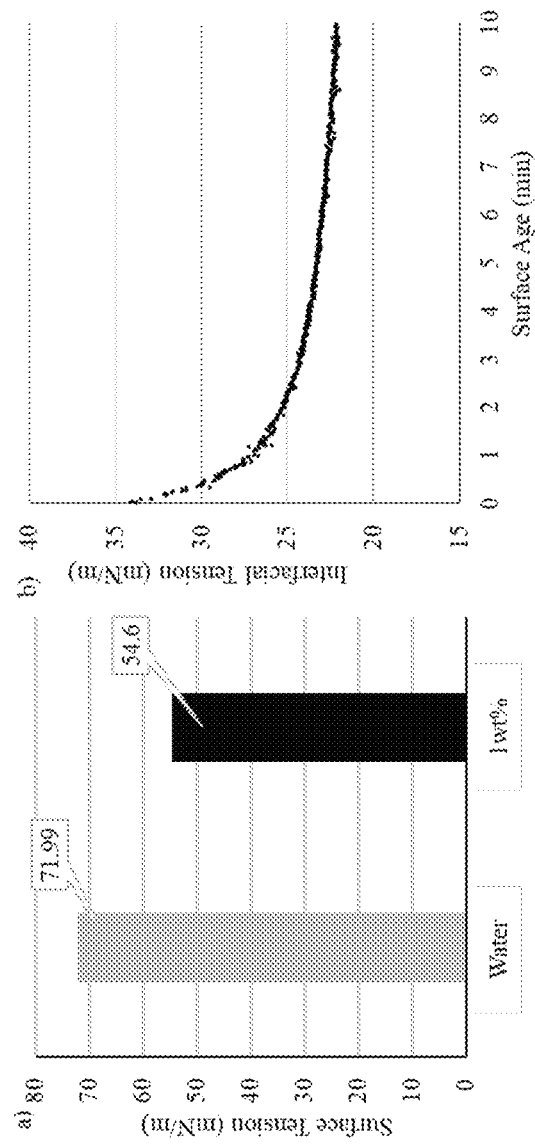
FIGS. 24A-B. Surfactant properties of KrL-100/5.7. (a) Surface tension of aqueous KrL-100/5.7 (Lot BAC002) 10 mg/mL (1 wt %) via a tensiometer equipped with a Du Nouy ring as compared to water. (b) Interfacial tension of KrL-100/5.7 at 1 wt % in water with n-hexane over 10 minutes.

Surfactant activity can also be demonstrated by other assays. One example is reduction of interfacial tension in a water/oil system. As depicted in FIGS. 24A and 24B, a synthetic cationic polypeptide(s) KrL-100/5.7 was shown to reduce interfacial tension.

Figure 25:
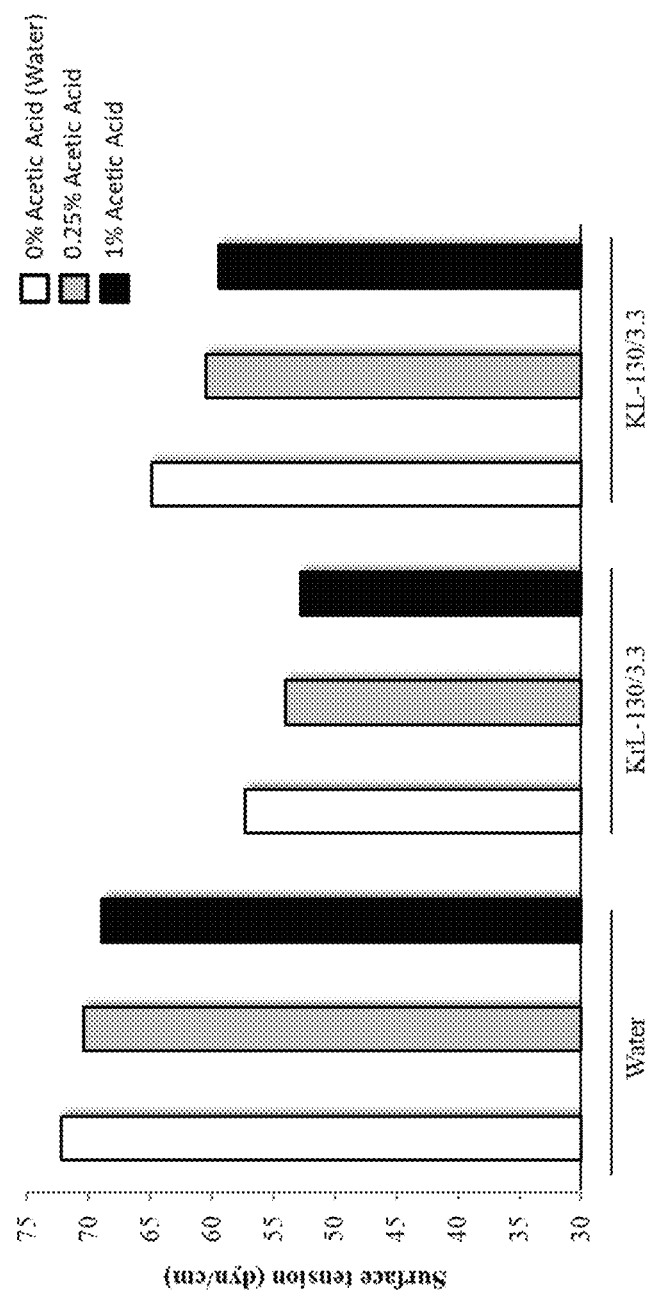
FIG. 25. Surface tension: effect of acetic acid as an additive. Example synthetic cationic polypeptide(s) KrL-130/3.3 (Lot 77) and KL-130/3.3 (Lot 72) lower surface tension when prepared in water or water with 0.25% or 1.0% acetic acid. The addition of acetic acid has an additive effect.
Figure 26:
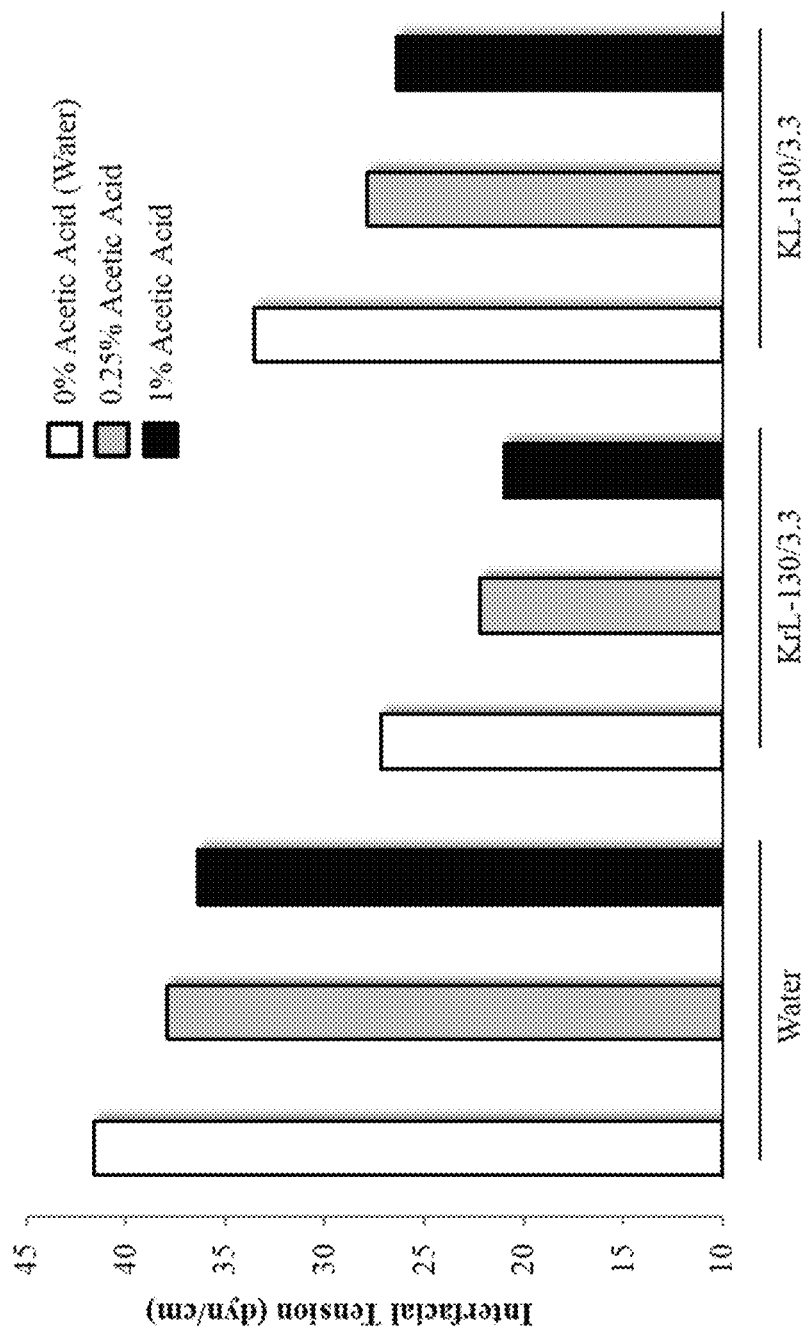
FIG. 26. Interfacial tension: effect of acetic acid as an additive. Example synthetic cationic polypeptide(s) KrL-130/3.3 (Lot 77) and KL-130/3.3 (Lot 72) lower interfacial tension when prepared in water or water with 0.25% or 1.0% acetic acid. The addition of acetic acid has an additive effect.

Certain additives can also have an impact on surface and interfacial tension. For example, the data in FIG. 25 shows that preparations of synthetic cationic polypeptide(s) KrL-130/3.3 (Lot 77) and KL-130/3.3 (Lot 72) lower surface tension when formulated in water alone or in water with 0.25% or 1.0% acetic acid. The presence of acetic acid has an additive effect. A similar effect was observed on interfacial tension (FIG. 26)

Synthetic cationic polypeptide(s) can be effective emulsifying agents. As shown in FIG. 27, we demonstrate that aqueous preparations of two example synthetic cationic polypeptide(s) with a racemic D,L-leucine hydrophobic segment, KrL-100/5.0 and KrL-160/3.2, are effective at emulsifying soybean oil. This emulsification effect was also observed with a synthetic cationic polypeptide(s) having an enantiopure leucine hydrophobic block (FIG. 28). The data in FIG. 28 also demonstrates that emulsification activity can be demonstrated by synthetic cationic polypeptide(s) formulated in saline or aqueous xylitol, as well as water alone.

Synthetic cationic polypeptide(s) can be designed and formulated to demonstrate surfactant activities. We have also found that preparations of synthetic cationic polypeptide(s) that combine direct microbicidal activity and surfactant properties are highly effective anti-biofilm agents. Further, we have demonstrated that such preparations are highly effective in vivo on tissues that are heavily contaminated with both gram-positive and gram-negative bacteria.

Example 7

Understanding the potential for both local and systemic toxicities is important. Local tissue compatibility and safety are both highly desirable for the effective use of a locally applied antimicrobial composition. Overall, we have found that preparations of synthetic cationic polypeptides with a block or segmented sequence arrangement demonstrate relatively high tissue compatibility and local safety. In addition, proper formulations, doses, and methods of application as described herein can be used to minimize tissue damage and support healing.

Unexpectedly, we have found substantial variability of different preparations of synthetic cationic polypeptides when it comes to systemic safety. We have discovered that molecular design and formulation both profoundly influence the risk of systemic toxicities when synthetic cationic polypeptide(s) preparations are applied intraperitoneally. Intraperitoneal administration, albeit a type of local application, facilitates substantial systemic uptake and distribution of therapeutic agents and excipients. Thus, intraperitoneal administration poses a higher risk of systemic toxicities than does most local applications of antimicrobial pharmaceutical compositions. It is important to note several things in this regard. First, local applications to a variety of tissues other than intact, health skin can increase systemic uptake. Second, intraperitoneal infections are very serious and there is a need for better, safer antimicrobials that can be applied intraperitoneally. Third, inadvertent application of pharmaceutical compositions, intraperitoneally, intravenously, or in other sites that could dramatically increase systemic uptake, can occur. We have now developed locally applied antimicrobial pharmaceutical compositions that are highly effective and that have a low risk of both local and systemic toxicities, even when applied to sites other than healthy, intact skin.

FIG. 29 depicts the results of a rabbit dermal irritation model in which compositions of synthetic cationic polypeptide(s) were applied to both intact and abraded skin. Negligible responses were observed after application of synthetic cationic polypeptide(s) KL-140/2.5 or KrL-120/5.0 at various concentrations and various formulations. FIG. 30 depicts the results of a guinea pig dermal sensitization study. No visible changes were observed following application of KL-140/2.5 (lot 73) or KrL-120/5.0 (lot 93) at 1 wt % in water, indicating to those skilled in the art that the synthetic cationic polypeptide(s) showed no sensitization potential. FIG. 31 depicts the results of a rat oral toxicity study. No abnormalities were noted over three days following administration of KL-140/2.5 in water or KrL-120/5.0 in water to rats at doses ranging from 0.625 mg/kg to 160 mg/kg by oral gavage.

Figures 32, 33:
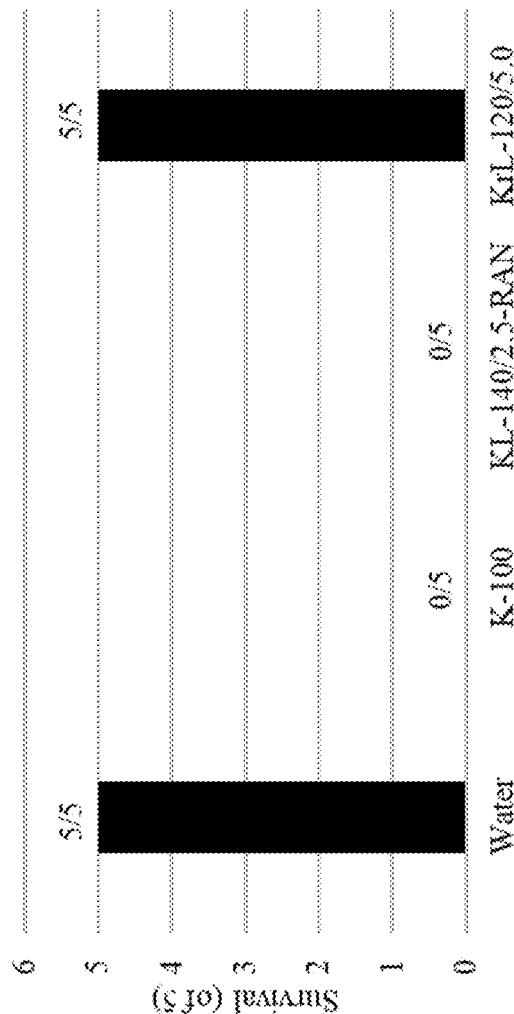
FIG. 32. Evaluation of mouse systemic toxicity after intraperitoneal administration. CD-1 mice received intraperitoneal injection of 40 mL/kg of water or test articles K-100, KL-140/2.5-RAN, or KrL-120/5.0 diluted in water at 2 wt %. The final dose per animal was 800 mg/kg. N=5 CD-1 mice per group. Clinical observations were performed for three days.
FIG. 33. Evaluation of mouse systemic toxicity after intraperitoneal administration. CD-1 mice received intraperitoneal injection of 40 mL/kg of saline or KrL-130/3.3 diluted in water at various concentrations. Final doses per animal ranged from 12.5 mg/kg to 800 mg/kg. N=5 CD-1 mice per group. Clinical observations were performed for three days.
Figure 38:
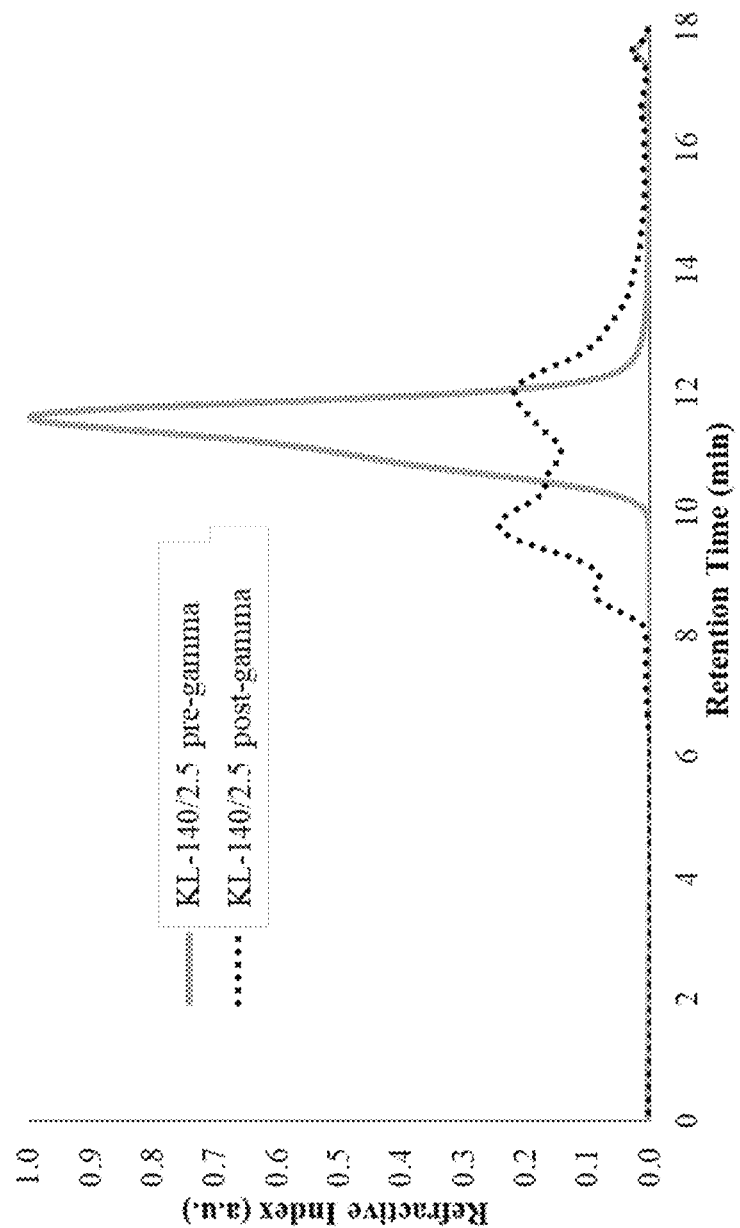
FIG. 38. SEC chromatograms of KL-140/2.5 (lot 73) pre-gamma sterilization and post-gamma sterilization with a dose of 25-40 kGy. Data indicate breakdown in molecular structure after gamma irradiation.
Figure 39:
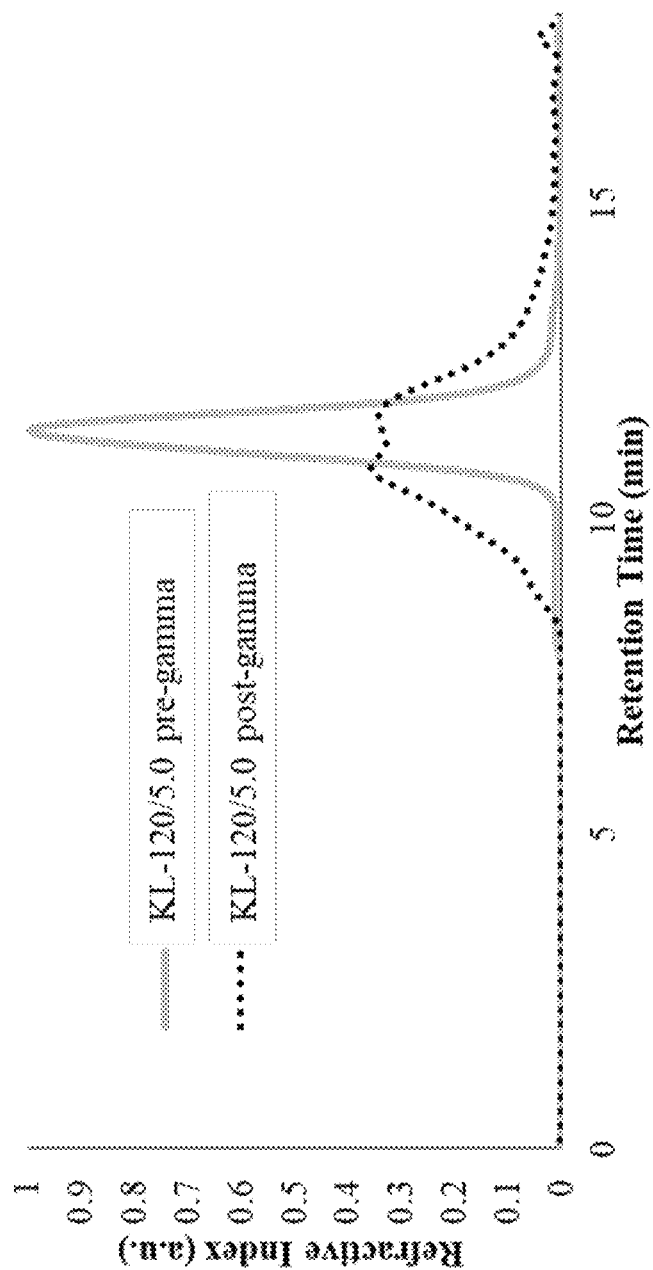
FIG. 39. SEC chromatograms of KL-120/5.0 (lot 94) pre-gamma sterilization and post-gamma sterilization with a dose of 25-40 kGy. Data indicate breakdown in molecular structure after gamma irradiation.
Figure 40:
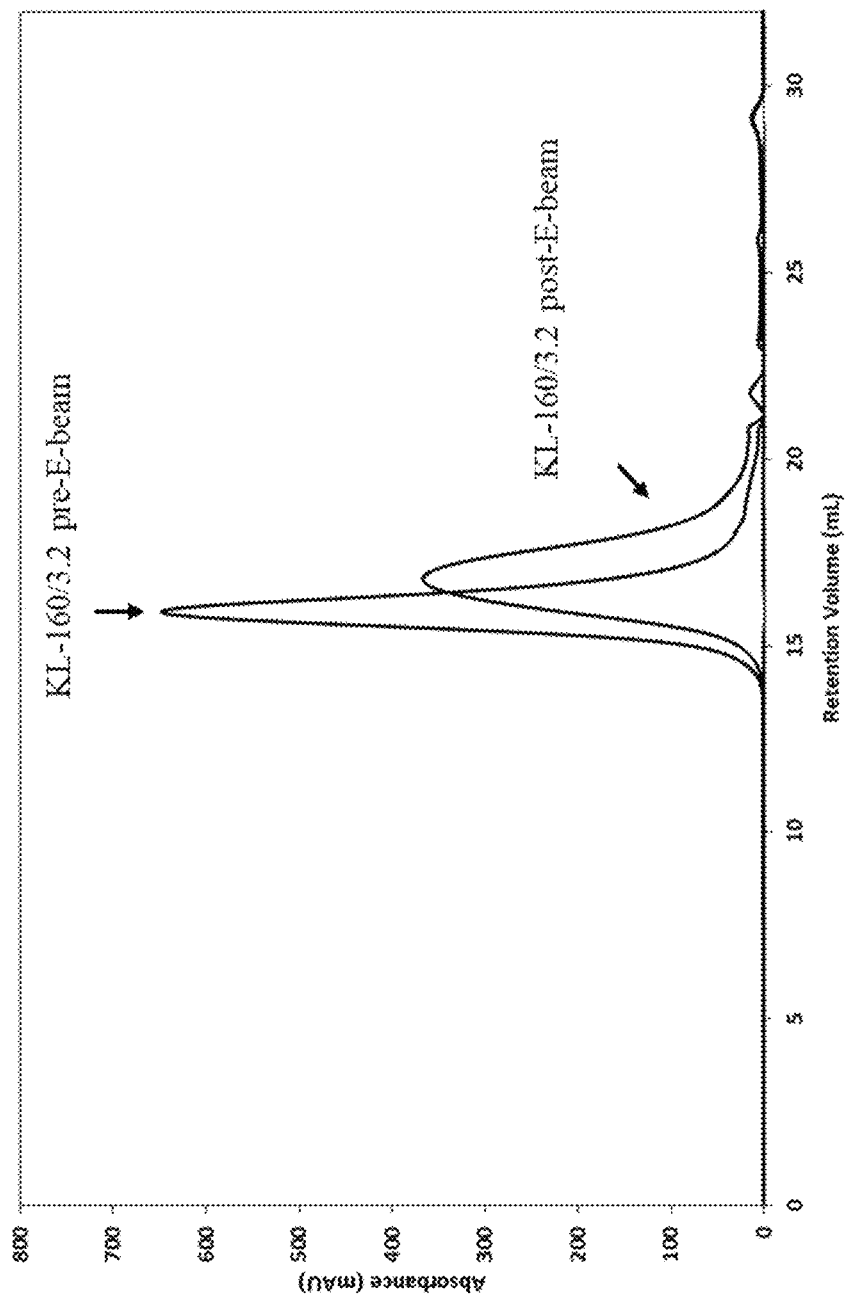
FIG. 40. SEC chromatograms of KL-160/3.2 (lot BAC003) pre-E-beam sterilization and post-E-beam sterilization with a dose of 25 kGy. Data indicate breakdown in molecular structure after E-beam sterilization.
Figure 41:
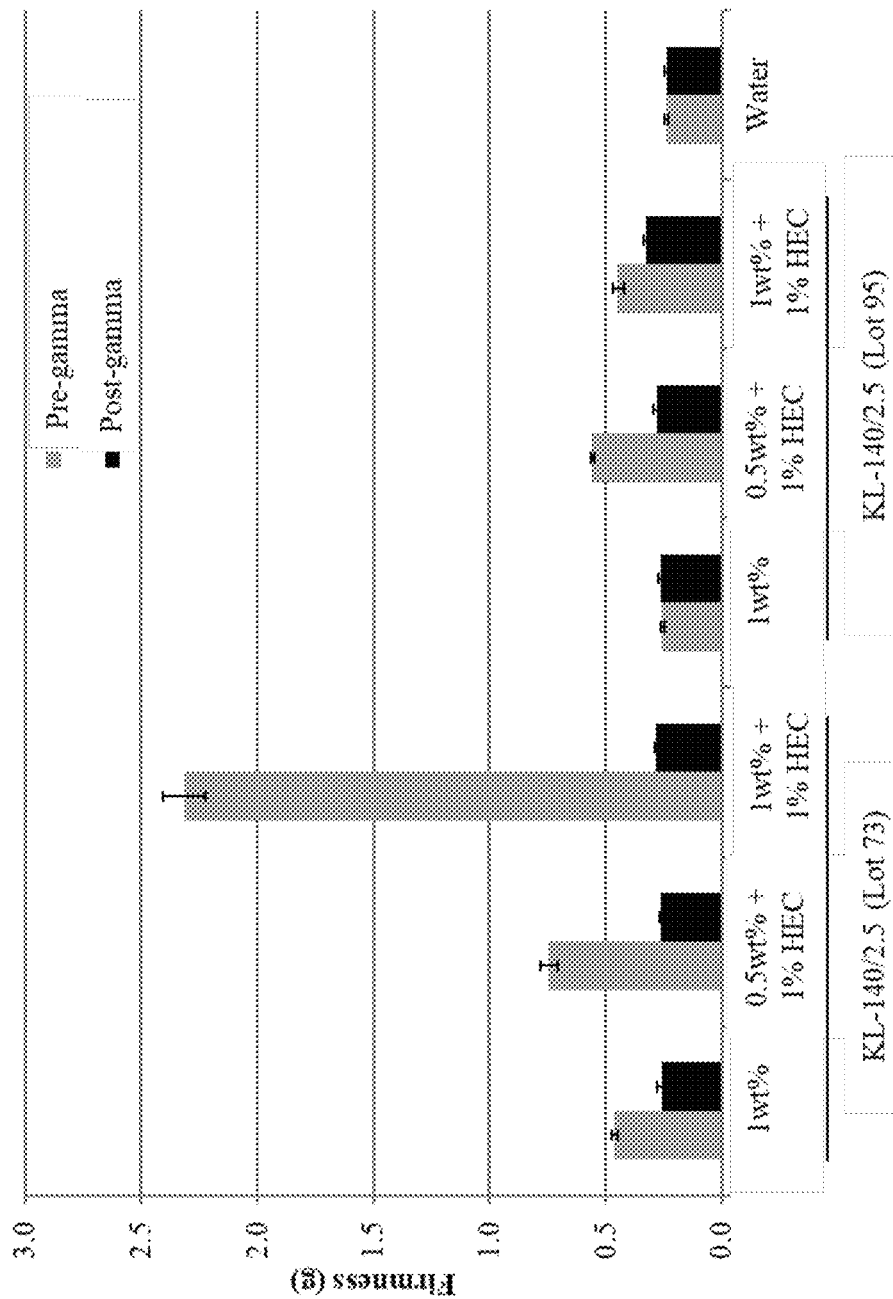
FIG. 41. Texture analysis of two KL-140/2.5 lots (73 and 95) pre-gamma sterilization and post-gamma sterilization with a dose of 25-40 kGy. Measured using a TA.XT2 texture analyzer with a probe speed of 0.5 mm/s. Data indicate a decrease in the firmness of most of these compositions after gamma irradiation.
Figure 42:
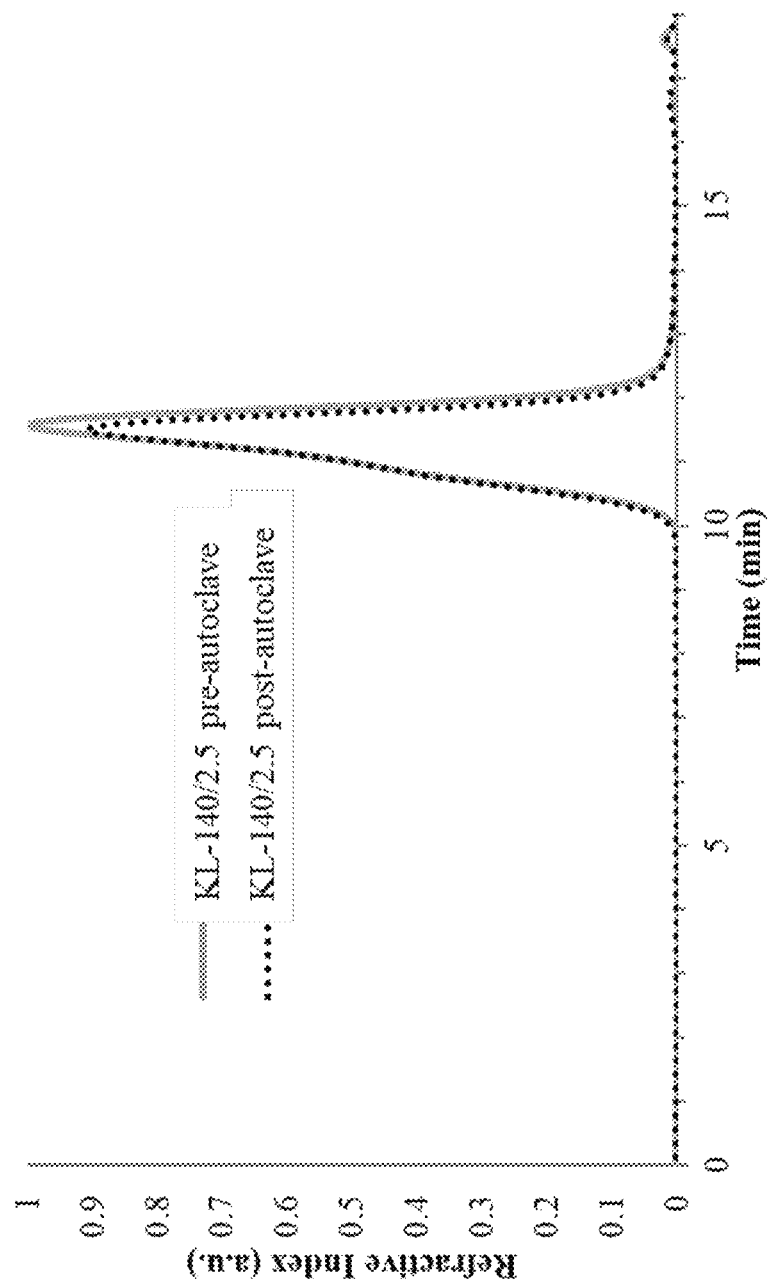
FIG. 42. SEC chromatograms of KL-140/2.5 (lot 73) prepared in water pre-autoclave sterilization and post-autoclave sterilization. Data indicate maintenance of molecular structure after autoclave sterilization.
Figure 43:
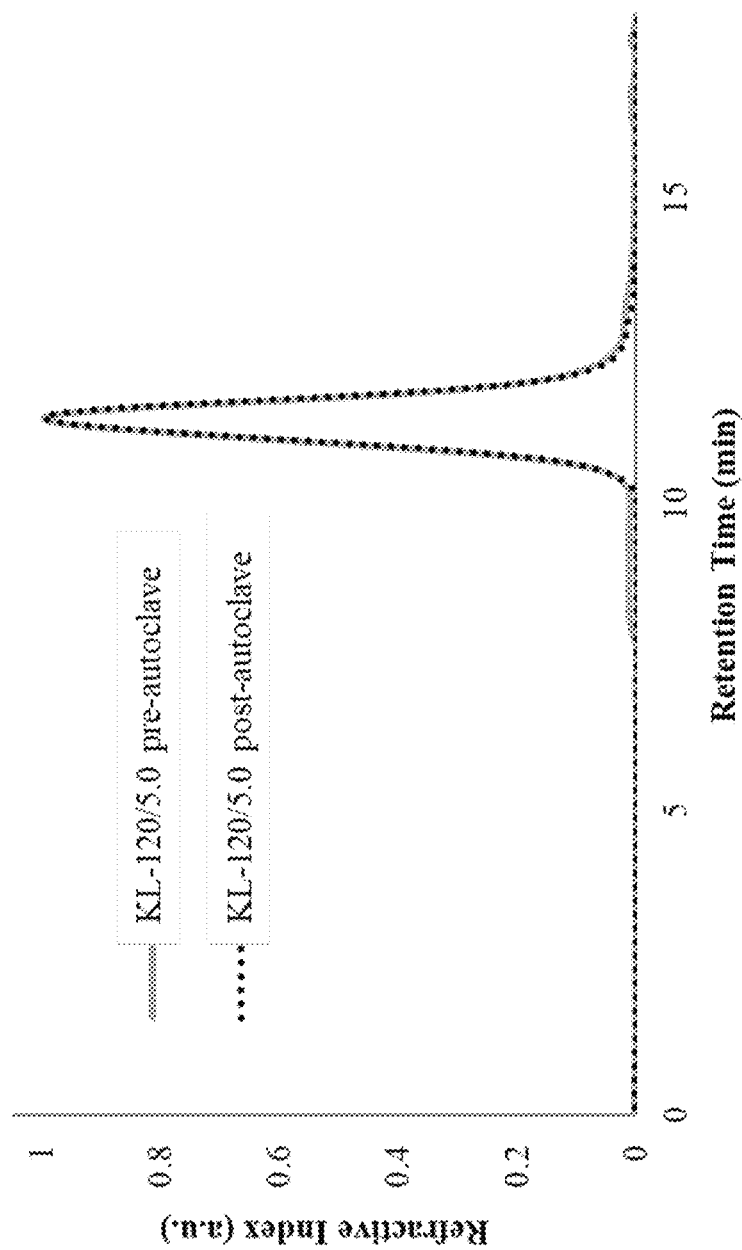
FIG. 43. SEC chromatograms of KL-120/5.0 (lot 94) prepared in water pre-autoclave sterilization and post-autoclave sterilization. Data indicate maintenance of molecular structure after autoclave sterilization.
Figure 44:
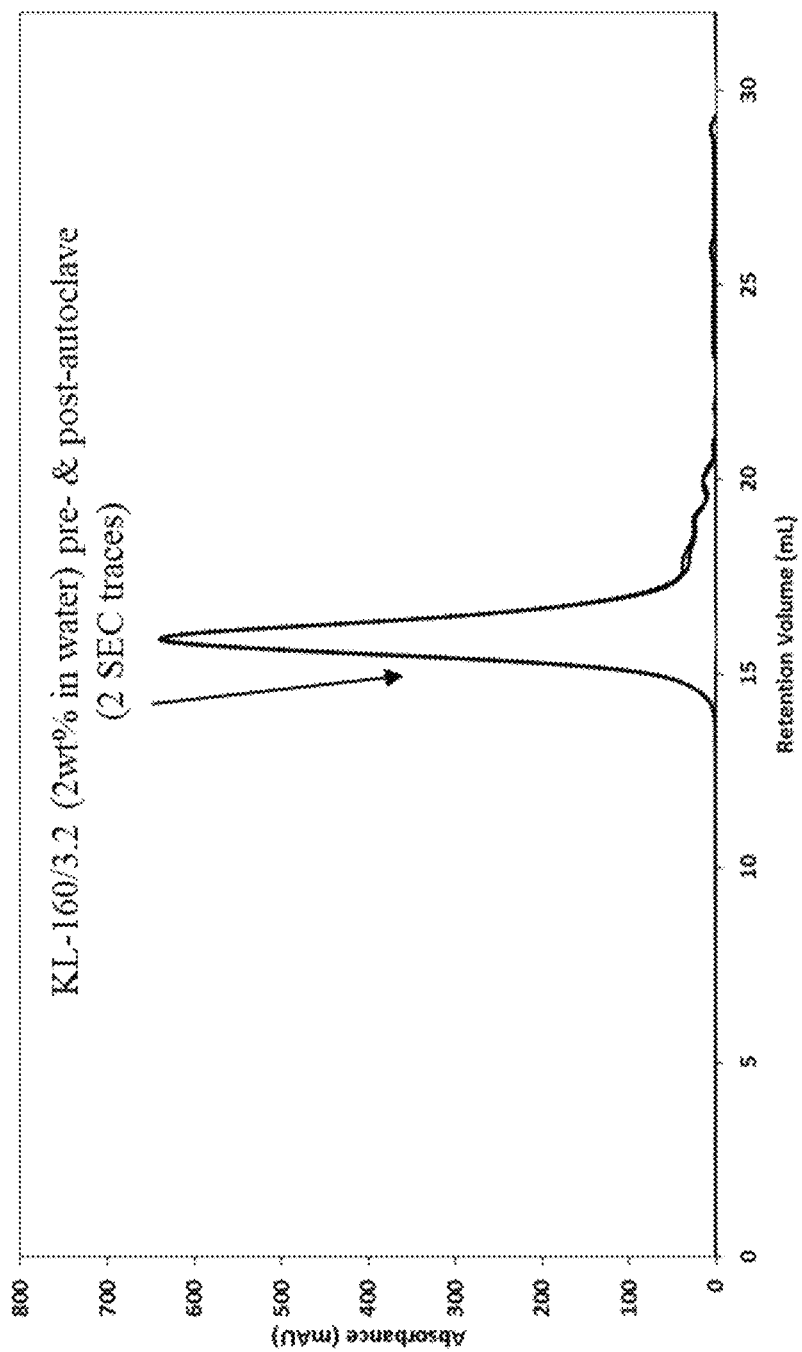
FIG. 44. SEC chromatograms of KL-160/3.2 (lot BAC003) prepared at 2 wt % in water pre-autoclave sterilization and post-autoclave sterilization. Data indicate maintenance of molecular structure after autoclave sterilization.
Figure 45:
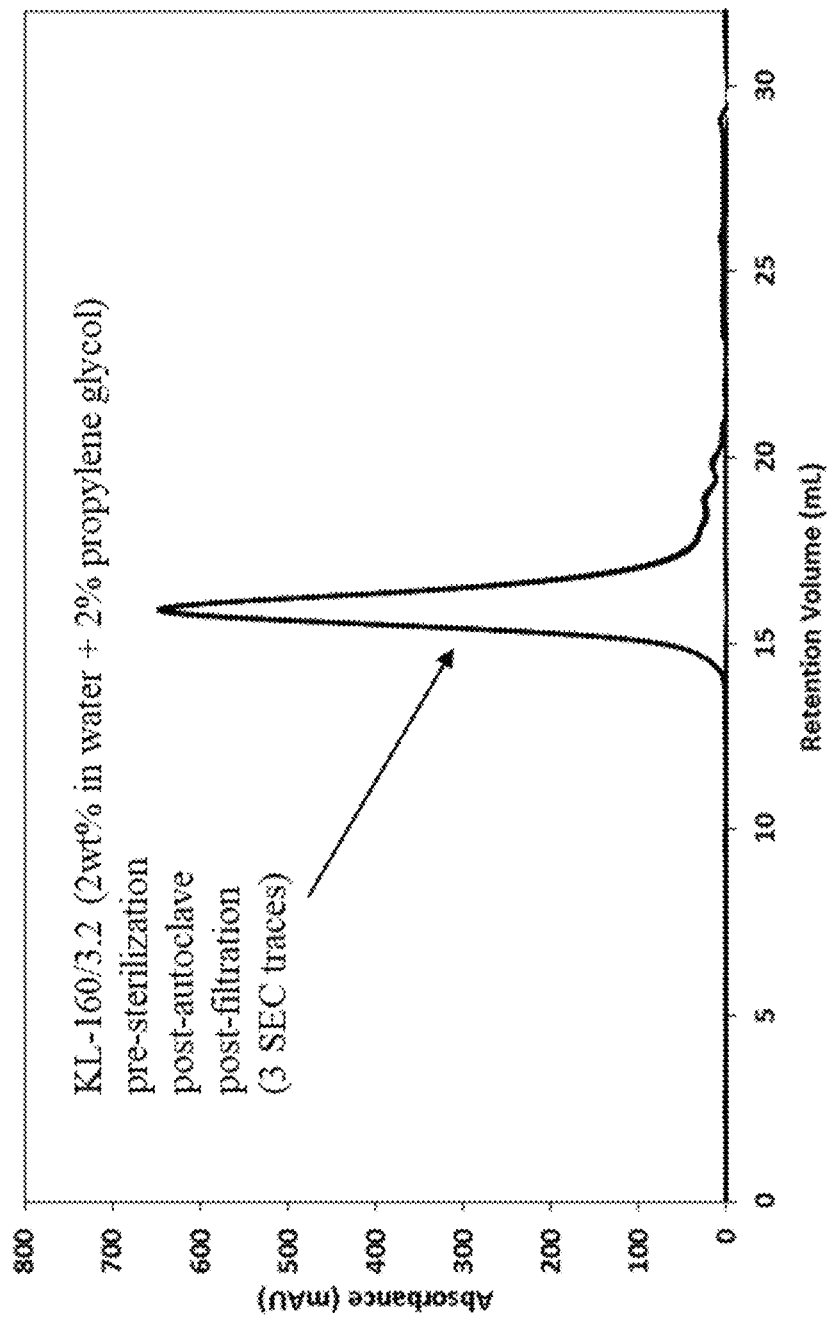
FIG. 45. SEC chromatograms of KL-160/3.2 (lot BAC003) prepared at 2 wt % in water with 2% propylene glycol pre-sterilization, post-autoclave sterilization, and post-filtration sterilization. Data indicate maintenance of molecular structure after autoclave sterilization and after filter sterilization.
Figure 46:
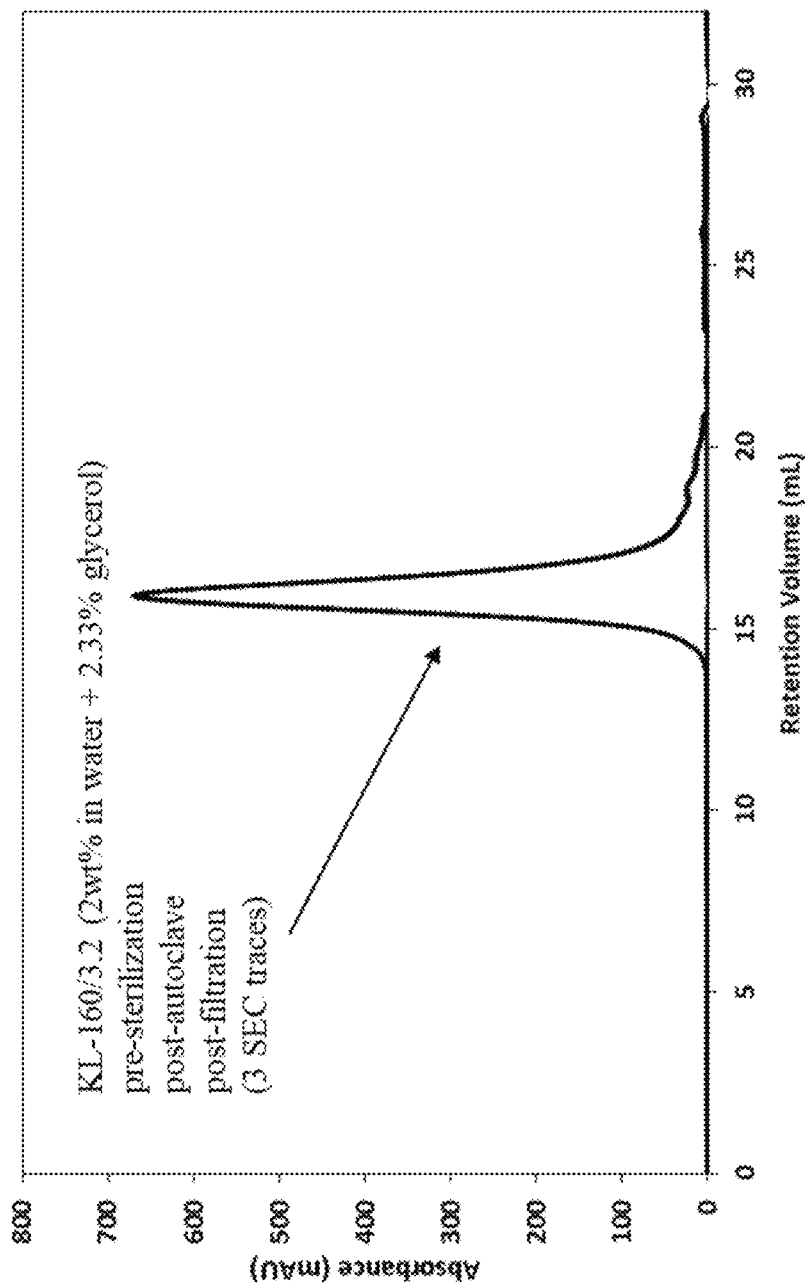
FIG. 46. SEC chromatograms of KL-160/3.2 (lot BAC003) prepared at 2 wt % in water with 2.33% glycerol pre-sterilization, post-autoclave sterilization, and post-filtration sterilization. Data indicate maintenance of molecular structure after autoclave sterilization and after filter sterilization.

Studies of systemic toxicity after intraperitoneal administration provided unexpected results. As shown in FIG. 32, intraperitoneal administration of a polylysine of approximately 100 amino acid units (K-100) at a concentration of 20 mg/mL and overall dose of 800/mg/kg was found to be quite toxic, with 0 of 5 animals surviving. Similarly, a preparation of synthetic cationic polypeptide(s) KL-140/2.5-RAN, which lacks a block sequence arrangement of amino acid units, was found to be toxic with 0 of 5 animals surviving. By contrast, all animals (5/5) survived following administration of a comparable concentration and dose of KrL-120/5.0 in water. As shown in FIG. 33, aqueous preparations of another cationic polypeptide with a segmented or block sequence arrangement of lysine and D,L-leucine, KrL-130/3.3 also showed a high level of safety with full survival (5/5) at concentrations up to 20 mg/mL (800 mg/kg dose).

Further studies revealed an unexpected variability when examining two different lots (93 and 94) of polymers having the same target molecular structure, KrL-120/5.0. As depicted in FIG. 34, lot 93 was found to cause substantial toxicity and systemic lethality after intraperitoneal administration, by comparison to lot 94. This was particularly surprising, because lot 93 had been shown to be safe for local application in the guinea pig sensitization study described above in FIG. 30. Lot 93 was also shown to be an effective microbicidal agent in vitro against gram-positive and gram-negative bacteria. Further, it was found to be safe and effective when used in vivo in both porcine open wound models and rodent closed wound models with microbial contamination.

In further analysis of lot 93 and 94, a notable difference was observed in self-assembly into multimeric structures as assessed by critical aggregation concentration (CAC). Lot 93, the more toxic lot, was found to have a higher critical aggregation concentration (130 µg/mL), indicating a weaker drive to self-assemble into multimeric structures than lot 94 (CAC: 51 µg/mL).

We also found that synthetic cationic polypeptide(s) that demonstrated low CACs and/or high viscosities when prepared in water were relatively safe when administered into the peritoneal cavity. As depicted by the data in FIG. 35, two preparations of lysine-L-leucine (KL) synthetic cationic polypeptide(s) with a block sequence arrangement of amino acid units, KL-170/3.3 and KL-140/2.5, were shown to be very safe upon intraperitoneal administration. These synthetic cationic polypeptide(s) and those having closely related structures demonstrate a high level of self-assembly, as measured by low CACs (typically single-digit µg/mL; see also FIG. 11 above). We also found that the synthetic cationic polypeptide(s) that demonstrated higher safety profiles after intraperitoneal application also demonstrated relatively high viscosity and/or firmness in texture analysis in aqueous preparations (see FIG. 13 through FIG. 17). Thus, we developed general principles as described herein for guiding those skilled in the art in the design of synthetic cationic polypeptide(s) that have lower risk of systemic toxicities.

Formulation additives were also found to affect the safety profile of synthetic cationic polypeptide(s) compositions that are administered intraperitoneally. As shown in FIG. 36, preparations of KL-140/2.5 in water or water and hydroxyethyl cellulose (HEC) demonstrated some differences in safety. Notably, preparations with higher HEC content were found to be more toxic, despite the fact that this additive is widely considered to be safe. FIG. 37 shows additional examples of change in formulation that can enhance toxicity upon intraperitoneal administration.

Taken together, these discoveries indicate that local tissue compatibility and systemic safety are not the same, and that it is important to address both. Notably, both polymer design features and formulation parameters can increase or decrease the risk of systemic toxicities. Regarding polymer design features, our data indicate that safer synthetic cationic polypeptide(s) can be generated by design features that promote self-assembly with lower critical aggregation concentrations and/or that promote higher viscosities. Further, we found that formulation additives should be selected in ways to maintain or enhance self-assembly of the synthetic cationic polypeptide(s) into multimeric structures and/or maintain or enhance polymer viscosity.

The ratio of dose-limiting systemic toxicity to local effective dose may be dependent on tissue sites and/or pathophysiological settings. Both the effective dose and the toxic dose may be determined after application in a specific site or pathophysiological setting. Alternatively, a type of "higher-hurdle" may be established by determining the systemic toxicity dose after application to a site with predictably high systemic absorption (such as the peritoneal cavity). The local effective dose can still be determined after application to the specific site or pathophysiological setting (e.g., limb injury, soft tissue infection, sinus infection).

In an embodiment, antimicrobial agents or antimicrobial compositions may be selected based in part on measures of local or systemic toxicity in vivo.

In an embodiment, antimicrobial agents or antimicrobial compositions may be selected based in part on measures of toxicity in vivo after intraperitoneal administration.

Particular embodiments of the invention may include antimicrobial agents or antimicrobial compositions that can be infused safely into the peritoneal cavity of mice at doses higher than the dose expected to be effective for reduction of microbial loads after local application to tissues other than the peritoneal cavity.

Example 8

Method of sterilization is important. We have found that the safety of antimicrobial pharmaceutical compositions based on synthetic cationic polypeptide(s) depends on the molecular design (especially the cationic-hydrophobic block sequence arrangement), the self-assembly of the polymer into multimeric structures, and viscosity. In an embodiment, sterilization of the antimicrobial pharmaceutical compositions is conducted by methods that maintain molecular integrity, multimeric structures, and viscosity.

FIGS. 38-41 demonstrate that traditional radiation sterilization techniques can cause breakdown in the molecular structure of synthetic cationic polypeptide(s) and loss of composition firmness, as assessed by texture analysis. E-beam sterilization of aqueous preparations of synthetic cationic polypeptides were also shown to cause a major loss in viscosity. Samples were observed to be as fluid as water. As such, radiation sterilization techniques need to be carefully controlled and/or modified for use in the sterilization of antimicrobial pharmaceutical compositions with synthetic cationic polypeptide(s).

By contrast to radiation techniques, both sterile filtration and heat sterilization (autoclaving) provide effective sterilization of antimicrobial pharmaceutical compositions while maintaining molecular structure of synthetic cationic polypeptide(s) and maintaining the desirable physical properties of aqueous compositions that include them. FIGS. 42-46 show SEC chromatograms that demonstrate maintenance of molecular integrity after sterilization by filtration and autoclaving.

Figure 47:
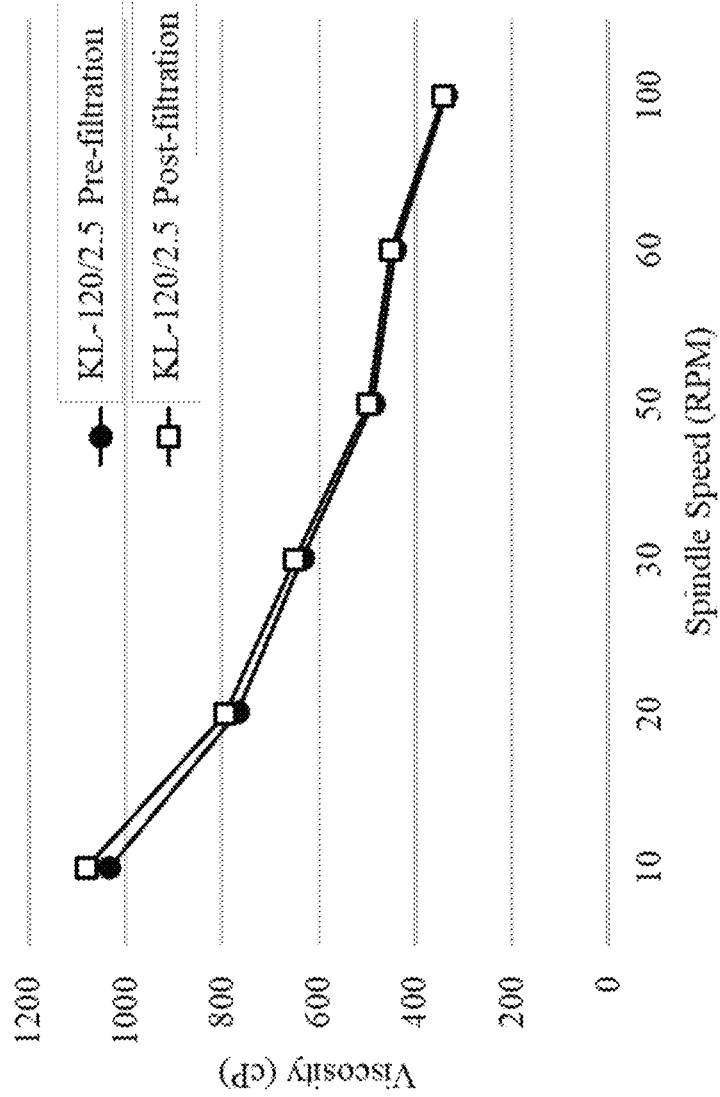
FIG. 47. Dynamic viscosity of synthetic cationic polypeptide(s) KL-120/2.5 (lot BAC004) at 2.0 wt % in water with 2.1% propylene glycol pre- and post-filter sterilization. Measured over 2 minutes using a Brookfield RVDV (EQ-AL-2014-16) rotational viscometer with size 21 spindle and size 13R chamber at room temperature.
Figure 48:
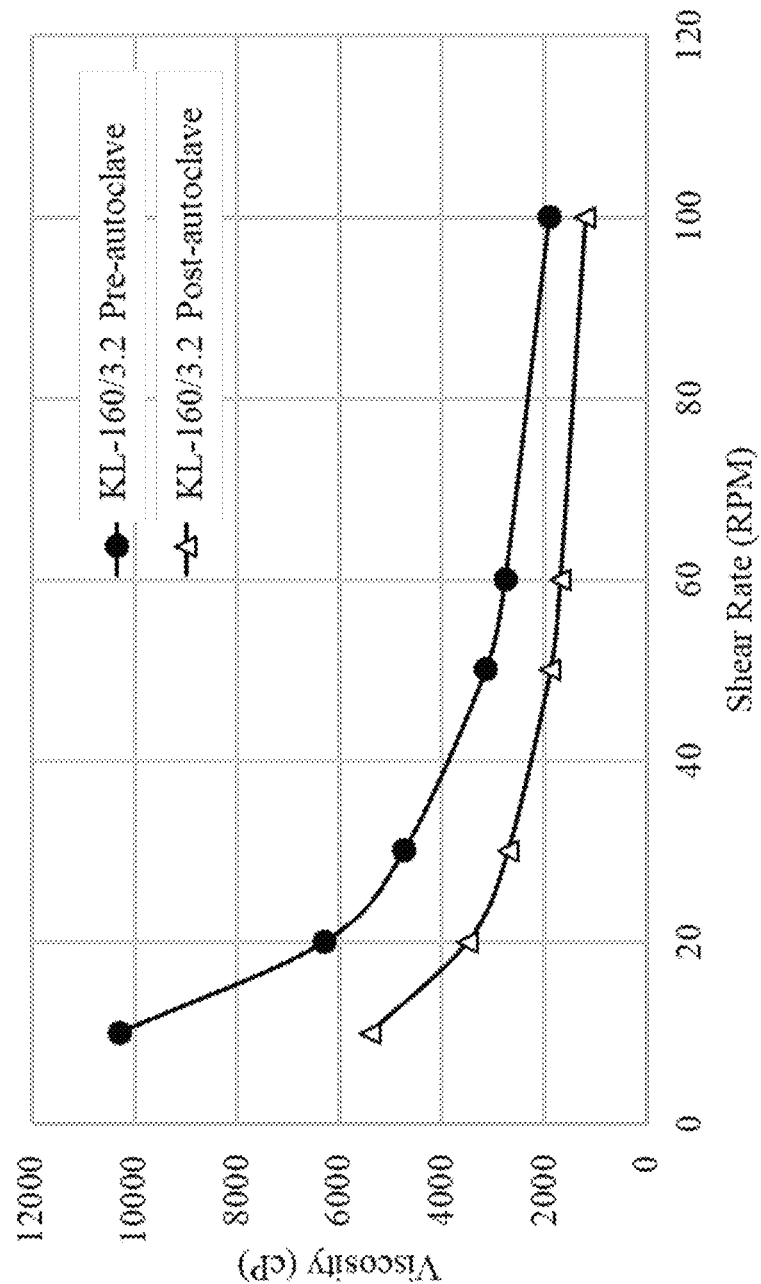
FIG. 48. Dynamic viscosity of synthetic cationic polypeptide(s) KL-160/3.2 (lot BAC003) at 2.0 wt % in water pre- and post-autoclave sterilization. Measured over 2 minutes using a Brookfield RVDV (EQ-AL-2014-16) rotational viscometer.
Figure 49:
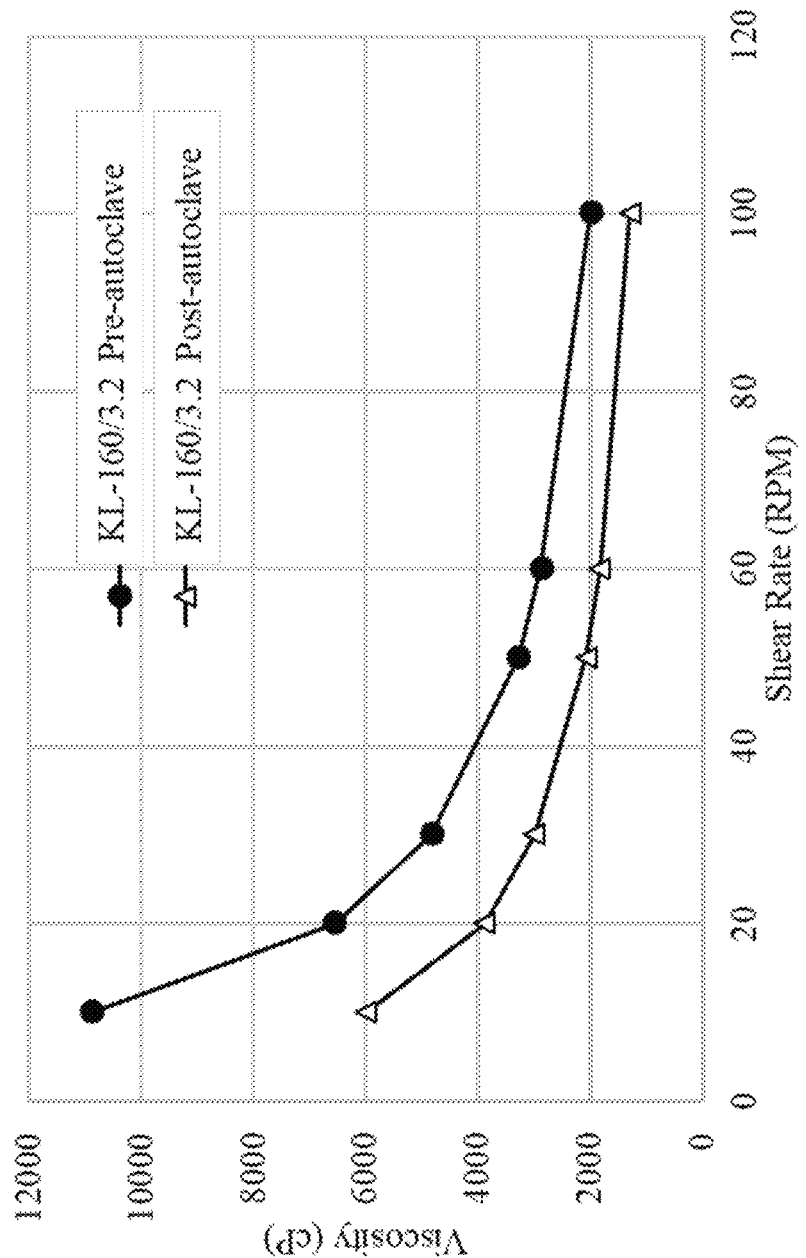
FIG. 49. Dynamic viscosity of synthetic cationic polypeptide(s) KL-160/3.2 (loit BAC003) at 2.0 wt % in water with 2.33% glycerol pre- and post-autoclave sterilization. Measured over 2 minutes using a Brookfield RVDV (EQ-AL-2014-16) rotational viscometer.
Figure 50:
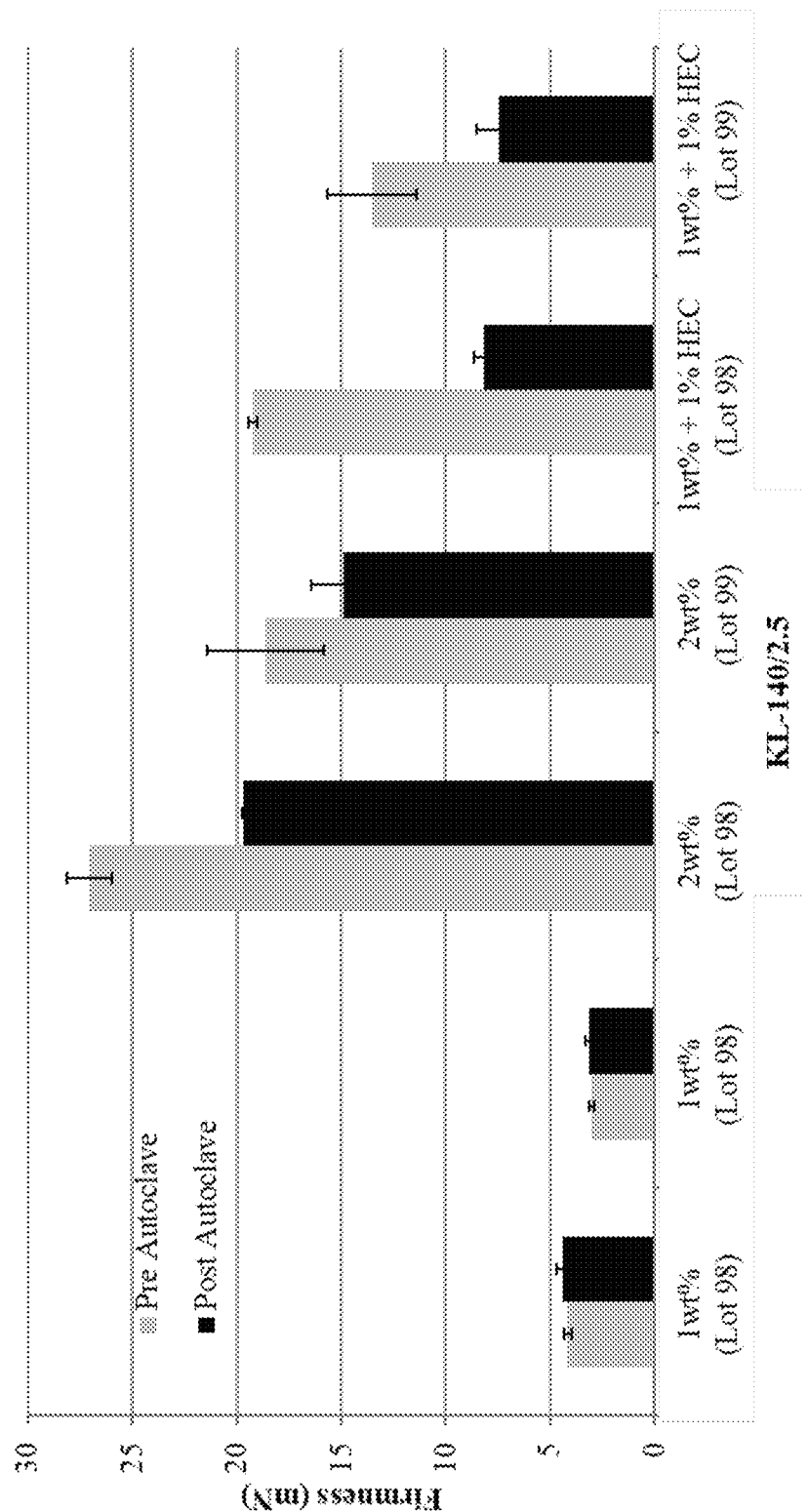
FIG. 50. Texture analysis of two lots of synthetic cationic polypeptide(s) KL-140/2.5 (98 and 99) at 1 and 2 wt % in water with and without 1% hydroxyethyl cellulose (HEC) pre-autoclave sterilization and post-autoclave sterilization. Measured using a TA.XT2 texture analyzer with a probe speed of 2 mm/s. Data indicate a maintenance of the beneficial property of firmness after autoclaving. Some overall decrease in firmness is observed at the higher concentration preparations and in preparations formulated with HEC.
Figure 51:
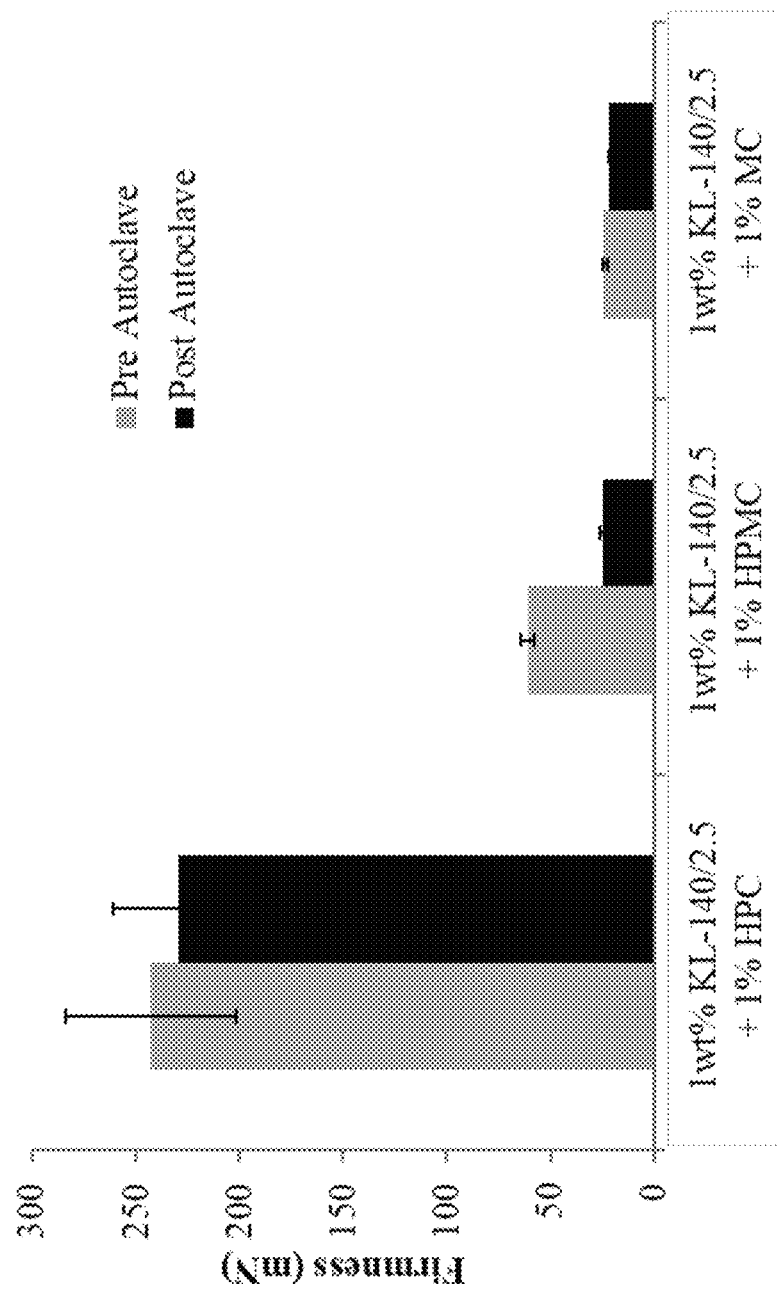
FIG. 51. Texture analysis of synthetic cationic polypeptide(s) KL-140/2.5 (lot 99) at 1 wt % in water with 1 wt % hydroxypropyl cellulose (HPC), hydroxypropyl methylcellulose (HPMC), or methylcellulose (MC) pre-autoclave sterilization and post-autoclave sterilization. Measured using a TA.XT2 texture analyzer with a probe speed of 2 mm/s.
Figure 52:
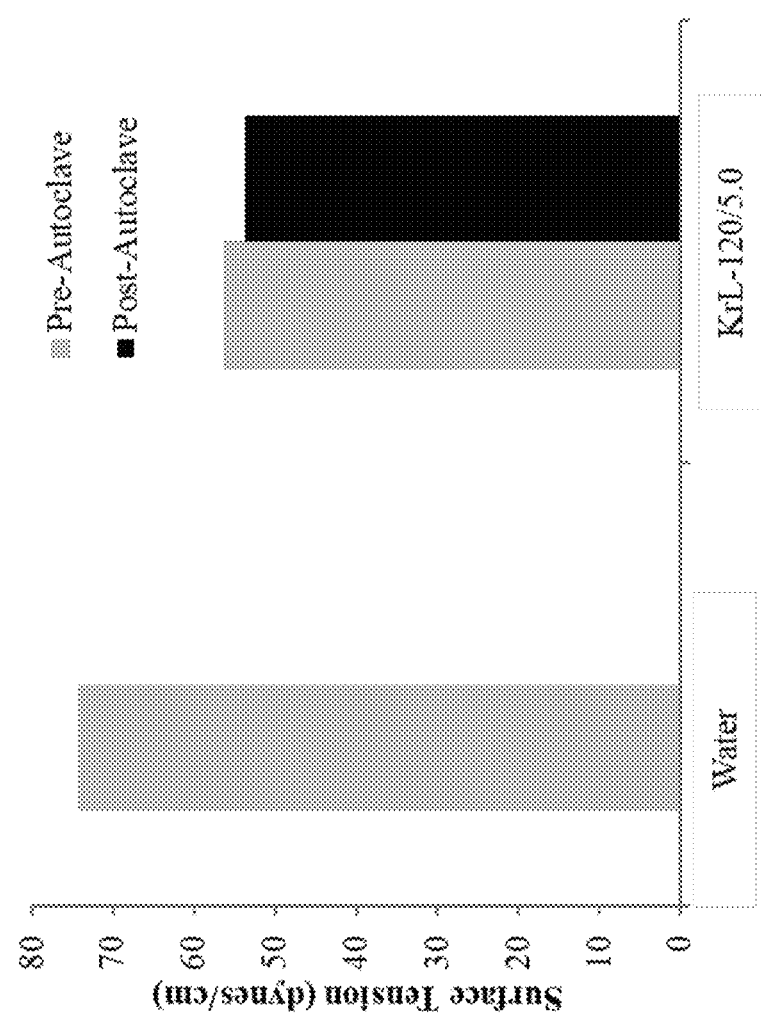
FIG. 52. Reduction of surface tension by preparations of synthetic cationic polypeptide(s) KrL-120/5.0 (lot 94) in water pre- and post-autoclave sterilization. Samples were prepared at 0.1 mM and assessed using TA.XT2 Texture Analyzer with a 500 g load cell, 5 cm diameter Du Nouy ring and probe speed of 0.2 mm/s at room temperature.

Sterilization by filtration and by autoclaving also maintain key beneficial physical properties of aqueous preparations and compositions that include synthetic cationic polypeptide(s). FIG. 47 demonstrates that an aqueous preparation of the synthetic cationic polypeptide(s) KL-120/2.5 (lot BAC004) at 1.25 wt % in water with 4.5 wt % mannitol showed nearly identical dynamic viscosity properties pre- and post-sterile filtration. FIG. 48 and FIG. 49 demonstrate that aqueous preparations of synthetic cationic poly peptide(s) KL-160/3.2 (lot BAC003) retain substantial levels of shear-thinning viscosities after autoclaving, although the overall level is somewhat reduced compared to pre-autoclaved samples. Further, autoclave sterilization of various aqueous preparations and compositions resulted in maintenance of the beneficial property of firmness, as assessed by texture analysis, although some decrease in firmness was noted (FIGS. 50 and 51). Data further indicated that the decrease in firmness was seen at higher concentrations of synthetic cationic polypeptide(s) and in the presence of certain additives, such as HEC. By way of explanation, the observed decreases in viscosity and firmness may be caused by a process of further dissolution and re-annealing of multimeric structures that may take place during the autoclaving process. That said, these preparations are considered to maintain the benefits of viscosity and firmness. FIG. 52 indicates that surfactant activity of synthetic cationic polypeptide(s) KrL-120/5.0 was maintained post-autoclave sterilization.

Example 9

To be both effective at inhibiting or killing microbes, and also carry a low risk of local and systemic toxicities, embodiments of an antimicrobial pharmaceutical composition as described herein provide both antimicrobial activity and beneficial physicochemical properties. The latter are associated with better self-assembly of the synthetic cationic polypeptide(s) into multimeric structures, viscosity higher than that found with aqueous preparations of many proteins, as exemplified by albumin, or both. In various embodiments a further decrease in the risk of both local and systemic toxicities is achieved by sterilization of the antimicrobial pharmaceutical composition, as long as the sterilization process is done in a manner that does not significantly adversely impact the molecular integrity of the synthetic cationic polypeptide(s) or the beneficial physicochemical properties of the antimicrobial pharmaceutical composition. Finally, to achieve both effectiveness and low risk of local and systemic toxicities in an in vivo setting, the method of application (including how much and how often), is important to consider, especially when the antimicrobial pharmaceutical composition is applied to tissues other than healthy, intact skin.

Figure 53:
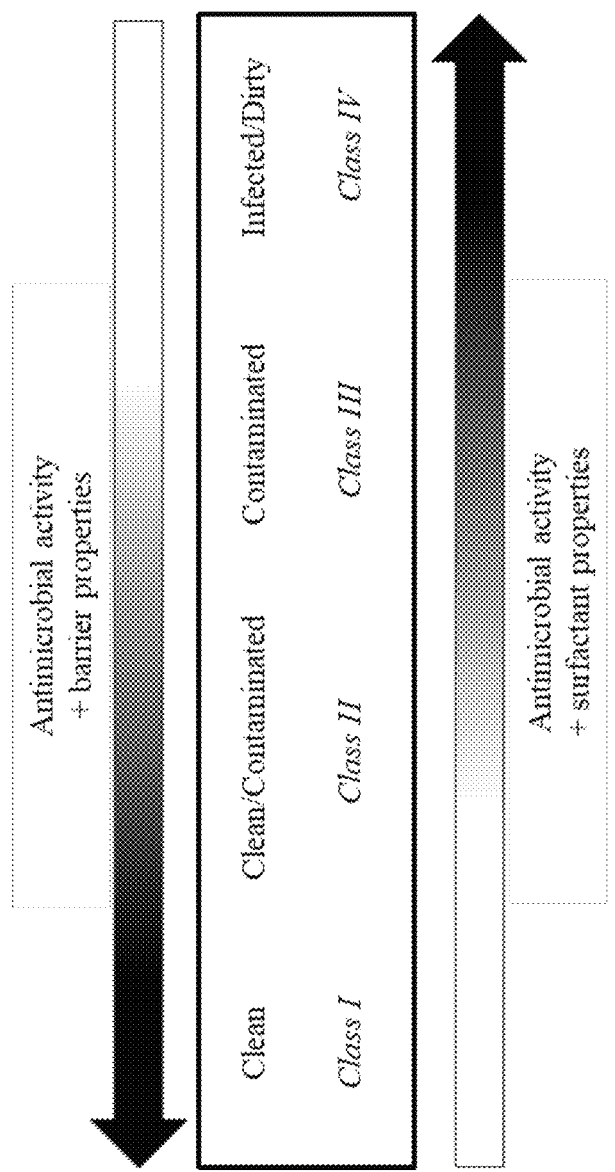
FIG. 53. Graphical depiction of wound classification.

Without limiting the scope of the invention, in some clinical settings, such as those involving large surgical or traumatic wounds, it may be important to apply the antimicrobial pharmaceutical composition as described herein "in abundance" to achieve antimicrobial effectiveness. As discussed above, "in abundance" refers to a total treatment dose of antimicrobial pharmaceutical composition that includes 1 g of synthetic cationic polypeptide(s) or more for a 70 kg person, which represents 14.3 mg/kg. When applying the antimicrobial pharmaceutical composition in abundance, the antimicrobial effectiveness, physicochemical properties, and the method of use should all be considered in combination in order to minimize the risk of local and systemic toxicity to the patient (human or animal). The antimicrobial pharmaceutical compositions described herein can be used in multiple and diverse clinical settings. In some embodiments, direct application to the exposed tissues of surgery and trauma are amongst the highest value uses. FIG. 53 provides a graphical depiction of wound classification commonly used in surgical settings. Wounds are classified as Class I (Clean), Class II (Clean/Contaminated), Class III (Contaminated), and Class IV (Dirty/Infected). In considering methods of use, in both Class I and Class II wound settings, the antimicrobial pharmaceutical compositions described herein may be applied to tissues prior to substantial microbial contamination. In some embodiments, a combination of direct microbicidal activity and microbial barrier properties is beneficial in such settings. Further, in Class III and Class IV wound settings, the antimicrobial pharmaceutical compositions described herein may be applied to tissues after significant microbial contamination, or biofilm formation, or overt infection. In some embodiments, a combination of direct microbicidal activity and surfactant properties is beneficial in such settings.

Figure 54:
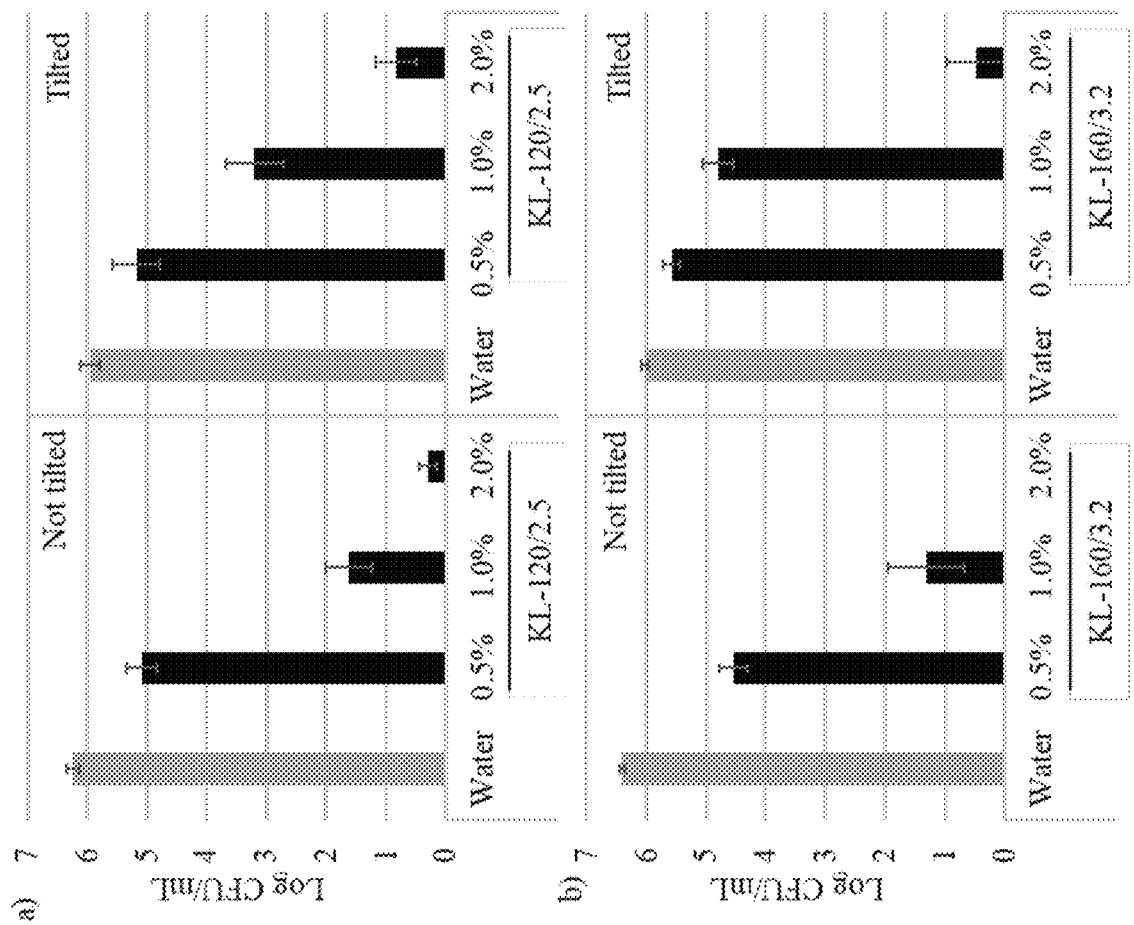
FIG. 54A-B. Results of pre-microbial inoculation treatment in porcine skin model ex vivo. Antimicrobial barrier properties of preparations of KL-120/2.5 (lot BAC003) and KL-160/3.2 (lot BAC004) demonstrated on porcine skin ex vivo. Data show log CFU of surviving $P.$ $aeruginosa$ 3 hours after inoculation of skin explants that were pretreated for 30 minutes with water (control; N=8) or pretreated with (a) 0.5-2.0 wt % KL-120/2.5 (N=8) or (b) 0.5-2.0 wt % KL-160/3.2 (N=8). In the "not tilted" group, explants remained horizontal throughout pretreatment with synthetic cationic polypeptide(s) preparations; in the "tilted" group, explants were tilted 90° to a vertical position for 15 minutes to encourage runoff of the synthetic cationic polypeptide(s) preparation coating prior to inoculation. *no microbes detected. Error bars depict SEM.

The benefit of a combination of direct microbicidal activity and microbial barrier properties can be illustrated in various test settings. FIG. 54 depicts the results of a porcine ex vivo skin model of microbial contamination. In this model, the skin explants can be placed horizontally and pre-treated with preparations of synthetic cationic polypeptide(s) or they can be tilted vertically for a period in order to encourage run off of the antimicrobial preparation. This method is designed to better mimic application to tissues in vivo. As the data indicate, preparations of both KL-120/2.5 and KL-160/3.2 are quite effective at both 1 wt % and 2 wt % on the horizontal tissue samples. However, when samples are tilted vertically for a period, the higher concentration preparations, which have a higher viscosity, are shown to be more effective. Both preparations have substantially more antimicrobial activity than required to treat a microbial load of this size.

Figure 55:
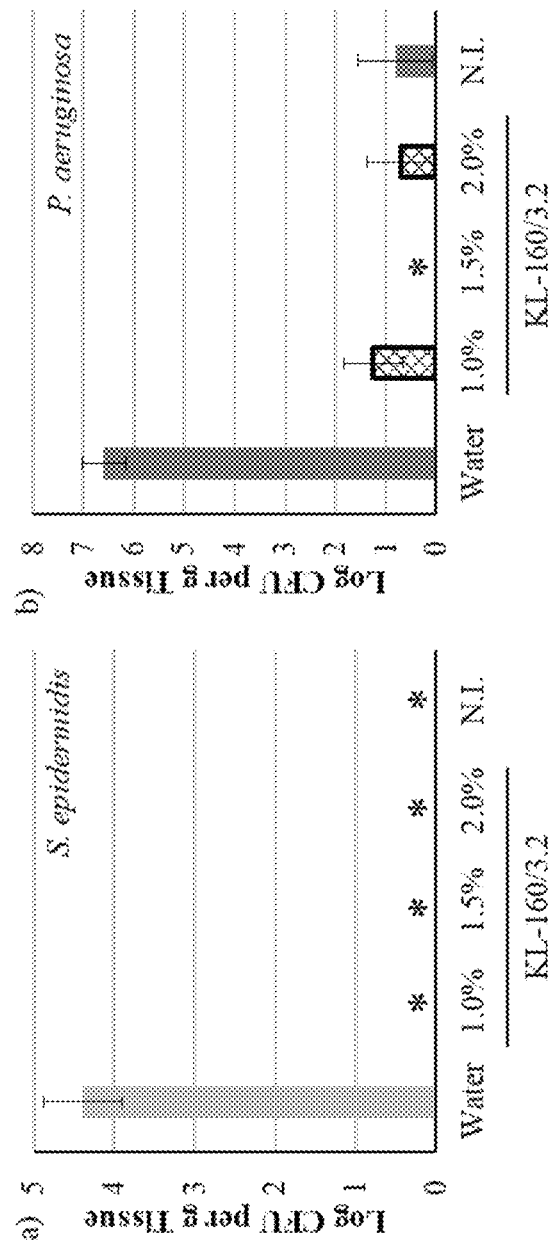
FIGS. 55A-B. Results of pre-microbial inoculation treatment in porcine open wound model. Preparations of synthetic cationic polypeptide(s) KL-160/3.2 (lot BAC003) prevents microbial contamination in a porcine model (N=5 wounds; 4 for "N.I."). a) $S.$ $epidermidis$ b) $P.$ $aeruginosa$. N.I.=No inoculation. Full-thickness wounds were pretreated with 1.0 mL of KL-160/3.2 at the concentrations depicted or water 15 min prior to inoculation with a mixed culture of $S.$ $epidermidis$ and $P.$ $aeruginosa$. Total microbial counts, as well as selective $S.$ $epidermidis$ and $P.$ $aeruginosa$ counts, were assessed after 4 hours. In all cases, the difference between control and KL-160/3.2 was significant at $p<0.01$. *No microbes detected.
Figure 56:
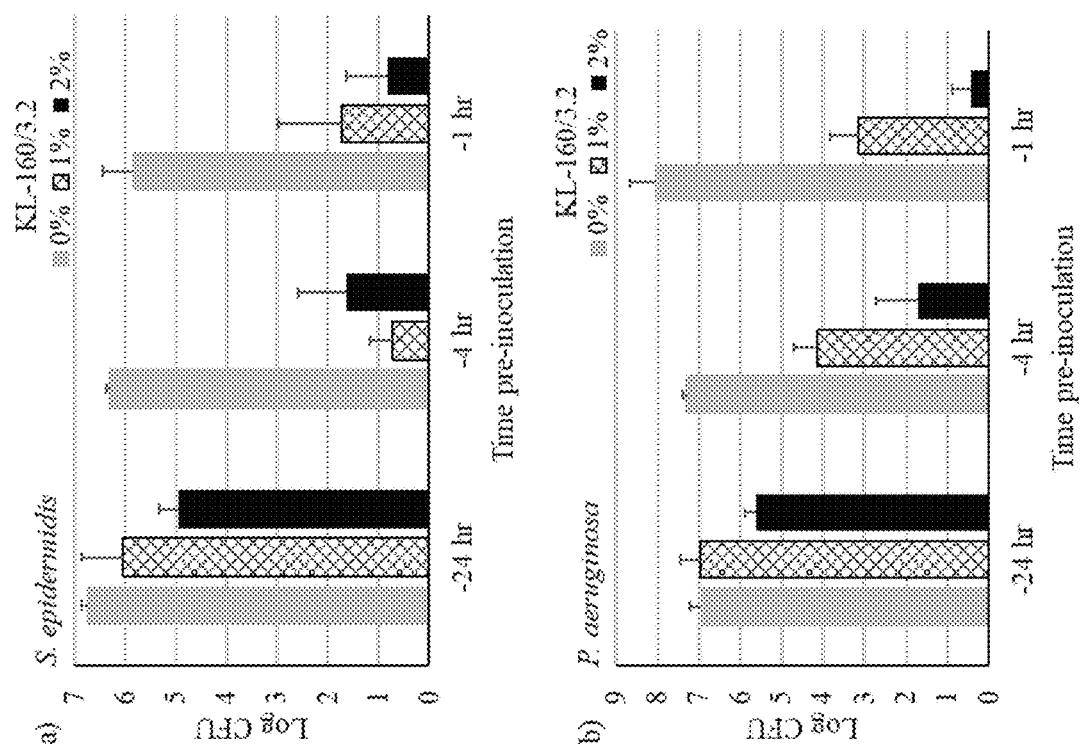
FIGS. 56A-B. Results of pre-microbial inoculation treatment in porcine open wound model. KL-160/3.2 (lot BAC003) prevents microbial contamination in a porcine model (N=4 wounds per group). a) $S.$ $epidermidis$ b) $P.$ $aeruginosa$. Full-thickness wounds were pretreated with 1.0 mL of KL-160/3.2 at the concentrations depicted or with water 24 h, 4 h, or 1 h prior to inoculation with a mixed culture of $S.$ $epidermidis$ and $P.$ $aeruginosa$. Total microbial counts, as well as selective $S.$ $epidermidis$ and $P.$ $aeruginosa$ counts, were assessed 4 hours after inoculation.
Figure 57:
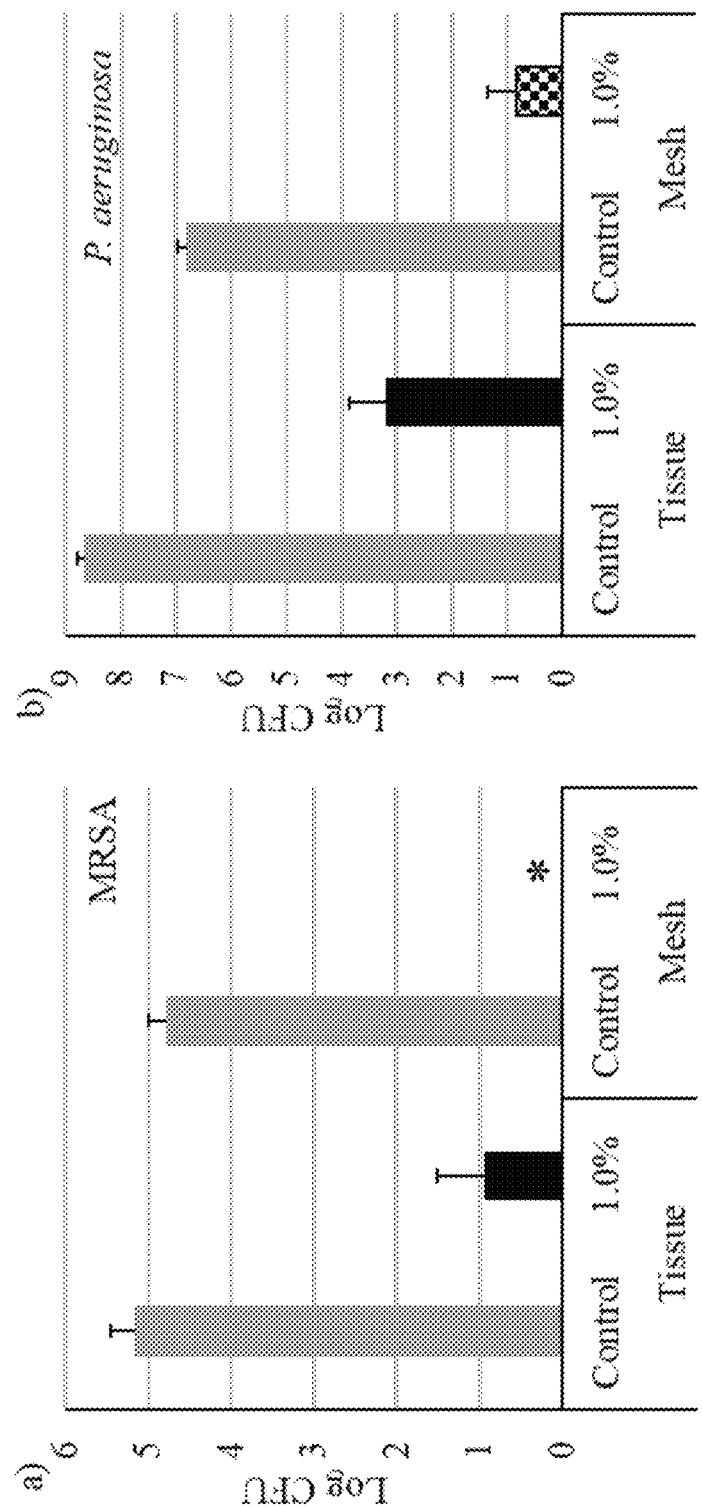
FIGS. 57A-B. Results of pre-microbial inoculation treatment in rodent closed wound model with surgical mesh. KL-160/3.2 (lot BAC003) (1 wt % in water) show activity against (a) MRSA (ATCC 33593) and (b) $P.$ $aeruginosa$ (ATCC 27317) in a rodent closed wound model with foreign body (KL-160/3.2 N=6; Control N=8; Sprague-Dawley rats). Log CFU shown per gram tissue for biopsy samples and per implanted polypropylene mesh. KL-160/3.2 preparations were applied 15 min prior to microbial inoculation; microbial burden was assessed after 48 h. Differences between control and KL-160/3.2 groups for both microbes was significant at $p<0.0001$. *No microbes detected.

FIG. 55 depicts the results of a porcine open wound model in vivo in which synthetic cationic polypeptide(s) KL-160/3.2 preparations were applied to full thickness wounds 15 minutes prior to bacterial contamination. When assessed 4 hours after inoculation with a high density mixed culture of *S. epidermidis* and *P. aeruginosa*, treated wounds showed little, if any, microbial contamination of the tissue compared to controls. FIG. 56 demonstrates the effect of pretreatment of tissues prior to microbial contamination is both concentration and time dependent. Thus, in clinical settings, preferred embodiments include administering effective amounts of synthetic cationic polypeptide(s) compositions and repeat applications to tissues that are exposed over extended periods (e.g., extended surgeries or wounds involving delayed closure). FIG. 57 shows the results of pre-treatment of a rodent wound with an implanted surgical mesh (acting as a foreign body) prior to microbial inoculation. In this model, the wound is closed shortly after inoculation. As the data show, the single application of antimicrobial pharmaceutical composition with synthetic cationic polypeptides(s) KL-160/3.2 resulted in very substantial (multi-log) CFU reductions as assessed at 48 hours.

Taken together, these data demonstrate: (1) the benefits of direct microbicidal activity and microbial barrier properties; (2) the value of early treatment prior to substantial microbial contamination; and (3) the importance of treatment regimens that take into account both the duration of tissue exposure and the potential timing of microbial contamination.

The benefit of a combination of direct microbicidal activity and surfactant properties can also be illustrated in various test settings. As shown in FIG. 53, the antimicrobial compositions described herein can be applied in many and diverse clinical settings where there is already substantial microbial contamination of tissues, extant biofilms, or overt infection, or a combination of two or more. Such settings can include surgical procedures with Class III and Class IV wounds. These include treatments of surgical site infections, including those involving foreign bodies (e.g., periprosthetic joint infections, hernia mesh infections, breast implant infections, etc.). These settings also include most traumatic wounds, as well as surgical and non-surgical treatment of frequently contaminated areas, such as sinuses of the head (especially in patients with chronic sinusitis). Repair of surgical sites with foreign bodies, even those without overt infection, should also be considered at high risk for biofilm formation. As noted above, in these settings the antimicrobial pharmaceutical compositions described herein are likely to be applied to sites with extant microbial contamination. The combination of direct microbicidal activity and surfactant properties can be of special benefit.

Figure 58:
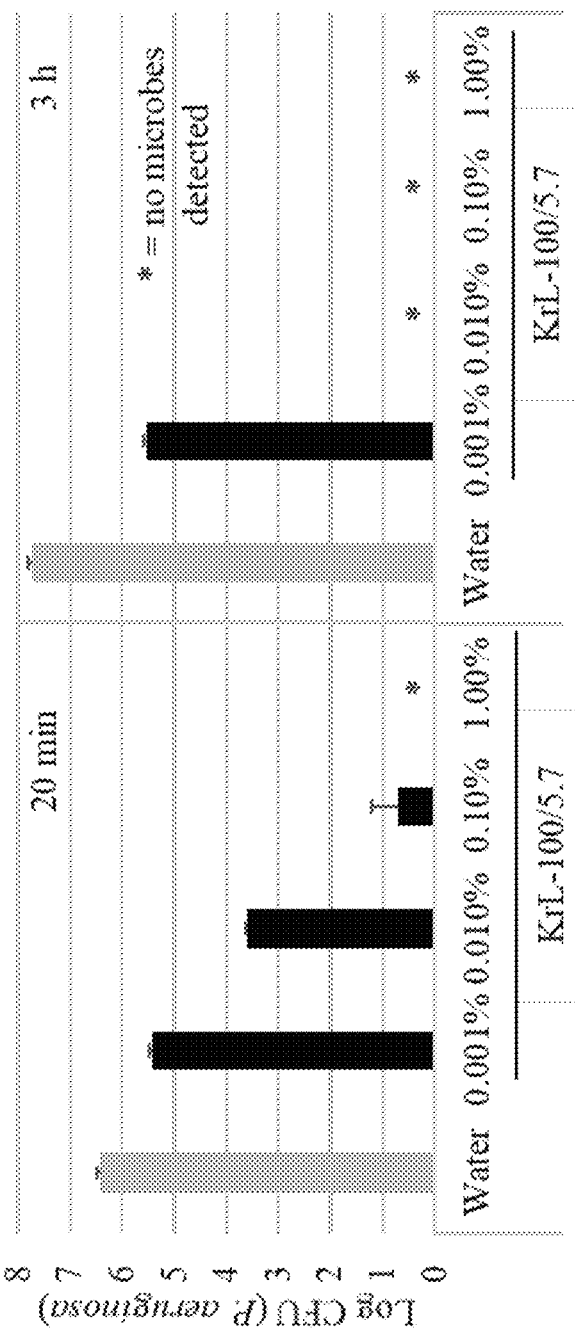
FIG. 58. Anti-biofilm activity. Minimum biofilm eradication concentration (MBEC) assay of synthetic cationic polypeptide(s) KrL-100/5.7 (lot BAC002). Activity against $P.$ $aeruginosa$ (ATCC BAA-47) in biofilms. $P.$ $aeruginosa$ biofilms were exposed to different concentrations of synthetic cationic polypeptide(s) (0.001%, 0.01%, 0.1%, and 1.0% in water) for 20 min or 3 h, and samples were processed for measurement of colony forming units (CFU). *=no microbes detected.
Figure 59:
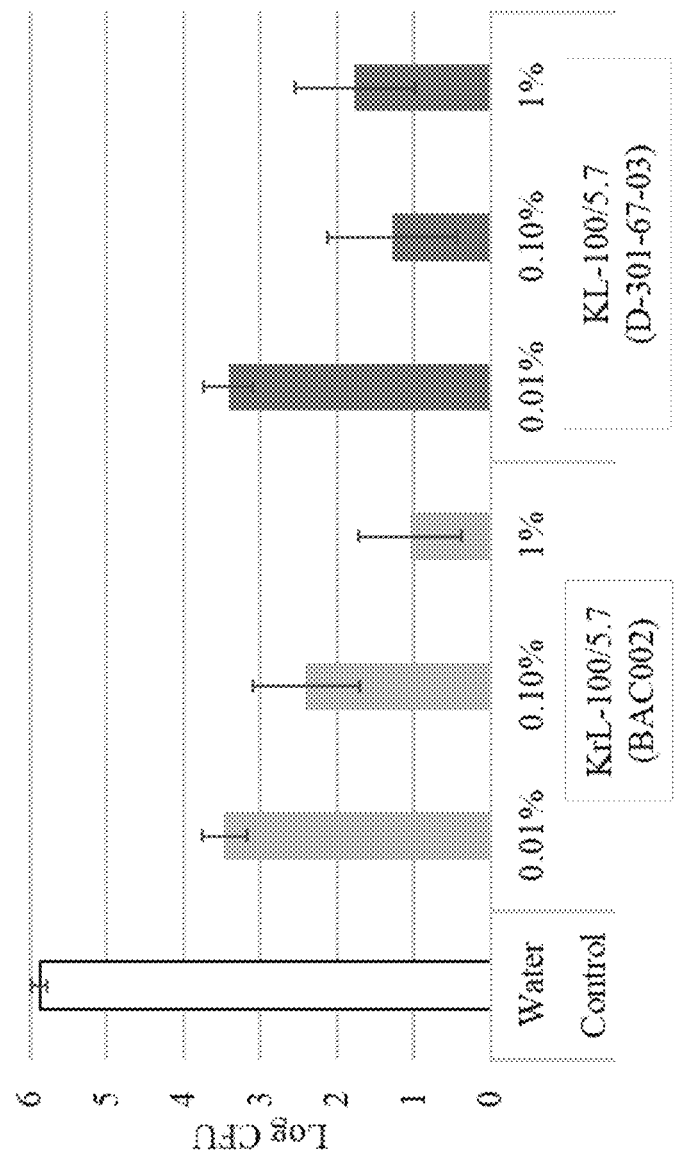
FIG. 59. Anti-biofilm activity. Minimum biofilm eradication concentration (MBEC) assay of preparations of synthetic cationic polypeptide(s) KrL-100/5.7 (Lot BAC002) and KL-100/5.7 (Lot D-301-67-03). Activity against $P.$ $aeruginosa$(ATCC BAA-47) in biofilms. $P.$ $aeruginosa$ biofilms were exposed to different concentrations of synthetic cationic polypeptide(s) preparations in water (0.01%, 0.1%, and 1.0%) for 3 h, and samples were processed for measurement of colony forming units (CFU).
Figure 60:
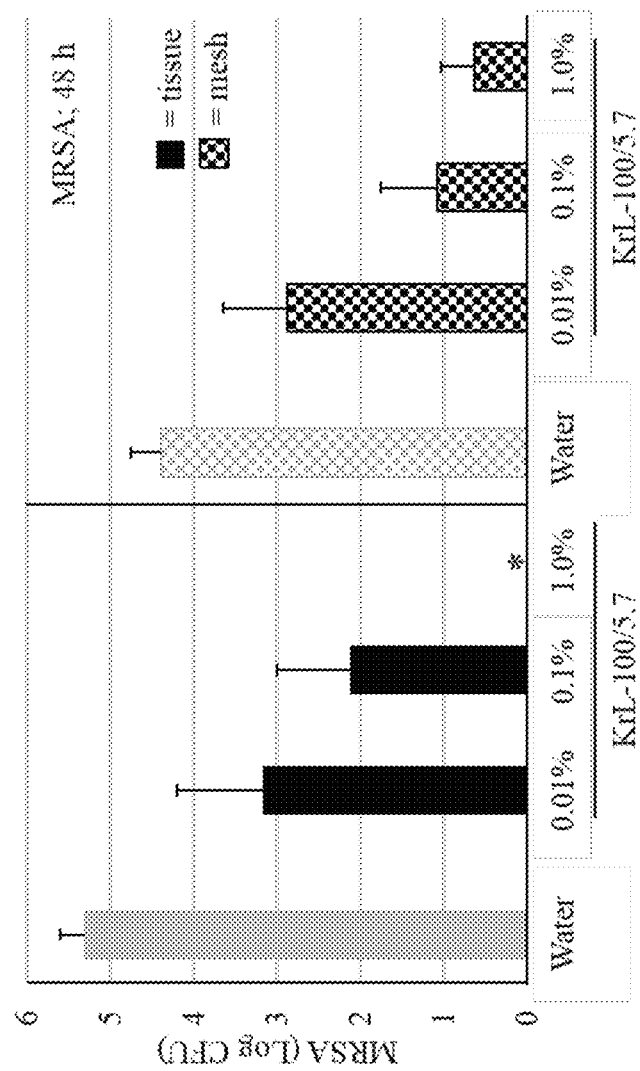
FIG. 60. Results of post-microbial inoculation treatment in rodent closed wound model with surgical mesh. Preparations of synthetic cationic polypeptide(s) KrL-100/5.7 (lot BAC002) show activity against MRSA (ATCC 33593) in a rodent closed-wound model with foreign body (KrL-100/5.7 N=6; Control N=8; Sprague-Dawley rats). Log CFU survival shown per gram tissue for biopsy samples and per implanted polypropylene mesh. KrL-100/5.7 preparations (0.01%, 0.1%, and 1.0%) were applied 15 minutes after microbial inoculation; microbial burden was assessed after 48 hours. Data are presented as mean+SEM. *No microbes detected.
Figure 61:
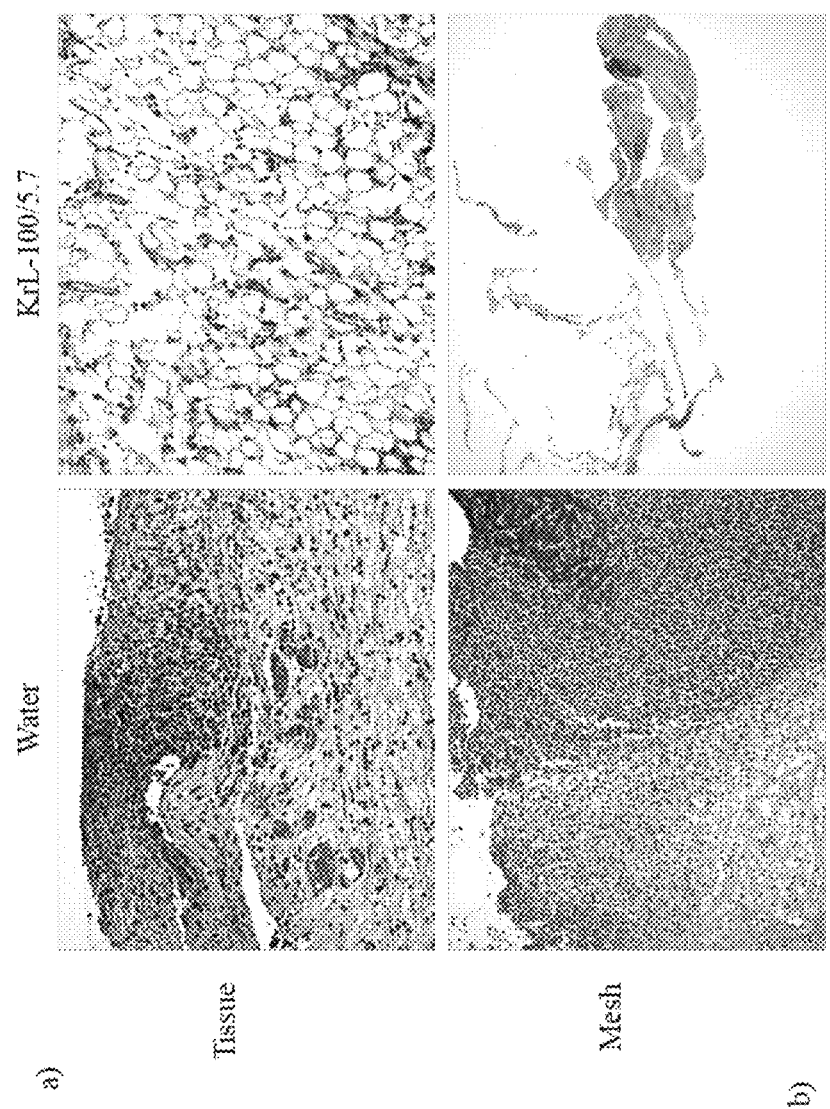
FIGS. 61A-B. Results of post-microbial inoculation treatment in rodent closed wound model with surgical mesh. (a) Histopathology of tissue biopsies and mesh with MRSA inoculation. Samples were processed for histology and were stained with H&E. (b) Inflammation scores were determined by microscopic analysis by an experienced veterinary pathologist.
Figure 62:
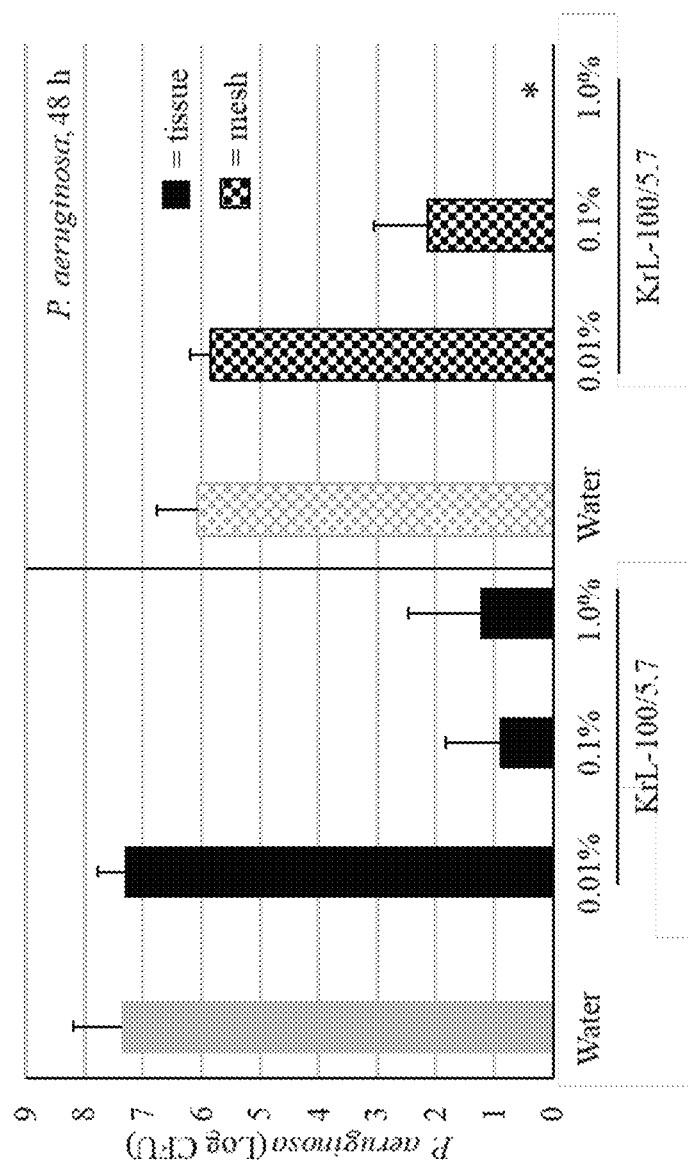
FIG. 62. Results of post-microbial inoculation treatment in rodent closed wound model with surgical mesh. Preparations of synthetic cationic polypeptide(s) KrL-100/5.7 (lot BAC002) show activity against $P.$ $aeruginosa$ (ATCC 27317) in a rodent closed-wound model with foreign body (KrL-100/5.7 N=6; Control N=8; Sprague-Dawley rats). Log CFU survival shown per gram tissue for biopsy samples and per implanted polypropylene mesh. KrL-100/5.7 preparations (0.01%, 0.1%, and 1.0%) were applied 15 minutes after microbial inoculation; microbial burden was assessed after 48 hours. Data are presented as mean+SEM. *No microbes detected.

FIG. 58 and FIG. 59 demonstrates potent activity against *P. aeruginosa* grown in biofilms using preparations of synthetic antimicrobial polypeptide(s) with both direct microbicidal activities and surfactant activity. FIGS. 60-63 depict the results of studies that demonstrate these same principles in vivo. The antimicrobial compositions described herein that demonstrate direct microbicidal activity and surfactant properties are highly effective when applied to tissue sites that are highly contaminated with microbes, both gram-positive (such as methicillin-resistant *S. aureus*) and gram-negative (such as *P. aeruginosa*).

In addition to substantially lowering microbial counts, in various embodiments these treatments appear to be tissue protective, which may be due in part to a reduction in tissue inflammation, a recognized source of tissue damage. In various embodiments reductions in inflammation can be obtained or enhanced by combining the antimicrobial compositions described herein with an anti-inflammatory agent.

This example illustrates the benefits of combining direct microbicidal activity with barrier properties and the benefits of combining direct microbicidal activity with surfactant activity. Notably, those skilled in the art can utilize the guidance provided herein to design synthetic cationic polypeptide(s) having all three functionalities: direct microbicidal activity, barrier properties, and surfactant activity. In the manufacture of a pharmaceutical composition with these multifunctional synthetic cationic polypeptide(s), it is important that formulation and sterilization be undertaken in a manner that supports these functionalities.

In various embodiments, antimicrobial compositions containing synthetic cationic polypeptides as described herein are preferred wherein the polypeptide(s) and the overall composition are designed to provide a high level of antimicrobial activity, coupled with a low risk of local and systemic toxicities. Physicochemical properties including self-assembly into multimeric structures and/or viscosity are desirable.

What is claimed is:

1. An antimicrobial pharmaceutical composition, comprising:
   an aqueous carrier; and
   at least one antimicrobial synthetic cationic polypeptide (s) dispersed in the aqueous carrier at a concentration in the range of about 0.01% to about 5%, by weight based on total weight of the antimicrobial pharmaceutical composition;
   wherein:
   the at least one antimicrobial synthetic cationic polypeptide(s) comprises at least 40 amino acid units;
   the at least one antimicrobial synthetic cationic polypeptide(s) comprises at least one cationic segment with a plurality of positively charged amino acid units at neutral pH and a hydrophobic segment with a plurality of hydrophobic amino acid units;
   the ratio of the length of the cationic segment to the length of the hydrophobic segment is between about 1.5 and about 6;

the at least one antimicrobial synthetic cationic polypeptide(s) at a concentration of 2 wt % in deionized water has a viscosity at 37° C. of 2 centistokes (cSt) or greater; and the aqueous carrier, containing the antimicrobial synthetic cationic polypeptide(s) at 2 wt %, has a viscosity at 37° C. that is greater than that of the aqueous carrier containing albumin at 2 wt % in place of the at least one antimicrobial synthetic cationic polypeptide(s).

2. The antimicrobial pharmaceutical composition of claim 1, wherein the at least one synthetic cationic polypeptide(s) comprises a cationic segment of 20-400 amino acid units and a hydrophobic segment of 5-60 amino acid units.

3. The antimicrobial pharmaceutical composition of claim 2, wherein the cationic segment of 20-400 amino acid units is substantially composed of lysine units.

4. The antimicrobial pharmaceutical composition of claim 2, wherein the hydrophobic segment of 5-60 amino acid units is substantially comprised of leucine units.

5. A method of reducing microbial load of tissues other than intact, healthy skin, comprising:
identifying a mammalian subject having a tissue site other than intact, healthy skin that is at risk of microbial contamination; and
administering the antimicrobial pharmaceutical composition of claim 1 to the site in an amount effective to at least partially protect the tissue site from becoming contaminated with microbes.

6. A method of reducing microbial load of tissues other than intact, healthy skin, comprising:
identifying a mammalian subject having a tissue site other than intact, healthy skin that microbially contaminated; and
administering the antimicrobial pharmaceutical composition of claim 1 to the site in an amount effective to reduce microbial contamination of the tissue compared to before treatment.

7. The antimicrobial pharmaceutical composition of claim 1, wherein the aqueous carrier is water or an aqueous solution of a pharmaceutically acceptable salt.

8. The antimicrobial pharmaceutical composition of claim 1, wherein the aqueous carrier further comprises at least one non-ionic additive(s).

9. The antimicrobial pharmaceutical composition of claim 8, wherein the non-ionic additive(s) is present in an amount effective to increase the osmotic concentration of the antimicrobial pharmaceutical composition to a value that is at least 10% greater than that of the antimicrobial pharmaceutical composition without said non-ionic additive(s).

10. The antimicrobial pharmaceutical composition of claim 8, wherein the non-ionic additive is selected from the group consisting of dextrose, mannitol, glycerol, xylitol, sorbitol, surfactant(s), and combinations thereof.

11. The antimicrobial pharmaceutical composition of claim 1, wherein the aqueous carrier further comprises an additive in an amount that increases the viscosity of the antimicrobial pharmaceutical composition.

12. The antimicrobial pharmaceutical composition of claim 1, wherein the aqueous carrier further comprises an additive in an amount that decreases the viscosity of the antimicrobial pharmaceutical composition.

13. The antimicrobial pharmaceutical composition of claim 1, wherein the antimicrobial pharmaceutical composition is sterilized by at least one sterilization technique(s) configured to achieve a sterilized antimicrobial pharmaceutical composition with the antimicrobial synthetic cationic polypeptide(s) having a weight average molecular weight comparable to that of the antimicrobial synthetic cationic block polypeptide(s) of the antimicrobial pharmaceutical composition without sterilization by said sterilization technique(s).

14. The antimicrobial pharmaceutical composition of claim 1, wherein the antimicrobial pharmaceutical composition is sterilized by at least one sterilization technique(s) configured to achieve a sterilized antimicrobial pharmaceutical composition with the antimicrobial synthetic cationic polypeptide(s) having a weight average molecular weight and dispersity comparable to that of the antimicrobial synthetic cationic block polypeptide(s) of the antimicrobial pharmaceutical composition without sterilization by said sterilization technique(s).

15. The antimicrobial pharmaceutical composition of claim 1, wherein the antimicrobial pharmaceutical composition is sterilized by at least one sterilization technique(s) configured to achieve a sterilized antimicrobial pharmaceutical composition having a viscosity level at 37° C. that is comparable to that of the antimicrobial pharmaceutical composition without sterilization by said sterilization technique(s).

16. The antimicrobial pharmaceutical composition of claim 15, wherein the viscosity of the sterilized antimicrobial pharmaceutical composition at 37° C. is in the range of 20% to 200% of the viscosity of an otherwise comparable unsterilized antimicrobial pharmaceutical composition.

17. The antimicrobial pharmaceutical composition of claim 1, wherein the antimicrobial synthetic cationic block polypeptide(s), in deionized water at 37° C. at a concentration of 3 wt %, forms a self-supporting hydrogel.

* * * * *

UNITED STATES PATENT AND TRADEMARK OFFICE
CERTIFICATE OF CORRECTION

PATENT NO. : 12,268,722 B2
APPLICATION NO. : 17/654021
DATED : April 8, 2025
INVENTOR(S) : Michael P. Bevilacqua It is certified that error appears in the above-identified patent and that said Letters Patent is hereby corrected as shown below:

In the Specification

Column 9, Line 5, delete "KL-160/3.2 (loit BAC003)" and insert -- KL-160/3.2 (lot BAC003) --.

Column 9, Line 32, delete "FIG. 54A-B." and insert -- FIGS. 54A-B. --.

Column 10, Line 27-28, delete "against P. aeruginosa(ATCC BAA-47)" and insert -- against P. aeruginosa (ATCC BAA-47) --.

Column 19, Line 9, delete "ornithine (0). Cationic" and insert -- ornithine (O). Cationic --.

Column 20, Line 29-31, delete "$K_{55}L_{30}$, $K_{55}(raC-L)_5$, $K_{55}(raC-L)_5$-RAN, $K_{55}(raC-L)_{10}$, $K_{55}(raC-L)_{10}$-RAN, $K_{55}(raC-L)_{20}$, $R_{55}H(raC-L)_{20}$, $K_{55}(raC-L)_{20}$-RAN, $K_{55}(rac-L)_{30}$," and insert -- $K_{55}L_{30}$, $K_{55}(rac\text{ -}L)_5$, $K_{55}(rac-L)_5$-RAN, $K_{55}(rac-L)_{10}$, $K_{55}(rac-L)_{10}$-RAN, $K_{55}(rac\text{ -}L)_{20}$, $R_{55}H(rac-L)_{20}$, $K_{55}(rac-L)_{20}$-RAN, $K_{55}(rac-L)_{30}$, --.

Column 20, Line 31, delete "$K_{55}(rac-L)_{20}$, $K_{55}(raC-I)_{20}$, $K_{55}(rac-L/F)_{20}$," and insert -- $K_{55}(rac-L)_{20}$, $K_{55}(rac-I)_{20}$, $K_{55}(rac-L/F)_{20}$, --.

Column 20, Line 33, delete "$K_{80}$, $K_{50}(raC-L)_{20}$, $K_{90}(rac-L)_{30}$," and insert -- $K_{80}$, $K_{80}(rac-L)_{20}$, $K_{90}(rac-L)_{30}$, --.

Column 20, Line 42-43, delete "$K_{180}(rac-L)_{20}$, $K_{180}(raC-L)_{36}$, $K_{180}(raC-L)_{54}$, $K_{190}L_{10}$," and insert -- $K_{180}(rac-L)_{20}$, $K_{180}(rac-L)_{36}$, $K_{180}(rac-L)_{54}$, $K_{190}L_{10}$, --.

Column 20, Line 43, delete "$K_{200}L_{50}$, $PEG_{205}(raC-L)_{20}$, $K_{256}$," and insert -- $K_{200}L_{50}$, $PEG_{205}(rac-L)_{20}$, $K_{256}$, --.

Signed and Sealed this
Ninth Day of December, 2025

John A. Squires
*Director of the United States Patent and Trademark Office*

Column 26, Line 52, delete "tension (FIG. 26) Synthetic" and insert -- tension (FIG. 26). Synthetic --.

Column 27, Line 56, delete "mg/kg to160 mg/kg" and insert -- mg/kg to 160 mg/kg --.